(12) United States Patent
Kolesnick et al.

(10) Patent No.: US 7,301,017 B2
(45) Date of Patent: Nov. 27, 2007

(54) KINASE SUPPRESSOR OF RAS INACTIVATION FOR THERAPY OF RAS MEDIATED TUMORIGENESIS

(76) Inventors: Richard N. Kolesnick, 343 E. 74th St., Apt. 18A, New York, NY (US) 10021; Hongmei R. Xing, 539 W. 112th St., Apt. 6C, New York, NY (US) 10025

(*) Notice: Subject to any disclaimer, the term of this patent is extended or adjusted under 35 U.S.C. 154(b) by 278 days.

(21) Appl. No.: 10/727,358

(22) Filed: Dec. 3, 2003

(65) Prior Publication Data

US 2005/0037455 A1    Feb. 17, 2005

Related U.S. Application Data

(63) Continuation-in-part of application No. PCT/US03/16961, filed on May 29, 2003.

(60) Provisional application No. 60/460,023, filed on Apr. 3, 2003, provisional application No. 60/384,228, filed on May 30, 2002.

(51) Int. Cl.
*C07H 21/04* (2006.01)

(52) U.S. Cl. .................................................. 536/24.5

(58) Field of Classification Search ............... 536/23.1, 536/24.5; 514/44
See application file for complete search history.

(56) References Cited

U.S. PATENT DOCUMENTS

| | | | |
|---|---|---|---|
| 4,016,043 A * | 4/1977 | Schuurs et al. ................ | 435/5 |
| 5,591,721 A | 1/1997 | Agrawal et al. | |
| 5,700,675 A | 12/1997 | Rubin et al. | |
| 5,747,275 A | 5/1998 | Rubin et al. | |
| 5,747,288 A * | 5/1998 | Rubin et al. ................ | 435/69.1 |
| 6,261,834 B1 * | 7/2001 | Srivastava ................ | 435/320.1 |
| 6,277,981 B1 | 8/2001 | Tu et al. | |
| 6,329,203 B1 * | 12/2001 | Bennett et al. ............ | 435/377 |
| 6,416,951 B1 | 7/2002 | Schmidt et al. | |
| 6,500,615 B1 | 12/2002 | Schmidt et al. | |
| 2003/0051267 A1 | 3/2003 | McNeish et al. | |
| 2003/0109466 A1 * | 6/2003 | Monia et al. ................ | 514/44 |

FOREIGN PATENT DOCUMENTS

| WO | WO97/21820 | 6/1997 |
|---|---|---|
| WO | WO03025144 A | 3/2003 |
| WO | 03/016961 | 5/2003 |

OTHER PUBLICATIONS

WO 99/27105 (abstract only) attached is the result #9 of sequence search result against SEQ ID No.: 5 performed on Oct. 30, 2006.*
Agrawal, S., Temsamani, J. & Tang, Y.Y. (1991) Proc. Natl. Acad Sci U.S.A. 88:7595-7599.
Bernhard, E.J. et al. (2000) Cancer Res. 60:6597-6600.
Dean et al. (1994) J. Biol. Chem. 269:16446-16424.
Duff et al. (1995) J. Biol. Chem. 270:7161-7166.
Genbank Accession No. U43585; ROD Jan. 30, 1996.
Genbank Accession NM_013571; ROD Jan. 7, 2002.
Gupta, A.K. et al. (2001) Cancer Ras 61:4278-4282.
Ho et al. (1996) Nucl Acids Res 24:1901-1907.
Ho et al. (1998) Nature Biotechnology 16:59-630.
Kabanov, et al. (1990) FEBS Lett. 259:327.
Lozano, J. et al (2003) Cancer Research 63:4232-4238.
Monia et al. (1992) J. Biol. Chem. 267:19954-19962.
Nguyen, A. et al. (2002) Mol. Cell Biol. 22:3035-3045.
Therrien, M. et al. (1995) Cell 83:879-888.
Wang et al. (1995) Proc. Natl. Acad. Sci. USA 92:3318-3322.
Xing, H.R., Lozano, J. and Kolesnick, R. (2000) J. Biol. Chem. 275:17267-17280.
Xing, H.R. and Kolesnick, R. (2001) J. Biol. Chem. 276: 9733-9741.
Xing, H.R. and Kolesnick, R. (2002) Proc. Amer. Assoc. Cancer Res. 43:720 (Abstract #3571).
Xing, H.R. et al. (2003) Nature Med. 9:1266-1268 (Epub Sep. 7, 2003).
Xing, H.R. et al. (2003) Proc. Amer. Assoc. Cancer Res. 44(2):192 (Abstract #960).
Yamagami et al. (1996) Blood 87:2878-2884.
Almoguera, C. et al (1988) Cell. 53:549-554.
Balaban, N. et al. (1996) Biochim Biophys Acta. 1314:147-156.
Banerjee, D. (2001) Curr Opin Investig Drugs 2:574-580.
Bennett et al. (1994) J. Immunol. 152:3530-3540.
Bernhard, E.J. et al. (1998) Cancer Res. 58:1754-1761.
Bos, J. (1989) Cancer Res. 49: 4683-4689.
Brummelkamp, T.R. et al. (2002) Cancer Cell 2:243-247.
Denouel-Galy, A. et al. (1998) Curr. Biol. 8:46-55.
Geary, R.S. et al. (1997) Anticancer Drug Des 12:383-393.
Gokhale, P.C. et al. (1999) Antisense Nucleic Acid Dru Dev. 9:191-201.
Grant, M.L. et al. (1990) Oncogene 5:1159-1164.
Gupta, A.K. et al. (2000) Radiat Res. 154:64-72.
Henry, S.P. et al. (1997) Anticancer Drug Des 12:395-408.
Jones, H. et al. (2001) Semin Radiat Oncol. 11:328-337.
Kornfeld, K., Hom, D.B. & Horvitz, H.R. (1995) Cell 83:903-913.
Kushner, D.M. and Silverman, R.H. (2000) Curr Oncol Rep 2:23-30.

(Continued)

*Primary Examiner*—Brian Whiteman
(74) *Attorney, Agent, or Firm*—Klauber & Jackson, LLC

(57) ABSTRACT

The present invention relates to methods and compositions for the specific inhibition of kinase suppressor of Ras (KSR). In particular, the invention provides genetic approaches and nucleic acids for the specific inhibition of KSR, particularly of KSR expression. The invention relates to antisense oligonucleotides and the expression of nucleic acid which is substantially complementary to KSR RNA. Oligonucleotide and nucleic acid compositions are provided. The invention provides methods to inhibit KSR, including inhibition of KSR expression. Methods for blocking gf Ras mediated tumorigenesis, metastasis, and for cancer therapy are provided. Methods for conferring radiosensitivity to cells are also provided.

28 Claims, 43 Drawing Sheets

OTHER PUBLICATIONS

Laptev et al. (1994) Biochem. 33:11033-11039.
Migley, R.S. and Kerr, D.J. (2002) Crit Rev Oncol Hematol. 44:109-120.
Mishra et al. (1994) Life Sciences 317:977-982.
McKenna, W.G. et al. (1990) Cancer Res 50:97-102.
Ogiso, Y. et al. (1994) Gene Ther 1:403-407.
Ohmachi, M. et al. (2002) Curr Biol 12:427-433.
Ojala et al (1997) Antisense Nucl Drug Dev. 7:31-38.
Sundaram, M. & Han, M. (1995) Cell 83:889-901.
Xing, H., Kornfeld, K. & Muslin, A.J. (1997) Curr. Biol. 7:294-300.
Yao, B. et al. (1995) Nature 378:307-310.
Zhang, Y. et al. (1997) Cell 89:63-72.
Roy, Francis et al, 2002, KSR is a scaffold required for activation of the ERK/MARK module, Genes & Development vol. 16, No. 4, pp. 427-438.
Yan, F, et al, 2001, Cancer Research, Kinase Suppressor of Ras Determines Survival of Intestinal Epithelial Cells Exposed in tumor Necrosis Factor, vol. 16, pp. 8668-8675.

* cited by examiner a - KSR +/+ b - KSR -/- c - KSR -/- d - EGFR -/-

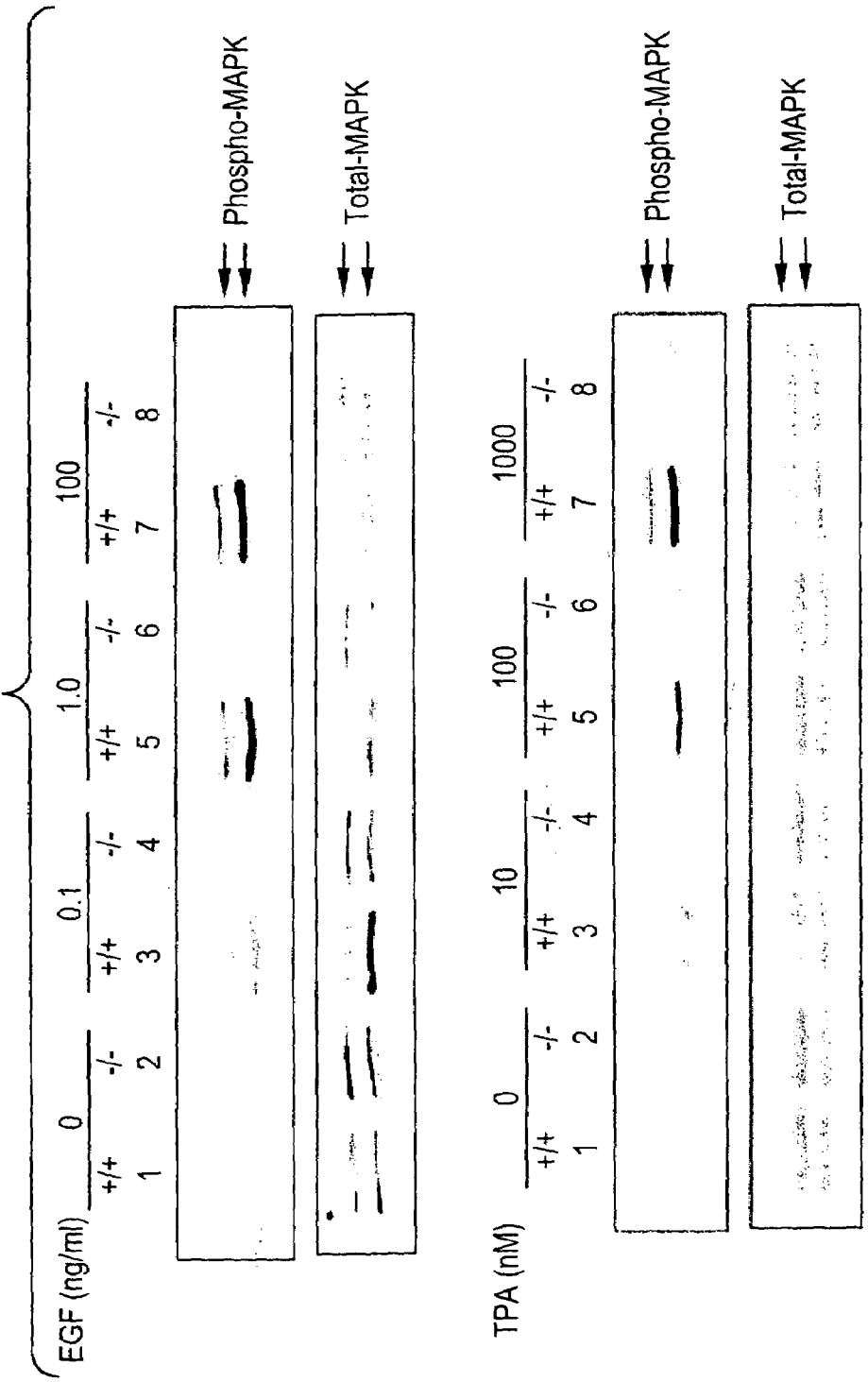

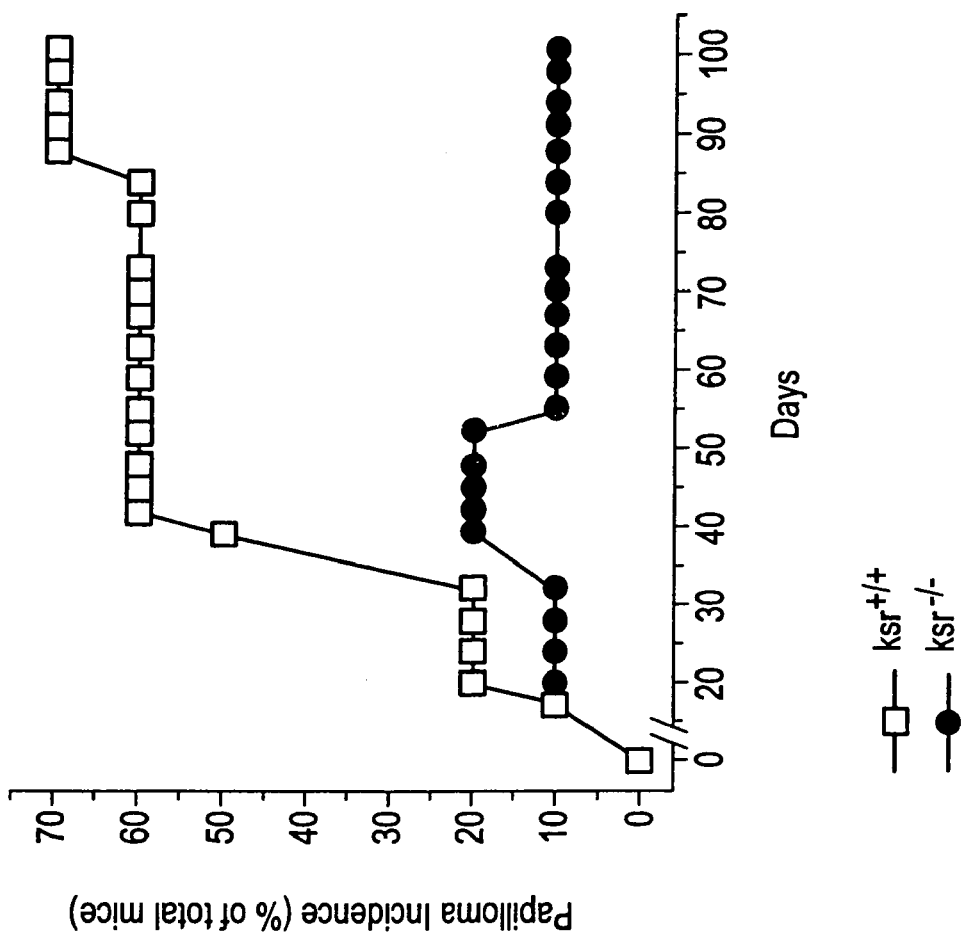

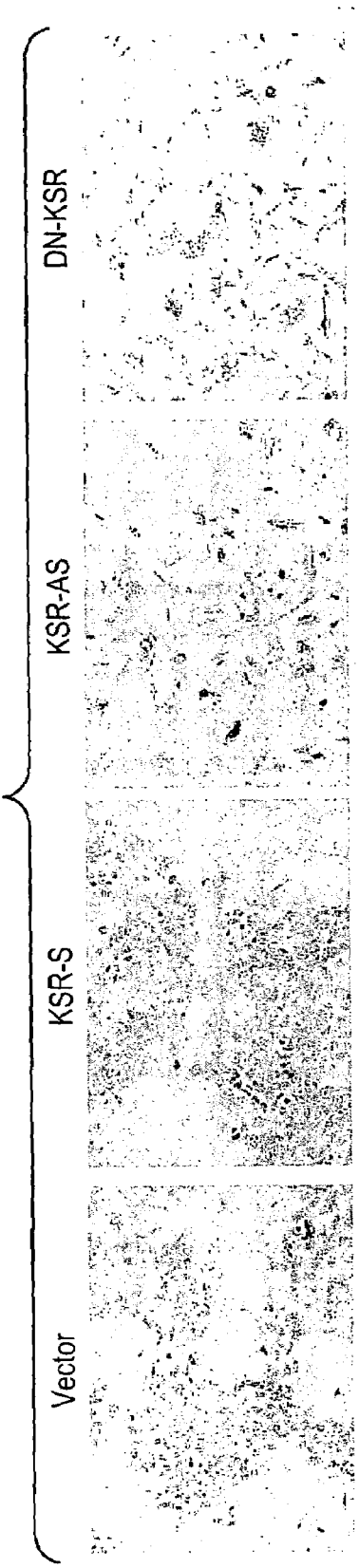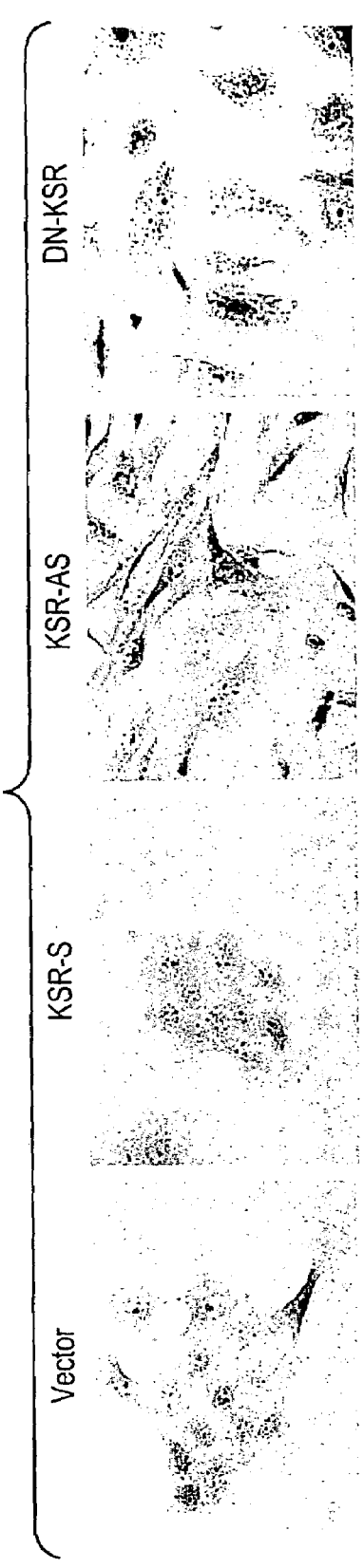

FIG. 6B

|        | % G1 | % S  | % G2 |
|--------|------|------|------|
| Vector | 40.1 | 45.1 | 14.8 |
| KSR-S  | 25.2 | 60.8 | 14.0 |
| KSR-AS | 16.4 | 23.2 | 60.4 |
| DN-KSR | 24.2 | 24.8 | 51.0 |

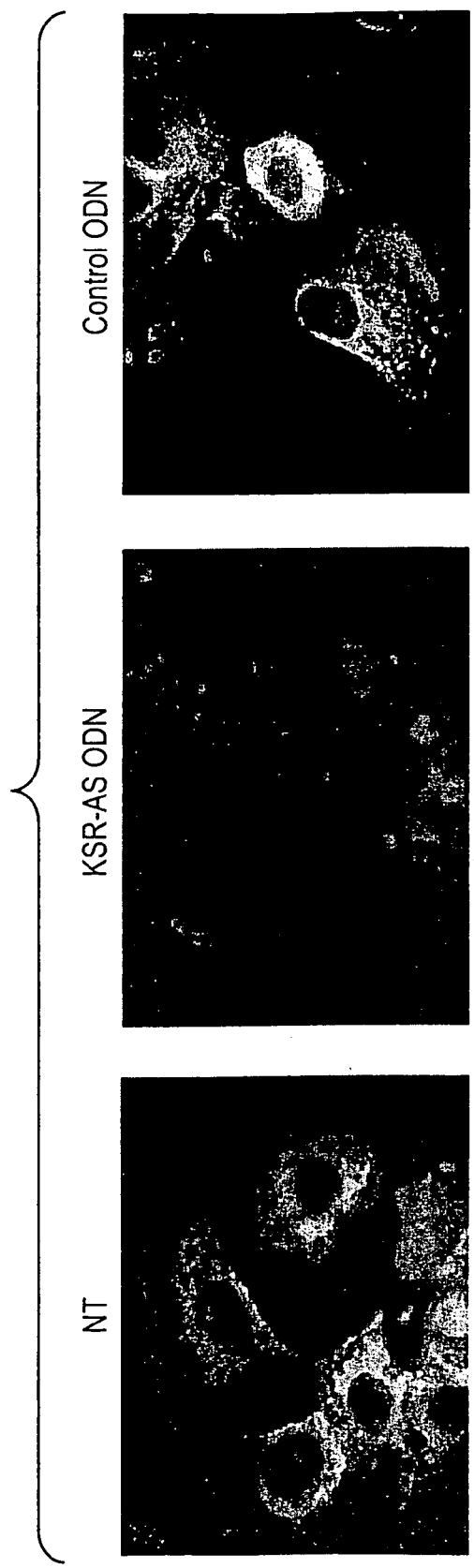

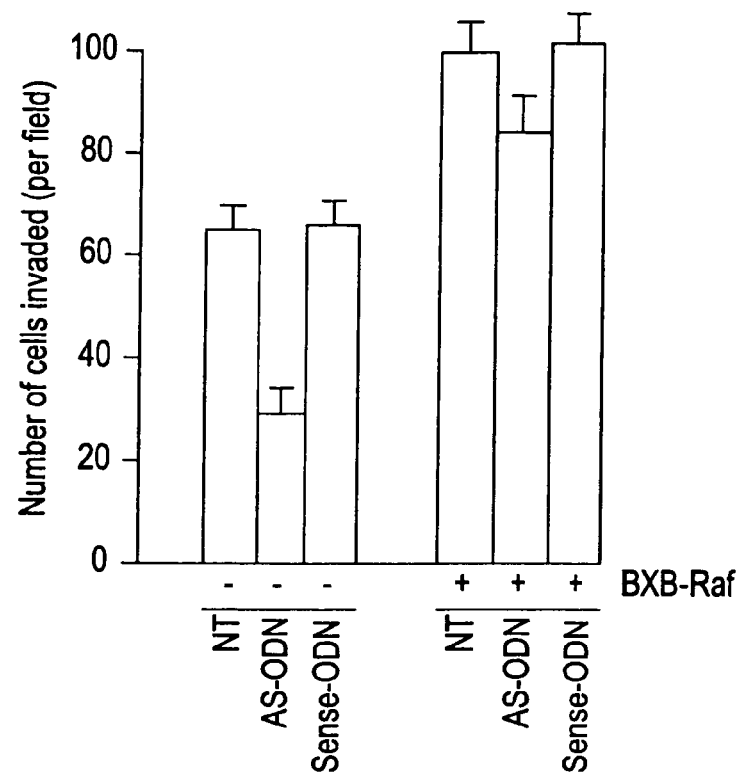
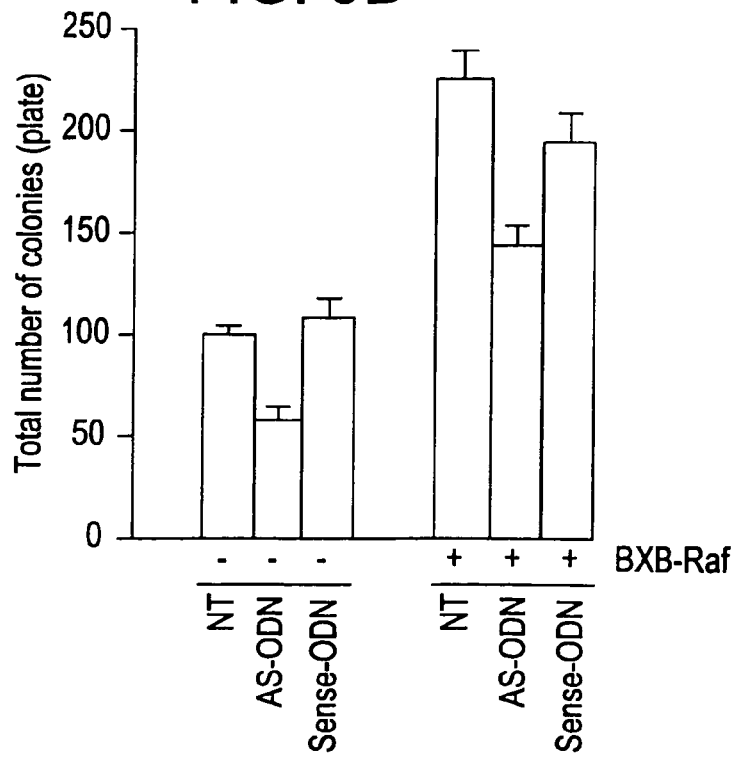

A549 tumor (i) Tumor volume (mm³) vs Days of ODN infusion

- ■ Saline
- ◆ Control-ODN
- ● Sense-ODN
- ▲ AS-ODN (ii) Number of lung metastases foci (whole lung surface)

| Dose of infusion (mg/ kg /Day) | Sense-ODNs | AS-ODN | % inhibition |
|---|---|---|---|
| 10 | 7.4 ± 1.4 | 2.5 ± 0.6 | 65 |
| 25 | 10.2 ± 1.8 | 1.4 ± 0.5 | 86 |

FIG. 11-1

```
Human       MGEK-EGGGGGDAAAAEGGAGAAASRALQQCGQLQ
Mouse  MDRAALRAAA    K         --        V CA1
Human  KLIDISIGSLRGLRTKCAVSNDLTQQEIRTLEAKLVRYICKQRQC
Mouse              S                       K     Q S Human  KLSVAPGERTPELNSYPRFSDWLYTFNVRPEVVQEIPRDLTLDAL
Mouse      I SD  A               I         QE Human  LEMNEAKVKETLRRCGASGDECGRLQYALTCLRKVTGLGGEHKED
Mouse     D   A M     W   TE S   Q                M Human  SSWSSLDARRESGSPSTDTLSAASLPWPPGSSQLGRAGNSAQGP
Mouse   G  I   DS -L   PM M  S-----------    A T →
Human  RSISVSALPASDSPTPSFSEGLSDTCIPLHASGRLTPRALHSFIT
Mouse            V  GL      S         I CA2
Human  PPTTPQLRRHTKLKPPRTPPPPSRKVFQLLPSFPTLTRSKSHESQ
MouseA Human  LGNRIDDVSSMRFDLSHGSPQMVRRDIGLSVTHRFSTKSWLSQVC
Mouse           TP K E P       L CA3
Human  HVCQKSMIFGVKCKHCRLKCHNKCTKEAPACRISFLPLTRLRRTE
Mouse  N                                I   A Human  SVPSDINNPVDRAAEPHFGTLPKALTKKEHPPAMNHLDSSSNPSS
Mouse                                            -

CA4
Human  TTSSTPSSPAPFPTSSNPSSATTPPNPSPGQRDSRFNFPAAYFIH
Mouse           L                       S -------

Human  HRQQFIFPDISAFAHAAPLPEAADGTRLDDQPKADVLEAHEAEAE
Mouse  --------    CSC    SST  S         I   GV Human  EPEAGKSEAEDDED-EVDDLPSSRRPWRGPISRKASQTSVYLQEW
Mouse              ED
```

FIG. 11-2

```
              I                              II
Human  DDIPFEQVELGEPIGQGRWGRVHRGRWHGEVAIRLLEMDGHNQDH
Mouse III              IV                         V
Human  LKLFKKEVMNYRQTRHENVVLFMGACMNPPHLAIITSFCKGRTLH
Mouse VIa         VIb
Human  SFVRDPKTSLDINKTRQIAQEIIKGMGYLHAKGIVHKDLKSKNVF
Mouse VII                       VIII
Human  YDNGKVVITDFGLFGISGVVREERRENQLKLSHDWLCYLAPEIVR
Mouse IX
Human  EMTPGKDEDQLPFSKAADVYAFGTVWYELQARDWPLKNQAAEASI
Mouse    I  R                              F  H  P   L
         X                        XI
Human  WQIGSGEGMKRVLTSVSLGKEVSEILSACWAFDLQERPSFSLLMD
Mouse          VR    A      G Human  MLEKLPKLNRRLSHPGHFWKSAEL
Mouse      R                    DINSSKVMPRFERFGLGTLESGN Mouse  PKM
```

FIG. 12A-1

```
GAATTCCCTC GGGGCTTTCC TGCCGAGGCG CCCGTGTCCC CGGGCTCCTC GCCTCGGCCC
CCAGCGGCCC CGATGCCGAG GCATGGATAG AGCGGCGTTG CGCGCGGCAG CGATGGGCGA
GAAAAGGAG GGCGGCGGCG GGGGCGCCGC GGCGGACGGG GGCGCAGGGG CCGCCGTCAG
CCGGGCGCTG CAGCAGTGCG GCCAGCTGCA GAAGCTCATC GATATCTCCA TCGGCAGTCT
GCGCGGGCTG CGCACCAAGT GCTCAGTGTC TAACGACCTC ACACAGCAGG AGATCCGGAC
CCTAGAGGCA AAGCTGGTGA AATACATTTG CAAGCAGCAG CAGAGCAAGC TTAGTGTGAC
CCCAAGCGAC AGGACCGCCG AGCTAACAG CTACCCACGC TTCAGTGACT GGCTGTACAT
CTTCAACGTG AGGCCTGAGG TGGTGCAGGA GATCCCCAA GAGCTCACAC TGGATGCTCT
GCTGGAGATG GACGAGGCCA AAGCCAAGGA GATGCTGCGG CGCTGGGGGG CCAGCACGGA
GGAGTGCAGC CGCCTACAGC AAGCCCTTAC CTGCCTTCGG AAGGTGACTG GCCTGGGAGG
GGAGCACAAA ATGGACTCAG GTTGGAGTTC AACAGATGCT CGAGACAGTA GCTTGGGGCC
TCCCATGGAC ATGCTTTCCT CGCTGGGCAG AGCGGGTGCC AGCACTCAGG GACCCCGTTC
CATCTCCGTG TCCGCCCTGC CTGCCTCAGA CTCTCCGGTC CCCGGCCTCA GTGAGGGCCT
CTCGGACTCC TGTATCCCCT TGCACACCAG CGGCCGGCTG ACCCCCGGG CCCTGCACAG
CTTCATCACG CCCCCTACCA CACCCCAGCT ACGACGGCAC GCCAAGCTGA AGCCACCAAG
GACACCCCCA CCGCCAAGCC GCAAGGTCTT CCAGCTGCTC CCCAGCTTCC CCACACTCAC
ACGGAGCAAG TCCCACGAGT CCCAGCTGGG AAACCGAATC GACGACGTCA CCCCGATGAA
GTTTGAACTC CCTCATGGAT CCCCACAGCT GGTACGAAGG GATATCGGGC TCTCGGTGAC
GCACAGGTTC TCCACAAAGT CATGGTTGTC ACAGGTGTGC AACGTGTGCC AGAAGAGCAT
GATTTTGGC GTGAAGTGCA AACACTGCAG GTTAAAATGC CATAACAAGT GCACAAAGGA
AGCTCCCGCC TGCAGGATCA CCTTCCTCCC ACTGGCCAGG CTTCGGAGGA CAGAGTCTGT
CCCGTCAGAT ATCAACAACC CAGTGGACAG AGCAGCAGAG CCCCATTTTG GAACCCTTCC
CAAGGCCCTG ACAAAGAAGG AGCACCCTCC AGCCATGAAC CTGGACTCCA GCAGCAACCC
ATCCTCCACC ACGTCCTCCA CACCCTCATC GCCGGCACCT TTCCTGACCT CATCTAATCC
CTCCAGTGCC ACCACGCCTC CCAACCCGTC ACCTGGCCAG CGGGACAGCA GGTTCAGCTT
CCCAGACATT TCAGCCTGTT CTCAGGCAGC CCCGCTGTCC AGCACAGCCG ACAGTACACG
GCTCGACGAC CAGCCCAAAA CAGATGTGCT AGGTGTTCAC GAAGCAGAGG CTGAGGAGCC
TGAGGCTGGC AAGTCAGAGG CAGAGGATGA CGAGGAGGAT GAGGTGGACG ACCTCCCCAG
CTCCCGCCGG CCCTGGAGGG GCCCCATCTC TCGAAAGGCC AGCCAGACCA GCGTTTACCT
GCAAGAGTGG GACATCCCCT TTGAACAGGT GGAACTGGGC GAGCCCATTG ACAGGGTCG
CTGGGGCCGG GTGCACCGAG GCCGTTGGCA TGGCGAGGTG GCCATTCGGC TGCTGGAGAT
GGACGGCCAC AATCAGGACC ACCTGAAGCT GTTCAAGAAA GAGGTGATGA ACTACCGGCA
GACGCGGCAT GAGAACGTGG TGCTCTTCAT GGGGGCCTGC ATGAACCCAC CTCACCTGGC
CATTATCACC AGCTTCTGCA AGGGGCGGAC ATTGCATTCA TTCGTGAGGG ACCCCAAGAC
GTCTCTGGAC ATCAATAAGA CTAGGCAGAT CGCCCAGGAG ATCATCAAGG CATGGGTTA
TCTTCATGCA AAAGGCATCG TGCACAAGGA CCTCAAGTCC AAGAATGTCT TCTATGACAA
CGGCAAAGTG GTCATCACAG ACTTCGGGCT GTTTGGGATC TCGGGTGTGG TCCGAGAGGA
ACGGCGCGAG AACCAACTGA AACTGTCACA TGACTGGCTG TGCTACCTGG CCCCAGAGAT
CGTACGAGAA ATGATCCCGG GCGGGACGA GGACCAGCTG CCCTTCTCCA AAGCAGCCGA
TGTCTATGCA TTCGGGACTG TGTGGTATGA ACTACAGGCA AGAGACTGGC CCTTTAAGCA
CCAGCCTGCT GAGGCCTTGA TCTGGCAGAT TGGAAGTGGG GAAGGAGTAC GGCGCGTCCT
GGCATCCGTC AGCCTGGGGA AGGAAGTCGG CGAGATCCTG TCTGCCTGCT GGGCTTTCGA
TCTGCAGGAG AGACCCAGCT TCAGCCTGCT GATGGACATG CTGGAGAGGC TGCCCAAGCT
GAACCGGCGG CTCTCCCACC CTGGGCACTT TTGGAAGTCG GCTGACATTA ACAGCAGCAA
AGTCATGCCC CGCTTTGAAA GGTTTGGCCT GGGGACCCTG GAGTCCGGTA ATCCAAAGAT
```

FIG. 12A-2

```
GTAGCCAGCC CTGCACGTTC ATGCAGAGAG TGTCTTCCTT TCGAAAACAT GATCACGAAA
CATGCAGACC ACCACCTCAA GGAATCAGAA GCATTGCATC CCAAGCTGCG GACTGGGAGC
GTGTCTCCTC CCTAAAGGAC GTGCGTGCGT GCGTGCGTGC GTGCGTGCGT GCGTGCGTCA
CCAAGGTGTG TGGAGCTCAG GATCGCAGCC ATACACGCAA CTCCAGATGA TACCACTACC
GCCAGTGTTT ACACAGAGGT TTCTGCCTGG CAAGCTTGGT ATTTTACAGT AGGTGAAGAT
CATTCTGCAG AAGGGTGCTG GCACAGTGGA GCAGCACGGA TGTCCCCAGC CCCCGTTCTG
GAAGACCCTA CAGCTGTGAG AGGCCCAGGG TTGAGCCAGA TGAAAGAAAA GCTGCGTGGG
TGTGGGCTGT ACCCGGAAAA GGGCAGGTGG CAGGAGGTTT GCCTTGGCCT GTGCTTGGGC
CGAGAACCAC ACTAAGGAGC AGCAGCCTGA GTTAGGAATC TATCTGGATT ACGGGGATCA
GAGTTCCTGG AGAGTGGACT CAGTTTCTGC TCTGATCCAG GCCTGTTGTG CTTTTTTTTT
TTCCCCCTTA AAAAAAAAAA AGTACAGACA GAATCTCAGC GGCTTCTAGA CTGATCTGAT
GGATCTTAGC CCGGCTTCTA CTGCGGGGGG GAGGGGGGGA GGGATAGCCA CATATCTGTG
GAGACACCCA CTTCTTTATC TGAGGCCTCC AGGTAGGCAC AAAGGCTGTG GAACTCAGCC
TCTATCATCA GACACCCCCC CCCAATGCCT CATTGACCCC CTTCCCCCAG AGCCAAGGGC
TAGCCCATCG GGTGTGTGTA CAGTAAGTTC TTGGTGAAGG AGAACAGGGA CGTTGGCAGA
AGCAGTTTGC AGTGGCCCTA GCATCTTAAA ACCCATTGTC TGTCACACCA GAAGGTTCTA
GACCTACCAC CACTTCCCTT CCCCATCTCA TGGAAACCTT TTAGCCCATT CTGACCCCTG
TGTGTGCTCT GAGCTCAGAT CGGGTTATGA GACCGCCCAG GCACATCAGT CAGGGAGGCT
CTGATGTGAG CCGCAGACCT CTGTGTTCAT TCCTATGAGC TGGAGGGGCT GGACTGGGTG
GGGTCAGATG TGCTTGGCAG GAACTGTCAG CTGCTGAGCA GGGTGGTCCC TGAGCGGAGG
ATAAGCAGCA TCAGACTCCA CAACCAGAGG AAGAAAGAAA TGGGGATGGA GCGGAGACCC
ACGGGCTGAG TCCCGCTGTG GAGTGGCCTT GCAGCTCCCT CTCAGTTAAA ACTCCCAGTA
AAGCCACAGT TCTCCGAGCA CCCAAGTCTG CTCCAGCCGT CTCTTAAAAC AGGCCACTCT
CTGAGAAGGA ATTC
```

FIG. 12B-1

```
GCGAAGCTGG TCCGTTACAT TTGTAAGCAG AGGCAGTGCA AGCTGAGCGT GGCTCCCGGT
GAGAGGACCC CAGAGCTCAA CAGCTACCCC CGCTTCAGCG ACTGGCTGTA CACTTTCAAC
GTGAGGCCGG AGGTGGTGCA GGAGATCCCC CGAGACCTCA CGCTGGATGC CCTGCTGGAG
ATGAATGAGG CCAAGGTGAA GGAGACGCTG CGGCGCTGTG GGGCCAGCGG GGATGAGTGT
GGCCGTCTGC AGTATGCCCT CACCTGCCTG CGGAAGGTGA CAGGCCTGGC TTCATCACCC
CGCCCACCAC ACCCCAGCTG CGACGGCACA CCAAGCTGAA GCCACCACGG ACGCCCCCC
CACCCAGCCG CAAGGTCTTC CAGCTGCTGC CCAGCTTCCC CACACTCACC CGGAGCAAGT
CCCATGAGTC TCAGCTGGGG AACCGCATTG ATGACGTCTC CTCGATGAGG TGAGTTGGGA
GCACGTTCCT GCACGTGGCT ATGCTGTGGG GCCTCTCTCA TGAGTCAGAG CGGAGGGAGA
CAGCTGTGCC TCTGGAGTCT GCTTTTAATT GTCTGGAAAT GCAGAGATGT CTGGTTTTTG
CCTGAGCAAA ATAGGAGTTT ATTTTTGTAC TATCCCGAGC TGGCTAAGGA GAGTCACGTA
GCTGTGGGCG GGGTCTTGGG GATGAGGAGG GGTACAGCAG GCAGGGACTA TGCTGAAGTG
GAGCTGGCTG TAGGAACCCC AGGGAGGCAC AGGGGGAGCA TGAAGAGGAG CTACACTTCC
CTCCCTTAGT GCCCGGGCAG AAACTCCAG GGCCCTTCAC AGAACCTTGG AGGAACATTC
AACACCCCCA TCTCTAGGAC AGCCCCAGCC TTGTCATCCT CCAATTGCTG TGGTAACACG
GGGACTGGAG CAGTGAGATT ATTAGGCCTT CAGGGCCAGT GTCTCCATGC AGATCAGATG
GAGGCGGTGC TTGGCACATA CACCACCTCA CTGCCCATGC CCCCAGAAGT TGGTGCAGAT
CATAAGGTGG CTTTTGGGGC TAATTGATTG AAGTTCCAAC ATAGTCTGTT TCTCCTAGGC
TGGTAGCTGG CACCTTTGGC CCCATGTGTT TTTTAATTAT TTTTTCTTTT GAGACGAAAT
CTCGCTCTAT CACCCAGGCT GAAGTGCAGT AGTGCAATCT CAGCTCACTG CAGCCTCTGC
CTCCCGGGTT CAAGCAATTC TCCTGCCTCA GCCTCCCGAG TAGCCAGGAT TAAAGGTGCC
TGCCACCACA CATGGCTAAT TTTTGTATTT TTAATAGAGA CGGGGTTTCA CCATGTTAGC
CAGGCTGGTC TCAAACTCCT GACCTCAGGT GATCTTCCTG CCTCAGCCTC CAAAGTGCT
GGGATTACAG GTGTGAGCCA CTGCGCCCAG TCATGCCCAT GTGTTTTGGT GGTCTTGGCT
GCTGATGGGT GGGGTGAGCC CCAGGAGGAA GTTGGGACAA GTCAACCTCA TGGCAGATGT
GCCAGGGAGA GCTGCGGGTG AGATAGATTG TTCCTATCCC CCTCTCCTTG ATGTGGGAGG
ACTCAGTACC TCCAGCACAC CCTTCTCATG GAGGTTGGTT ATGTGGTACT TGGCCTCAAG
TGAACCAGCA CTTCATGAGT CCAGCTTTGT GCTAGACCAG CACTTGGGAT TGAGGGGGC
AGTGGCCACC CTCGGGGAC CTTCTGACTC AGAGGACATG AGATGGCCAC ACTCGAGCAC
TGTGTTCCTG ACCTTCTGG GTCACAGGTC ACCTTGATGA TTGGATGAAA GTCTTAGATC
TTCTTTCCAG AGAAAGTCT ACAACATTCT ACTGAACCAG TCCAGAGGGT TCCCGGACCC
CCGAAGCCCA CCCATGGGCT GGCTCTGGGA GGCAATGGCG CTGAGTATGG GGGCATCTCT
CGCATGGATC CCCACAGATG GTACGGAGGG ATATCGGGCT GTCGGTGACG CACAGGTTCT
CCACCAAGTC CTGGCTGTCG CAGGTCTGCC ACGTGTGCCA GAAGAGCATG ATATTTGGAG
TGAAGTGCAA GCATTGCAGG TTGAAGTGTC ACAACAAATG TACCAAAGAA GCCCCTGCCT
GTAGAATATC CTTCCTGCCA CTAACTCGGC TTCGGAGGAC AGAATCTGTC CCCTCGGACA
TCAACAACCC GGTGGACAGA GCAGCCGAAC CCCATTTTGG AACCCTCCCC AAAGCACTGA
CAAAGAAGGA GCACCCTCCG GCCATGAATC ACCTGGACTC CAGCAGCAAC CCTTCCTCCA
CCACCTCCTC CACACCCTCC TCACCGGCGC CCTTCCCGAC ATCATCCAAC CCATCCAGCG
```

FIG. 12B-2

```
CCACCACGCC CCCCAACCCC TCACCTGGCC AGCGGGACAG CAGGTTCAAC TTCCCAGCTG
CCTACTTCAT TCATCATAGA CAGCAGTTTA TCTTTCCAGA CATTTCAGCC TTTGCACACG
CAGCCCCGCT CCCTGAAGCT GCCGACGGTA CCCGGCTCGA TGACCAGCCG AAAGCAGATG
TGTTGGAAGC TCACGAAGCG GAGGCTGAGG AGCCAGAGGC TGGCAAGTCA GAGGCAGAAG
ACGATGAGGA CGAGGTGGAC GACTTGCCGA GCTCTCGCCG GCCCTGGCGG GGCCCCATCT
CTCGCAAGGC CAGCCAGACC AGCGTGTACC TGCAGGAGTG GGACATCCCC TTCGAGCAGG
TAGAGCTGGG CGAGCCCATC GGGCAGGGCC GCTGGGGCCG GGTGCACCGC GGCCGCTGGC
ATGGCGAGGT GGCCATTCGC CTGCTGGAGA TGGACGGCCA CAACCAGGAC CACCTGAAGC
TCTTCAAGAA AGAGGTGATG AACTACCGGC AGACGCGGCA TGAGAACGTG GTGCTCTTCA
TGGGGGCCTG CATGAACCCG CCCCACCTGG CCATTATCAC CAGCTTCTGC AAGGGGCGGA
CGTTGCACTC GTTTGTGAGG GACCCCAAGA CGTCTCTGGA CATCAACAAG ACGAGGCAAA
TCGCTCAGGA GATCATCAAG GGCATGGATA TCTTCATGC CAAGGGCATC GTACACAAAG
ATCTCAAATC TAAGAACGTC TTCTATGACA ACGGCAAGGT GGTCATCACA GACTTCGGGC
TGTTTGGGAT CTCAGGCGTG GTCCGAGAGG GACGGCGTGA GAACCAGCTA AAGCTGTCCC
ACGACTGGCT GTGCTATCTG GCCCCTGAGA TTGTACGCGA GATGACCCCC GGGAAGGACG
AGGATCAGCT GCCATTCTCC AAAGCTGCTG ATGTCTATGC ATTTGGGACT GTTTGGTATG
AGCTGCAAGC AAGAGACTGG CCCTTGAAGA ACCAGCTGC AGAGGCATCC ATCTGGCAGA
TTGGAAGCGG GGAAGGAATG AAGCGTGTCC TGACTTCTGT CAGCTTGGGG AAGGAAGTCA
GTGAGATCCT GTCGGCCTGC TGGGCTTTCG ACCTGCAGGA GAGACCCAGC TTCAGCCTGC
TGATGGACAT GCTGGAGAAA CTTCCCAAGC TGAACCGGCG GCTCTCCCAC CCTGGACACT
TCTGGAAGTC AGCTGAGTTG TAGGCCTGGC TGCCTTGCAT GCACCAGGGG CTTTCTTCCT
CCTAATCAAC AACTCAGCAC CGTGACTTCT GCTAAAATGC AAAATGAGAT GCGGGCACTA
ACCCAGGGGA TGCCACCTCT GCTGCTCCAG TCGTCTCTCT CGAGGCTACT TCTTTTGCTT
TGTTTTAAAA ACTGGCCCTC TGCCCTCTCC ACGTGGCCTG CATATGCCCA AG
```

FIGURE 14

```
atgggagaga aggagggcgg tggcggggggg gatgcggcgg ccgcggaggg tggcgcaggg
gccgcggcca gccgggcgct gcagcagtgt gggcagctcc agaagctcat cgacatctcc
atcggcagtc tgcgcgggct gcgcaccaag tgcgcagtgt ctaacgacct cacccagcag
gagatacgga ccctagaggc aaagctggtc cgttacattt gtaagcagag gcagtgcaag
ctgagcgtgg ctcccggtga gaggacccca gagctcaaca gctaccccg cttcagcgac
tggctgtaca ctttcaacgt gaggccggag gtggtgcagg atcccccg agacctacg
ctggatgccc tgctggagat gaatgaggcc aaggtgaagg agacgctgcg gcgctgtggg
gccagcgggg atgagtgtgg ccgtctgcag tatgccctca cctgcctgcg gaaggtgaca
ggcctgggag gggagcacaa ggaggactcc agttggagtt cattggatgc gcggcgggaa
agtggctcag ggccttccac ggacaccctc tcagcagcca gcctgccctg gccccaggg
agctcccagc tgggcagagc aggcaacagc gcccagggcc cacgctccat ctccgtgtca
gctctgcccg cctcagactc ccccacccccc agcttcagtg agggcctctc agacacctgt
attcccctgc acgccagcgg ccggctgacc ccccgtgccc tgcacagctt catcaccccg
cccaccacac cccagctgcg acggcacacc aagctgaagc caccacggac gccccccca
cccagccgca aggtcttcca gctgctgccc agcttcccca cactcacccg gagcaagtcc
catgagtctc agctggggaa ccgcattgat gacgtctcct cgatgaggtt tgatctctcg
catggatccc cacagatggt acggagggat atcgggctgt cggtgacgca caggttctcc
accaagtcct ggctgtcgca ggtctgccac gtgtgccaga agagcatgat atttggagtg
aagtgcaagc attgcaggtt gaagtgtcac aacaaatgta ccaaagaagc ccctgcctgt
agaatatcct tcctgccact aactcggctt cggaggacag aatctgtccc ctcggacatc
aacaacccgg tggacagagc agccgaaccc cattttggaa ccctccccaa agcactgaca
aagaaggagc accctccggc catgaatcac ctggactcca gcagcaaccc ttcctccacc
acctcctcca caccctcctc accggcgccc ttcccgacat catccaaccc atccagcgcc
accacgcccc caacccctc acctggccag cgggacagca ggttcaactt cccagctgcc
tacttcattc atcatagaca gcagtttatc tttccagaca tttcagcctt tgcacacgca
gccccgctcc ctgaagctgc cgacggtacc cggctcgatg accagccgaa agcagatgtg
ttggaagctc acgaagcgga ggctgaggag ccagaggctg gcaagtcaga ggcagaagac
gatgaggacg aggtggacga cttgccgagc tctcgccggc cctggcgggg ccccatctct
cgcaaggcca gccagaccag cgtgtacctg caggagtggg acatcccctt cgagcaggta
gagctgggcg agcccatcgg gcagggccgc tggggccggg tgcaccgcgg ccgctggcat
ggcgaggtgg ccattcgcct gctggagatg gacggccaca accaggacca cctgaagctc
ttcaagaaag aggtgatgaa ctaccggcag acgcggcatg agaacgtggt gctcttcatg
ggggcctgca tgaacccgcc ccacctggcc attatcacca gcttctgcaa ggggcggacg
ttgcactcgt ttgtgaggga cccaagacg tctctggaca tcaacaagac gaggcaaatc
gctcaggaga tcatcaaggg catgggatat cttcatgcca agggcatcgt acacaaagat
ctcaaatcta agaacgtctt ctatgacaac ggcaaggtgg tcatcacaga cttcgggctg
tttgggatct caggcgtggt ccgagaggga cggcgtgaga accagctaaa gctgtcccac
gactggctgt gctatctggc ccctgagatt gtacgcgaga tgacccccgg gaaggacgag
gatcagctgc cattctccaa agctgctgat gtctatgcat tgggactgt ttggtatgag
ctgcaagcaa gagactggcc cttgaagaac caggctgcag aggcatccat ctggcagatt
ggaagcgggg aaggaatgaa gcgtgtcctg acttctgtca gcttggggaa ggaagtcagt
gagatcctgt cggcctgctg ggctttcgac ctgcaggaga gacccagctt .cagcctgctg
atggacatgc tggagaaact tcccaagctg aaccggcggc tctcccaccc tggacacttc
tggaagtcag ctgagttgta g
```

FIGURE 15

```
atgggagagaaggagggcggtggcggggggatgcggcggccgcggagggtggcgcaggg
 M  G  E  K  E  G  G  G  G  D  A  A  A  A  E  G  G  A  G gccgcggccagccgggcgctgcagcagtgtgggcagctccagaagctcatcgacatctcc
 A  A  A  S  R  A  L  Q  Q  C  G  Q  L  Q  K  L  I  D  I  S
                                     ─────────────────────────
                                           CA1 (32-72)
atcggcagtctgcgcgggctgcgcaccaagtgcgcagtgtctaacgacctcacccagcag
 I  G  S  L  R  G  L  R  T  K  C  A  V  S  N  D  L  T  Q  Q
─────────────────────                 ─────────────────────
   AS-ODN3(42-47)                        AS-ODN2(52-57)
gagatacggaccctagaggcaaagctggtccgttacatttgtaagcagaggcagtgcaag
 E  I  R  T  L  E  A  K  L  V  R  Y  I  C  K  Q  R  Q  C  K
─────────────────────────────────────
         AS-ODN1(63-68)
ctgagcgtggctcccggtgagaggaccccagagctcaacagctaccccgcttcagcgac
 L  S  V  A  P  G  E  R  T  P  E  L  N  S  Y  P  R  F  S  D tggctgtacactttcaacgtgaggccggaggtggtgcaggagatcccccgagacctcacg
 W  L  Y  T  F  N  V  R  P  E  V  V  Q  E  I  P  R  D  L  T ctggatgccctgctggagatgaatgaggccaaggtgaaggagacgctgcggcgctgtggg
 L  D  A  L  L  E  M  N  E  A  K  V  K  E  T  L  R  R  C  G gccagcggggatgagtgtggccgtctgcagtatgccctcacctgcctgcggaaggtgaca
 A  S  G  D  E  C  G  R  L  Q  Y  A  L  T  C  L  R  K  V  T ggcctgggaggggagcacaaggaggactccagttggagttcattggatgcgcggcgggaa
 G  L  G  G  E  H  K  E  D  S  S  W  S  S  L  D  A  R  R  E agtggctcagggccttccacggacaccctctcagcagccagcctgccctggcccccaggg
 S  G  S  G  P  S  T  D  T  L  S  A  A  S  L  P  W  P  P  G agctcccagctgggcagagcaggcaacagcgcccagggcccacgctccatctccgtgtca
 S  S  Q  L  G  R  A  G  N  S  A  Q  G  P  R  S  I  S  V  S gctctgcccgcctcagactcccccacccccagcttcagtgagggcctctcagacacctgt
 A  L  P  A  S  D  S  P  T  P  S  F  S  E  G  L  S  D  T  C attcccctgcacgccagcggccggctgaccccccgtgccctgcacagcttcatcaccccg
 I  P  L  H  A  S  G  R  L  T  P  R  A  L  H  S  F  I  T  P cccaccacaccccagctgcgacggcacaccaagctgaagccaccacggacgccccccca
 P  T  T  P  Q  L  R  R  H  T  K  L  K  P  P  R  T  P  P  P
                                                 ─────────────
cccagccgcaaggtcttccagctgctgcccagcttccccacactcacccggagcaagtcc
 P  S  R  K  V  F  Q  L  L  P  S  F  P  T  L  T  R  S  K  S
─────────────────────────
     CA2 (277-289)
catgagtctcagctggggaaccgcattgatgacgtctcctcgatgaggtttgatctctcg
 H  E  S  Q  L  G  N  R  I  D  D  V  S  S  M  R  F  D  L  S catggatccccacagatggtacggagggatatcgggctgtcggtgacgcacaggttctcc
 H  G  S  P  Q  M. V  R  R  D  I  G  L  S  V  T  H  R  F  S
                                              ────────────────
accaagtcctggctgtcgcaggtctgccacgtgtgccagaagagcatgatatttggagtg
 T  K  S  W  L  S  Q  V  C  H  V  C  Q  K  S  M  I  F  G  V
─────────────────────────────────────────────────────────────
                         CA3 (335-380)
aagtgcaagcattgcaggttgaagtgtcacaacaaatgtaccaaagaagcccctgcctgt
 K  C  K  H  C  R  L  K  C  H  N  K  C  T  K  E  A  P  A  C
```

FIGURE 15 (cont'd)

```
agaatatccttcctgccactaactcggcttcggaggacagaatctgtcccctcggacatc
 R   I   S   F   L   P   L   T   R   L   R   R   T   E   S   V   P   S   D   I aacaacccggtggacagagcagccgaaccccattttggaaccctccccaaagcactgaca
 N   N   P   V   D   R   A   A   E   P   H   F   G   T   L   P   K   A   L   T aagaaggagcaccctccggccatgaatcacctggactccagcagcaaccccttcctccacc
 K   K   E   H   P   P   A   M   N   H   L   D   S   S   S   N   P   S   S   T
                                           _____ acctcctccacaccctcctcaccggcgcccttcccgacatcatccaacccatccagcgcc
 T   S   S   T   P   S   S   P   A   P   F   P   T   S   S   N   P   S   S   A
_____
                          CA4 (432-498)
accacgccccccaacccctcacctggccagcgggacagcaggttcaacttcccagctgcc
 T   T   P   P   N   P   S   P   G   Q   R   D   S   R   F   N   F   P   A   A
_____ tacttcattcatcatagacagcagtttatctttccagacatttcagcctttgcacacgca
 Y   F   I   H   H   R   Q   Q   F   I   F   P   D   I   S   A   F   A   H   A
_____ gccccgctccctgaagctgccgacggtacccggctcgatgaccagccgaaagcagatgtg
 A   P   L   P   E   A   A   D   G   T   R   L   D   D   Q   P   K   A   D   V ttggaagctcacgaagcggaggctgaggagccagaggctggcaagtcagaggcagaagac
 L   E   A   H   E   A   E   A   E   E   P   E   A   G   K   S   E   A   E   D gatgaggacgaggtggacgacttgccgagctctcgccggccctggcggggccccatctct
 D   E   D   E   V   D   D   L   P   S   S   R   R   P   W   R   G   P   I   S cgcaaggccagccagaccagcgtgtacctgcaggagtgggacatccccttcgagcaggta
 R   K   A   S   Q   T   S   V   Y   L   Q   E   W   D   I   P   F   E   Q   V
                _____ gagctgggcgagcccatcgggcagggccgctggggccgggtgcaccgcggccgctggcat
 E   L   G   E   P   I   G   Q   G   R   W   G   R   V   H   R   G   R   W   H
_____
       CA5 (565-836, consisting of 11 conserved subdomains)
ggcgaggtggccattcgcctgctggagatggacggccacaaccaggaccacctgaagctc
 G   E   V   A   I   R   L   L   E   M   D   G   H   N   Q   D   H   L   K   L
_____ ttcaagaaagaggtgatgaactaccggcagacgcggcatgagaacgtggtgctcttcatg
 F   K   K   E   V   M   N   Y   R   Q   T   R   H   E   N   V   V   L   F   M
_____ ggggcctgcatgaacccgccccacctggccattatcaccagcttctgcaaggggcggacg
 G   A   C   M   N   P   P   H   L   A   I   I   T   S   F   C   K   G   R   T
_____ ttgcactcgtttgtgagggaccccaagacgtctctggacatcaacaagacgaggcaaatc
 L   H   S   F   V   R   D   P   K   T   S   L   D   I   N   K   T   R   Q   I
_____ gctcaggagatcatcaagggcatgggatatcttcatgccaagggcatcgtacacaaagat
 A   Q   E   I   I   K   G   M   G   Y   L   H   A   K   G   I   V   H   K   D
_____ ctcaaatctaagaacgtcttctatgacaacggcaaggtggtcatcacagacttcgggctg
 L   K   S   K   N   V   F   Y   D   N   G   K   V   V   I   T   D   F   G   L
_____ tttgggatctcaggcgtggtccgagagggacggcgtgagaaccagctaaagctgtcccac
 F   G   I   S   G   V   V   R   E   G   R   R   E   N   Q   L   K   L   S   H
_____ gactggctgtgctatctggcccctgagattgtacgcgagatgaccccggggaaggacgag
 D   W   L   C   Y   L   A   P   E   I   V   R   E   M   T   P   G   K   D   E
_____
```

FIGURE 15 (cont'd)

```
gatcagctgccattctccaaagctgctgatgtctatgcatttgggactgtttggtatgag
 D   Q   L   P   F   S   K   A   A   D   V   Y   A   F   G   T   V   W   Y   E ctgcaagcaagagactggcccttgaagaaccaggctgcagaggcatccatctggcagatt
 L   Q   A   R   D   W   P   L   K   N   Q   A   A   E   A   S   I   W   Q   I ggaagcggggaaggaatgaagcgtgtcctgacttctgtcagcttggggaaggaagtcagt
 G   S   G   E   G   M   K   R   V   L   T   S   V   S   L   G   K   E   V   S gagatcctgtcggcctgctgggctttcgacctgcaggagagacccagcttcagcctgctg
 E   I   L   S   A   C   W   A   F   D   L   Q   E   R   P   S   F   S   L   L atggacatgctggagaaacttcccaagctgaaccggcggctctcccaccctggacacttc
 M   D   M   L   E   K   L   P   K   L   N   R   R   L   S   H   P   G   H   F tggaagtcagctgagttgtag
 W   K   S   A   E   L   -
```

FIGURE 16

```
Atggatagagcggcgttgcgcgcggcagcgatgggcgagaaaaaggagggcggcggcggg
 M  D  R  A  A  L  R  A  A  A  M  G  E  K  K  E  G  G  G  G Ggcgccgcggcggacggggggcgcaggggccgccgtcagccgggcgctgcagcagtgcggc
 G  A  A  A  D  G  G  A  G  A  A  V  S  R  A  L  Q  Q  C  G Cagctgcagaagctcatcgatatctccatcggcagtctgcgcgggctgcgcaccaagtgc
 Q  L  Q  K  L  I  D  I  S  I  G  S  L  R  G  L  R  T  K  C   60
       CA1 (42-81)              AS-ODN3(51-56)

tcagtgtctaacgaccccacacagcaggagatccggaccctagaggcaaagctggtgaaa
 S  V  S  N  D  L  T  Q  Q  E  I  R  T  L  E  A  K  L  V  K   80
   AS-ODN2(61-66)                       AS-ODN1(72-77)

tacatttgcaagcagcagcagagcaagcttagtgtgaccccaagcgacaggaccgccgag
 Y  I  C  K  Q  Q  Q  S  K  L  S  V  T  P  S  D  R  T  A  E ctcaacagctacccacgcttcagtgactggctgtacatcttcaacgtgaggcctgaggtg
 L  N  S  Y  P  R  F  S  D  W  L  Y  I  F  N  V  R  P  E  V gtgcaggagatcccccaagagctcacactggatgctctgctggagatggacgaggccaaa
 V  Q  E  I  P  Q  E  L  T  L  D  A  L  L  E  M  D  E  A  K gccaaggagatgctgcggcgctgggggggccagcacggaggagtgcagccgcctacagcaa
 A  K  E  M  L  R  R  W  G  A  S  T  E  E  C  S  R  L  Q  Q gcccttacctgccttcggaaggtgactggcctggggagggagcacaaaatggactcaggt
 A  L  T  C  L  R  K  V  T  G  L  G  G  E  H  K  M  D  S  G tggagttcaacagatgctcgagacagtagcttggggcctcccatggacatgctttcctcg
 W  S  S  T  D  A  R  D  S  S  L  G  P  P  M  D  M  L  S  S ctgggcagagcgggtgccagcactcagggaccccgttccatctccgtgtccgccctgcct
 L  G  R  A  G  A  S  T  Q  G  P  R  S  I  S  V  S  A  L  P gcctcagactctccggtccccggcctcagtgagggcctctcggactcctgtatcccctttg
 A  S  D  S  P  V  P  G  L  S  E  G  L  S  D  S  C  I  P  L cacaccagcggccggctgaccccccgggccctgcacagcttcatcacgccccctaccaca
 H  T  S  G  R  L  T  P  R  A  L  H  S  F  I  T  P  P  T  T ccccagctacgacggcacgccaagctgaagccaccaaggacaccccaccgccaagccgc
 P  Q  L  R  R  H  A  K  L  K  P  P  R  T  P  P  P  P  S  R
                                        CA2 (274-286)

aaggtcttccagctgctccccagcttccccacactcacacggagcaagtcccacgagtcc
 K  V  F  Q  L  L  P  S  F  P  T  L  T  R  S  K  S  H  E  S cagctgggaaaccgaatcgacgacgtcaccccgatgaagtttgaactccctcatggatcc
 Q  L  G  N  R  I  D  D  V  T  P  M  K  F  E  L  P  H  G  S ccacagctggtacgaagggatatcgggctctcggtgacgcacaggttctccacaaagtca
 P  Q  L  V  R  R  D  I  G  L  S  V  T  H  R  F  S  T  K  S tggttgtcacaggtgtgcaacgtgtgccagaagagcatgatttttggcgtgaagtgcaaa
 W  L  S  Q  V  C  N  V  C  Q  K  S  M  I  F  G  V  K  C  K
                              CA3 (331-377)
```

FIGURE 16 (cont'd)

```
cactgcaggttaaaatgccataacaagtgcacaaaggaagctcccgcctgcaggatcacc
 H  C  R  L  K  C  H  N  K  C  T  K  E  A  P  A  C  R  I  T ttcctcccactggccaggcttcggaggacagagtctgtcccgtcagatatcaacaaccca
 F  L  P  L  A  R  L  R  R  T  E  S  V  P  S  D  I  N  N  P gtggacagagcagcagagccccatttggaacccttcccaaggccctgacaagaaggag
 V  D  R  A  A  E  P  H  F  G  T  L  P  K  A  L  T  K  K  E caccctccagccatgaacctggactccagcagcaacccatcctccaccacgtcctccaca
 H  P  P  A  M  N  L  D  S  S  S  N  P  S  S  T  T  S  S  T ccctcatcgccggcacctttcctgacctcatctaatccctccagtgccaccacgcctccc
 P  S  S  P  A  P  F  L  T  S  S  N  P  S  S  A  T  T  P  P
                    CA4 (428-480)
aacccgtcacctggccagcgggacagcaggttcagcttcccagacatttcagcctgttct
 N  P  S  P  G  Q  R  D  S  R  F  S  F  P  D  I  S  A  C  S caggcagccccgctgtccagcacagccgacagtacacggctcgacgaccagcccaaaaca
 Q  A  A  P  L  S  S  T  A  D  S  T  R  L  D  D  Q  P  K  T gatgtgctaggtgttcacgaagcagaggctgaggagcctgaggctggcaagtcagaggca
 D  V  L  G  V  H  E  A  E  A  E  E  P  E  A  G  K  S  E  A gaggatgacgaggaggatgaggtggacgacctccccagctcccgccggccctggaggggc
 E  D  D  E  E  D  E  V  D  D  L  P  S  S  R  R  P  W  R  G cccatctctcgaaaggccagccagaccagcgtttacctgcaagagtgggacatcccctt
 P  I  S  R  K  A  S  Q  T  S  V  Y  L  Q  E  W  D  I  P  F gaacaggtggaactgggcgagcccattggacagggtcgctggggccgggtgcaccgaggc
 E  Q  V  E  L  G  E  P  I  G  Q  G  R  W  G  R  V  H  R  G
      CA5 (548-819, consisting of 11 conserved subdomains)
cgttggcatggcgaggtggccattcggctgctggagatggacggccacaatcaggaccac
 R  W  H  G  E  V  A  I  R  L  L  E  M  D  G  H  N  Q  D  H ctgaagctgttcaagaaagaggtgatgaactaccggcagacgcggcatgagaacgtggtg
 L  K  L  F  K  K  E  V  M  N  Y  R  Q  T  R  H  E  N  V  V ctcttcatgggggcctgcatgaacccacctcacctggccattatcaccagcttctgcaag
 L  F  M  G  A  C  M  N  P  P  H  L  A  I  I  T  S  F  C  K gggcggacattgcattcattcgtgagggaccccaagacgtctctggacatcaataagact
 G  R  T  L  H  S  F  V  R  D  P  K  T  S  L  D  I  N  K  T aggcagatcgcccaggagatcatcaagggcatgggttatcttcatgcaaaaggcatcgtg
 R  Q  I  A  Q  E  I  I  K  G  M  G  Y  L  H  A  K  G  I  V cacaaggacctcaagtccaagaatgtcttctatgacaacggcaaagtggtcatcacagac
 H  K  D  L  K  S  K  N  V  F  Y  D  N  G  K  V  V  I  T  D ttcgggctgtttgggatctcgggtgtggtccgagaggaacggcgcgagaaccaactgaaa
 F  G  L  F  G  I  S  G  V  V  R  E  E  R  R  E  N  Q  L  K ctgtcacatgactggctgtgctacctggcccccgagatcgtacgagaaatgatcccgggg
 L  S  H  D  W  L  C  Y  L  A  P  E  I  V  R  E  M  I  P  G
```

FIGURE 16 (cont'd)

```
cgggacgaggaccagctgcccttctccaaagcagccgatgtctatgcattcgggactgtg
 R   D   E   D   Q   L   P   F   S   K   A   A   D   V   Y   A   F   G   T   V tggtatgaactacaggcaagagactggccctttaagcaccagcctgctgaggccttgatc
 W   Y   E   L   Q   A   R   D   W   P   F   K   H   Q   P   A   E   A   L   I tggcagattggaagtggggaaggagtacggcgcgtcctggcatccgtcagcctggggaag
 W   Q   I   G   S   G   E   G   V   R   R   V   L   A   S   V   S   L   G   K gaagtcggcgagatcctgtctgcctgctgggctttcgatctgcaggagagacccagcttc
 E   V   G   E   I   L   S   A   C   W   A   F   D   L   Q   E   R   P   S   F agcctgctgatggacatgctggagaggctgcccaagctgaaccggcggctctccaccct
 S   L   L   M   D   M   L   E   R   L   P   K   L   N   R   R   L   S   H   P gggcacttttggaagtcggctgacattaacagcagcaaagtcatgccccgctttgaaagg
 G   H   F   W   K   S   A   D   I   N   S   S   K   V   M   P   R   F   E   R Tttggcctggggaccctggagtccggtaatccaaagatgtag
 F   G   L   G   T   L   E   S   G   N   P   K   M   -
```

FIGURE 17 atgggagaga aggagggcgg tggcgggggg gatgcggcgg ccgcggaggg tggcgcaggg
  AS-ODN4(1-18)
gccgcggcca gccgggcgct gcagcagtgt gggcagctcc agaagctcat cgacatctcc atcggcagtc tgcgcgggct gcgcaccaag tgcgcagtgt ctaacgacct cacccagcag
    AS-ODN3(124-141)         AS-ODN2(154-171)
gagatacgga ccctagaggc aaagctggtc cgttacattt gtaagcagag gcagtgcaag
    AS-ODN1(187-204)   AS-ODN5(205-222)
ctgagcgtgg ctcccggtga gggaccccca gagctcaaca gctaccccg cttcagcgac
      AS-ODN6(247-264)
tggctgtaca ctttcaacgt gaggccggag gtggtgcagg agatcccccg agacctcacg
AS-ODN7(298-315)     AS-ODN8(321-338)  AS-ODN9(351-368)
ctggatgccc tgctggagat gaatgaggcc aaggtgaagg agacgctgcg gcgctgtggg
                  AS-ODN10(379-396)
gccagcgggg atgagtgtgg ccgtctgcag tatgccctca cctgcctgcg gaaggtgaca ggcctgggag gggagcacaa ggaggactcc agttggagtt cattggatgc gcggcgggaa
                                AS-ODN11(511-528)    AS-ODN12
agtggctcag ggccttccac ggacaccctc tcagcagcca gcctgccctg gccccaggg
(531-548)
agctcccagc tgggcagagc aggcaacagc gccagggcc cacgctccat ctccgtgtca gctctgcccg cctcagactc ccccaccccc agcttcagtg agggcctctc agacacctgt
attccccctgc acgccagcgg ccggctgacc ccccgtgccc tgcacagctt catcacccccg
cccaccacac cccagctgcg acggcacacc aagctgaagc caccacggac gccccccca
cccagccgca aggtcttcca gctgctgccc agcttcccca cactcacccg gagcaagtcc
catgagtctc agctggggaa ccgcattgat gacgtctcct cgatgaggtt tgatctctcg
catggatccc cacagatggt acggagggat atcgggctgt cggtgacgca caggttctcc
accaagtcct ggctgtcgca ggtctgccac gtgtgccaga agagcatgat atttggagtg
aagtgcaagc attgcaggtt gaagtgtcac aacaaatgta ccaaagaagc ccctgcctgt
agaatatcct tcctgccact aactcggctt cggaggacag aatctgtccc ctcggacatc
aacaacccgg tggacagagc agccgaaccc cattttggaa ccctccccaa agcactgaca
aagaaggagc accctccggc catgaatcac ctggactcca gcagcaaccc ttcctccacc
acctcctcca caccctcctc accggcgccc ttcccgacat catccaaccc atccagcgcc
accacgcccc caacccctc acctggccag cgggacagca ggttcaactt cccagctgcc
tacttcattc atcatagaca gcagtttatc tttccagaca tttcagcctt tgcacacgca
gccccgctcc ctgaagctgc cgacggtacc cggctcgatg accagccgaa agcagatgtg
ttggaagctc acgaagcgga ggctgaggag ccagaggctg gcaagtcaga ggcagaagac
gatgaggacg aggtggacga cttgccgagc tctcgccggc cctggcgggg ccccatctct
cgcaaggcca gccagaccag cgtgtacctg caggagtggg acatccccct cgagcaggta
gagctgggcg agcccatcgg gcagggccgc tggggccggg tgcaccgcgg ccgctggcat
ggcgaggtgg ccattcgcct gctggagatg gacggccaca accaggacca cctgaagctc
ttcaagaaag aggtgatgaa ctaccggcag acgcggcatg agaacgtggt gctcttcatg
ggggcctgca tgaacccgcc ccacctggcc attatcacca gcttctgcaa ggggcggacg
ttgcactcgt ttgtgaggga ccccaagacg tctctggaca tcaacaagac gaggcaaatc
gctcaggaga tcatcaaggg catgggatat cttcatgcca agggcatcgt acacaaagat
ctcaaatcta agaacgtctt ctatgacaac ggcaaggtgg tcatcacaga cttcgggctg
tttgggatct caggcgtggt ccgagaggga cggcgtgaga accagctaaa gctgtcccac
gactggctgt gctatctggc ccctgagatt gtacgcgaga tgacccccgg gaaggacgag
gatcagctgc cattctccaa agctgctgat gtctatgcat ttgggactgt ttggtatgag
ctgcaagcaa gagactggcc cttgaagaac caggctgcag aggcatccat ctggcagatt
ggaagcgggg aaggaatgaa gcgtgtcctg acttctgtca gcttggggaa ggaagtcagt
gagatcctgt cggcctgctg ggcttttcgac ctgcaggaga gaccagctt cagcctgctg
atggacatgc tggagaaact tcccaagctg aaccggcggc tctcccaccc tggacacttc
tggaagtcag ctgagttgta g Figure 19. Proliferation assay of PANC-1 cells treated with old- and new- KSR AS-ODN2

Inactivation of KSR1 by KSR-AS sensitizes A431 cells to ionizing radiation-induced apoptosis

SEQUENCE LISTING

<160> NUMBER OF SEQ ID NOS: 38

<210> SEQ ID NO 1
<211> LENGTH: 120
<212> TYPE: DNA
<213> ORGANISM: Homo sapiens

<400> SEQUENCE: 1

```
ctgcagaagc tcatcgatat ctccatcggc agtctgcgcg ggctgcgcac caagtgctca      60
gtgtctaacg acctcacaca gcaggagatc cggaccctag aggcaaagct ggtgaaatac     120
```

<210> SEQ ID NO 2
<211> LENGTH: 41
<212> TYPE: PRT
<213> ORGANISM: Homo sapiens

<400> SEQUENCE: 2

Leu Gln Lys Leu Ile Asp Ile Ser Ile Gly Ser Leu Arg Gly Leu Arg
1               5                   10                  15

Thr Lys Cys Ser Val Ser Asn Asp Leu Thr Gln Gln Glu Ile Arg Thr
            20                  25                  30

Leu Glu Ala Lys Leu Val Lys Tyr Ile
        35                  40

<210> SEQ ID NO 3
<211> LENGTH: 19
<212> TYPE: DNA
<213> ORGANISM: Homo sapiens

<400> SEQUENCE: 3

```
ggcagtctgc gcgggctgc                                                   19
```

<210> SEQ ID NO 4
<211> LENGTH: 18
<212> TYPE: DNA
<213> ORGANISM: Homo sapiens

<400> SEQUENCE: 4

```
tcagtgtcta acgacctc                                                    18
```

<210> SEQ ID NO 5
<211> LENGTH: 18
<212> TYPE: DNA
<213> ORGANISM: Homo sapiens

<400> SEQUENCE: 5

```
cggaccctag aggcaaag                                                    18
```

<210> SEQ ID NO 6
<211> LENGTH: 19
<212> TYPE: DNA
<213> ORGANISM: Artificial Sequence
<220> FEATURE:
<223> OTHER INFORMATION: antisense oligonucleotide

<400> SEQUENCE: 6

```
cagcccgcgc agactgccg                                                   19
```

<210> SEQ ID NO 7
<211> LENGTH: 18
<212> TYPE: DNA

<213> ORGANISM: Artificial Sequence
<220> FEATURE:
<223> OTHER INFORMATION: antisense oligonucleotide

<400> SEQUENCE: 7
gaggtcgtta gacactga                                         18

<210> SEQ ID NO 8
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 8
ctttgcctct agggtc                                           16

<210> SEQ ID NO 9
<211> LENGTH: 873
<212> TYPE: PRT
<213> ORGANISM: Mus musculus

<400> SEQUENCE: 9

```
Met Asp Arg Ala Ala Leu Arg Ala Ala Ala Met Gly Glu Lys Lys Glu
1               5                   10                  15

Gly Gly Gly Gly Gly Ala Ala Asp Gly Ala Gly Ala Ala Val
            20                  25                  30

Ser Arg Ala Leu Gln Gln Cys Gly Gln Leu Gln Lys Leu Ile Asp Ile
        35                  40                  45

Ser Ile Gly Ser Leu Arg Gly Leu Arg Thr Lys Cys Ser Val Ser Asn
    50                  55                  60

Asp Leu Thr Gln Gln Glu Ile Arg Thr Leu Glu Ala Lys Leu Val Lys
65                  70                  75                  80

Tyr Ile Cys Lys Gln Gln Gln Ser Lys Leu Ser Val Thr Pro Ser Asp
                85                  90                  95

Arg Thr Ala Glu Leu Asn Ser Tyr Pro Arg Phe Ser Asp Trp Leu Tyr
            100                 105                 110

Ile Phe Asn Val Arg Pro Glu Val Val Gln Glu Ile Pro Gln Glu Leu
        115                 120                 125

Thr Leu Asp Ala Leu Leu Glu Met Asp Glu Ala Lys Ala Lys Glu Met
    130                 135                 140

Leu Arg Arg Trp Gly Ala Ser Thr Glu Glu Cys Ser Arg Leu Gln Gln
145                 150                 155                 160

Ala Leu Thr Cys Leu Arg Lys Val Thr Gly Leu Gly Gly Glu His Lys
                165                 170                 175

Met Asp Ser Gly Trp Ser Ser Thr Asp Ala Arg Asp Ser Ser Leu Gly
            180                 185                 190

Pro Pro Met Asp Met Leu Ser Ser Leu Gly Arg Ala Gly Ala Ser Thr
        195                 200                 205

Gln Gly Pro Arg Ser Ile Ser Val Ser Ala Leu Pro Ala Ser Asp Ser
    210                 215                 220

Pro Val Pro Gly Leu Ser Glu Gly Leu Ser Asp Ser Cys Ile Pro Leu
225                 230                 235                 240

His Thr Ser Gly Arg Leu Thr Pro Arg Ala Leu His Ser Phe Ile Thr
                245                 250                 255

Pro Pro Thr Thr Pro Gln Leu Arg Arg His Ala Lys Leu Lys Pro Pro
            260                 265                 270
```

-continued

```
Arg Thr Pro Pro Pro Ser Arg Lys Val Phe Gln Leu Leu Pro Ser
        275                 280                 285

Phe Pro Thr Leu Thr Arg Ser Lys Ser His Glu Ser Gln Leu Gly Asn
    290                 295                 300

Arg Ile Asp Asp Val Thr Pro Met Lys Phe Glu Leu Pro His Gly Ser
305                 310                 315                 320

Pro Gln Leu Val Arg Arg Asp Ile Gly Leu Ser Val Thr His Arg Phe
                325                 330                 335

Ser Thr Lys Ser Trp Leu Ser Gln Val Cys Asn Val Cys Gln Lys Ser
                340                 345                 350

Met Ile Phe Gly Val Lys Cys Lys His Cys Arg Leu Lys Cys His Asn
        355                 360                 365

Lys Cys Thr Lys Glu Ala Pro Ala Cys Arg Ile Thr Phe Leu Pro Leu
370                 375                 380

Ala Arg Leu Arg Arg Thr Glu Ser Val Pro Ser Asp Ile Asn Asn Pro
385                 390                 395                 400

Val Asp Arg Ala Ala Glu Pro His Phe Gly Thr Leu Pro Lys Ala Leu
                405                 410                 415

Thr Lys Lys Glu His Pro Pro Ala Met Asn Leu Asp Ser Ser Asn
                420                 425                 430

Pro Ser Ser Thr Thr Ser Ser Thr Pro Ser Ser Pro Ala Pro Phe Leu
        435                 440                 445

Thr Ser Ser Asn Pro Ser Ser Ala Thr Thr Pro Pro Asn Pro Ser Pro
        450                 455                 460

Gly Gln Arg Asp Ser Arg Phe Ser Phe Pro Asp Ile Ser Ala Cys Ser
465                 470                 475                 480

Gln Ala Ala Pro Leu Ser Ser Thr Ala Asp Ser Thr Arg Leu Asp Asp
                485                 490                 495

Gln Pro Lys Thr Asp Val Leu Gly Val His Glu Ala Glu Ala Glu Glu
                500                 505                 510

Pro Glu Ala Gly Lys Ser Glu Ala Glu Asp Asp Glu Asp Glu Val
        515                 520                 525

Asp Asp Leu Pro Ser Ser Arg Arg Pro Trp Arg Gly Pro Ile Ser Arg
530                 535                 540

Lys Ala Ser Gln Thr Ser Val Tyr Leu Gln Glu Trp Asp Ile Pro Phe
545                 550                 555                 560

Glu Gln Val Glu Leu Gly Glu Pro Ile Gly Gln Gly Arg Trp Gly Arg
                565                 570                 575

Val His Arg Gly Arg Trp His Gly Glu Val Ala Ile Arg Leu Leu Glu
                580                 585                 590

Met Asp Gly His Asn Gln Asp His Leu Lys Leu Phe Lys Lys Glu Val
        595                 600                 605

Met Asn Tyr Arg Gln Thr Arg His Glu Asn Val Val Leu Phe Met Gly
        610                 615                 620

Ala Cys Met Asn Pro Pro His Leu Ala Ile Ile Thr Ser Phe Cys Lys
625                 630                 635                 640

Gly Arg Thr Leu His Ser Phe Val Arg Asp Pro Lys Thr Ser Leu Asp
                645                 650                 655

Ile Asn Lys Thr Arg Gln Ile Ala Gln Glu Ile Ile Lys Gly Met Gly
                660                 665                 670

Tyr Leu His Ala Lys Gly Ile Val His Lys Asp Leu Lys Ser Lys Asn
        675                 680                 685

Val Phe Tyr Asp Asn Gly Lys Val Val Ile Thr Asp Phe Gly Leu Phe
```

```
                    690                 695                 700
Gly Ile Ser Gly Val Val Arg Glu Glu Arg Glu Asn Gln Leu Lys
705                 710                 715                 720

Leu Ser His Asp Trp Leu Cys Tyr Leu Ala Pro Glu Ile Val Arg Glu
                725                 730                 735

Met Ile Pro Gly Arg Asp Glu Asp Gln Leu Pro Phe Ser Lys Ala Ala
                740                 745                 750

Asp Val Tyr Ala Phe Gly Thr Val Trp Tyr Glu Leu Gln Ala Arg Asp
                755                 760                 765

Trp Pro Phe Lys His Gln Pro Ala Glu Ala Leu Ile Trp Gln Ile Gly
                770                 775                 780

Ser Gly Glu Gly Val Arg Arg Val Leu Ala Ser Val Ser Leu Gly Lys
785                 790                 795                 800

Glu Val Gly Glu Ile Leu Ser Ala Cys Trp Ala Phe Asp Leu Gln Glu
                805                 810                 815

Arg Pro Ser Phe Ser Leu Leu Met Asp Met Leu Glu Arg Leu Pro Lys
                820                 825                 830

Leu Asn Arg Arg Leu Ser His Pro Gly His Phe Trp Lys Ser Ala Asp
                835                 840                 845

Ile Asn Ser Ser Lys Val Met Pro Arg Phe Glu Arg Phe Gly Leu Gly
                850                 855                 860

Thr Leu Glu Ser Gly Asn Pro Lys Met
865                 870

<210> SEQ ID NO 10
<211> LENGTH: 866
<212> TYPE: PRT
<213> ORGANISM: Homo sapiens

<400> SEQUENCE: 10

Met Gly Glu Lys Glu Gly Gly Gly Gly Asp Ala Ala Ala Glu
1               5                   10                  15

Gly Gly Ala Gly Ala Ala Ala Ser Arg Ala Leu Gln Gln Cys Gly Gln
                20                  25                  30

Leu Gln Lys Leu Ile Asp Ile Ser Ile Gly Ser Leu Arg Gly Leu Arg
                35                  40                  45

Thr Lys Cys Ala Val Ser Asn Asp Leu Thr Gln Gln Glu Ile Arg Thr
50                  55                  60

Leu Glu Ala Lys Leu Val Arg Tyr Ile Cys Lys Gln Arg Gln Cys Lys
65                  70                  75                  80

Leu Ser Val Ala Pro Gly Glu Arg Thr Pro Glu Leu Asn Ser Tyr Pro
                85                  90                  95

Arg Phe Ser Asp Trp Leu Tyr Thr Phe Asn Val Arg Pro Glu Val Val
                100                 105                 110

Gln Glu Ile Pro Arg Asp Leu Thr Leu Asp Ala Leu Leu Glu Met Asn
                115                 120                 125

Glu Ala Lys Val Lys Glu Thr Leu Arg Arg Cys Gly Ala Ser Gly Asp
                130                 135                 140

Glu Cys Gly Arg Leu Gln Tyr Ala Leu Thr Cys Leu Arg Lys Val Thr
145                 150                 155                 160

Gly Leu Gly Gly Glu His Lys Glu Asp Ser Ser Trp Ser Ser Leu Asp
                165                 170                 175

Ala Arg Arg Glu Ser Gly Ser Gly Pro Ser Thr Asp Thr Leu Ser Ala
                180                 185                 190
```

```
Ala Ser Leu Pro Trp Pro Gly Ser Ser Gln Leu Gly Arg Ala Gly
        195                 200                 205

Asn Ser Ala Gln Gly Pro Arg Ser Ile Ser Val Ser Ala Leu Pro Ala
    210                 215                 220

Ser Asp Ser Pro Thr Pro Ser Phe Ser Glu Gly Leu Ser Asp Thr Cys
225                 230                 235                 240

Ile Pro Leu His Ala Ser Gly Arg Leu Thr Pro Arg Ala Leu His Ser
                245                 250                 255

Phe Ile Thr Pro Pro Thr Thr Pro Gln Leu Arg Arg His Thr Lys Leu
            260                 265                 270

Lys Pro Pro Arg Thr Pro Pro Pro Ser Arg Lys Val Phe Gln Leu
        275                 280                 285

Leu Pro Ser Phe Pro Thr Leu Thr Arg Arg Lys Ser His Glu Ser Gln
    290                 295                 300

Leu Gly Asn Arg Ile Asp Asp Val Ser Ser Met Arg Phe Asp Leu Ser
305                 310                 315                 320

His Gly Ser Pro Gln Met Val Arg Arg Asp Ile Gly Leu Ser Val Thr
                325                 330                 335

His Arg Phe Ser Thr Lys Ser Trp Leu Ser Gln Val Cys His Val Cys
            340                 345                 350

Gln Lys Ser Met Ile Phe Gly Val Lys Cys Lys His Cys Arg Leu Lys
        355                 360                 365

Cys His Asn Lys Cys Thr Lys Glu Ala Pro Ala Cys Arg Ile Ser Phe
    370                 375                 380

Leu Pro Leu Thr Arg Leu Arg Arg Thr Glu Ser Val Pro Ser Asp Ile
385                 390                 395                 400

Asn Asn Pro Val Asp Arg Ala Ala Glu Pro His Phe Gly Thr Leu Pro
                405                 410                 415

Lys Ala Leu Thr Lys Lys Glu His Pro Pro Ala Met Asn His Leu Asp
            420                 425                 430

Ser Ser Ser Asn Pro Ser Ser Thr Thr Ser Ser Thr Pro Ser Ser Pro
        435                 440                 445

Ala Pro Phe Pro Thr Ser Ser Asn Pro Ser Ser Ala Thr Thr Pro Pro
    450                 455                 460

Asn Pro Ser Pro Gly Gln Arg Asp Ser Arg Phe Asn Phe Pro Ala Ala
465                 470                 475                 480

Tyr Phe Ile His His Arg Gln Gln Phe Ile Phe Pro Asp Ile Ser Ala
                485                 490                 495

Phe Ala His Ala Ala Pro Leu Pro Glu Ala Ala Asp Gly Thr Arg Leu
            500                 505                 510

Asp Asp Gln Pro Lys Ala Asp Val Leu Glu Ala His Glu Ala Glu Ala
        515                 520                 525

Glu Glu Pro Glu Ala Gly Lys Ser Glu Ala Glu Asp Asp Glu Asp Glu
    530                 535                 540

Val Asp Asp Leu Pro Ser Ser Arg Arg Pro Trp Arg Gly Pro Ile Ser
545                 550                 555                 560

Arg Lys Ala Ser Gln Thr Ser Val Tyr Leu Gln Glu Trp Asp Ile Pro
                565                 570                 575

Phe Glu Gln Val Glu Leu Gly Glu Pro Ile Gly Gln Gly Arg Trp Gly
            580                 585                 590

Arg Val His Arg Gly Arg Trp His Gly Glu Val Ala Ile Arg Leu Leu
        595                 600                 605

Glu Met Asp Gly His Asn Gln Asp His Leu Lys Leu Phe Lys Lys Glu
```

-continued

```
                610               615               620
Val Met Asn Tyr Arg Gln Thr Arg His Glu Asn Val Val Leu Phe Met
625                       630                     635                     640

Gly Ala Cys Met Asn Pro Pro His Leu Ala Ile Ile Thr Ser Phe Cys
              645                     650                     655

Lys Gly Arg Thr Leu His Ser Phe Val Arg Asp Pro Lys Thr Ser Leu
                  660                     665                     670

Asp Ile Asn Lys Thr Arg Gln Ile Ala Gln Glu Ile Lys Gly Met
          675                     680                     685

Gly Tyr Leu His Ala Lys Gly Ile Val His Lys Asp Leu Lys Ser Lys
690                     695                     700

Asn Val Phe Tyr Asp Asn Gly Lys Val Val Ile Thr Asp Phe Gly Leu
705                     710                     715                     720

Phe Gly Ile Ser Gly Val Val Arg Glu Gly Arg Arg Glu Asn Gln Leu
                  725                     730                     735

Lys Leu Ser His Asp Trp Leu Cys Tyr Leu Ala Pro Glu Ile Val Arg
              740                     745                     750

Glu Met Thr Pro Gly Lys Asp Glu Asp Gln Leu Pro Phe Ser Lys Ala
              755                     760                     765

Ala Asp Val Tyr Ala Phe Gly Thr Val Trp Tyr Glu Leu Gln Ala Arg
770                     775                     780

Asp Trp Pro Leu Lys Asn Gln Ala Ala Glu Ala Ser Ile Trp Gln Ile
785                     790                     795                     800

Gly Ser Gly Glu Gly Met Lys Arg Val Leu Thr Ser Val Ser Leu Gly
                  805                     810                     815

Lys Glu Val Ser Glu Ile Leu Ser Ala Cys Trp Ala Phe Asp Leu Gln
              820                     825                     830

Glu Arg Pro Ser Phe Ser Leu Leu Met Asp Met Leu Glu Lys Leu Pro
              835                     840                     845

Lys Leu Asn Arg Arg Leu Ser His Pro Gly His Phe Trp Lys Ser Ala
   850                     855                     860

Glu Leu
865

<210> SEQ ID NO 11
<211> LENGTH: 4094
<212> TYPE: DNA
<213> ORGANISM: Mus musculus

<400> SEQUENCE: 11
gaattccctc gggctttcc tgccgaggcg cccgtgtccc cgggctcctc gcctcggccc      60
ccagcggccc cgatgccgag gcatggatag agcggcgttg cgcgcggcag cgatgggcga     120
gaaaaaggag ggcggcggcg ggggcgccgc ggcggacggg ggcgcagggg ccgccgtcag     180
ccgggcgctg cagcagtgcg gccagctgca gaagctcatc gatatctcca tcggcagtct     240
gcgcgggctg cgcaccaagt gctcagtgtc taacgacctc acacagcagg agatccggac     300
cctagaggca aagctggtga atacatttg caagcagcag cagagcaagc ttagtgtgac     360
cccaagcgac aggaccgccg agctcaacag ctacccacgc ttcagtgact ggctgtacat     420
cttcaacgtg aggcctgagg tggtgcagga gatccccccaa gagctcacac tggatgctct     480
gctggagatg gacgaggcca agccaaggaa gatgctgcgg cgctgggggg ccagcacgga     540
ggagtgcagc cgcctacagc aagcccttac ctgcctttcgg aaggtgactg gcctgggagg     600
ggagcacaaa atggactcag gttggagttc aacagatgct cgagacagta gcttggggcc     660
```

-continued

```
tcccatggac atgctttcct cgctgggcag agcgggtgcc agcactcagg gaccccgttc    720
catctccgtg tccgccctgc ctgcctcaga ctctccggtc cccggcctca gtgagggcct    780
ctcggactcc tgtatcccct gcacaccag cggccggctg accccccggg ccctgcacag     840
cttcatcacg cccctacca caccccagct acgacggcac gccaagctga agccaccaag     900
gacaccccca ccgccaagcc gcaaggtctt ccagctgctc cccagcttcc ccacactcac    960
acggagcaag tcccacgagt cccagctggg aaaccgaatc gacgacgtca ccccgatgaa   1020
gtttgaactc cctcatggat ccccacagct ggtacgaagg gatatcgggc tctcggtgac   1080
gcacaggttc tccacaaagt catggttgtc acaggtgtgc aacgtgtgcc agaagagcat   1140 gattttttggc gtgaagtgca aacactgcag gttaaaatgc cataacaagt gcacaaagga   1200
agctcccgcc tgcaggatca ccttcctccc actggccagg cttcggagga cagagtctgt   1260
cccgtcagat atcaacaacc cagtggacag agcagcagag ccccattttg gaacccttcc   1320
caaggccctg acaaagaagg agcaccctcc agccatgaac ctggactcca gcagcaaccc   1380
atcctccacc acgtcctcca caccctcatc gccggcacct ttcctgacct catctaatcc   1440
ctccagtgcc accacgcctc ccaacccgtc acctggccag cgggacagca ggttcagctt   1500
cccagacatt tcagcctgtt ctcaggcagc cccgctgtcc agcacagccg acagtacacg   1560
gctcgacgac cagcccaaaa cagatgtgct aggtgttcac gaagcagagg ctgaggagcc   1620
tgaggctggc aagtcagagg cagaggatga cgaggaggat gaggtggacg acctccccag   1680
ctcccgccgg ccctggaggg gccccatctc tcgaaaggcc agccagacca gcgtttacct   1740
gcaagagtgg gacatcccct ttgaacaggt ggaactgggc gagcccattg acagggtcg    1800 ctggggccgg gtgcaccgag gccgttggca tggcgaggtg gccattcggc tgctggagat   1860
ggacggccac aatcaggacc acctgaagct gttcaagaaa gaggtgatga actaccggca   1920
gacgcggcat gagaacgtgg tgctcttcat gggggcctgc atgaacccac ctcacctggc   1980
cattatcacc agcttctgca aggggcggac attgcattca ttcgtgaggg accccaagac   2040
gtctctggac atcaataaga ctaggcagat cgcccaggag atcatcaagg catgggtta    2100 tcttcatgca aaaggcatcg tgcacaagga cctcaagtcc aagaatgtct tctatgacaa   2160
cggcaaagtg gtcatcacag acttcgggct gtttgggatc tcgggtgtgg tccgagagga   2220
acggcgcgag aaccaactga aactgtcaca tgactggctg tgctacctgg ccccgagat    2280 cgtacgagaa atgatcccgg ggcgggacga ggaccagctg cccttctcca aagcagccga   2340
tgtctatgca ttcgggactg tgtggtatga actacaggca agagactggc cctttaagca   2400
ccagcctgct gaggccttga tctggcagat tggaagtggg gaaggagtac ggcgcgtcct   2460
ggcatccgtc agcctgggga aggaagtcgg cgagatcctg tctgcctgct ggctttcga   2520 tctgcaggag agacccagct tcagcctgct gatggacatg ctggagaggc tgcccaagct   2580
gaaccggcgg ctctcccacc ctgggcactt ttggaagtcg gctgacatta acagcagcaa   2640
agtcatgccc cgctttgaaa ggtttggcct ggggaccctg gagtccggta atccaaagat   2700
gtagccagcc ctgcacgttc atgcagagag tgtcttcctt tcgaaaacat gatcacgaaa   2760
catgcagacc accacctcaa ggaatcagaa gcattgcatc ccaagctgcg gactgggagc   2820
gtgtctcctc cctaaaggac gtgcgtgcgt gcgtgcgtgc gtgcgtgcgt gcgtgcgtca   2880
ccaaggtgtg tggagctcag gatcgcagcc atacacgcaa ctccagatga taccactacc   2940
gccagtgttt acacagaggt ttctgcctgg caagcttggt attttacagt aggtgaagat   3000
```

| | |
|---|---:|
| cattctgcag aagggtgctg gcacagtgga gcagcacgga tgtccccagc ccccgttctg | 3060 |
| gaagacccta cagctgtgag aggcccaggg ttgagccaga tgaaagaaaa gctgcgtggg | 3120 |
| tgtgggctgt acccggaaaa gggcaggtgg caggaggttt gccttggcct gtgcttgggc | 3180 |
| cgagaaccac actaaggagc agcagcctga gttaggaatc tatctggatt acggggatca | 3240 |
| gagttcctgg agagtggact cagtttctgc tctgatccag gcctgttgtg cttttttttt | 3300 |
| ttccccctta aaaaaaaaa agtacagaca gaatctcagc ggcttctaga ctgatctgat | 3360 |
| ggatcttagc ccggcttcta ctgcgggggg gaggggggga gggatagcca catatctgtg | 3420 |
| gagacaccca cttctttatc tgaggcctcc aggtaggcac aaaggctgtg gaactcagcc | 3480 |
| tctatcatca gacaccccc cccaatgcct cattgacccc cttcccccag agccaagggc | 3540 |
| tagcccatcg ggtgtgtgta cagtaagttc ttggtgaagg agaacaggga cgttggcaga | 3600 |
| agcagtttgc agtggcccta gcatcttaaa acccattgtc tgtcacacca gaaggttcta | 3660 |
| gacctaccac cacttccctt ccccatctca tggaaacctt ttagcccatt ctgacccctg | 3720 |
| tgtgtgctct gagctcagat cgggttatga accgcccag gcacatcagt cagggaggct | 3780 |
| ctgatgtgag ccgcagacct ctgtgttcat tcctatgagc tggaggggct ggactgggtg | 3840 |
| gggtcagatg tgcttggcag gaactgtcag ctgctgagca gggtggtccc tgagcggagg | 3900 |
| ataagcagca tcagactcca caaccagagg aagaaagaaa tggggatgga gcggagaccc | 3960 |
| acgggctgag tcccgctgtg gagtggcctt gcagctccct ctcagttaaa actcccagta | 4020 |
| aagccacagt tctccgagca cccaagtctg ctccagccgt tcttaaaac aggccactct | 4080 |
| ctgagaagga attc | 4094 |

<210> SEQ ID NO 12
<211> LENGTH: 3772
<212> TYPE: DNA
<213> ORGANISM: Homo sapiens

<400> SEQUENCE: 12

| | |
|---|---:|
| gcgaagctgg tccgttacat ttgtaagcag aggcagtgca agctgagcgt ggctcccggt | 60 |
| gagaggaccc cagagctcaa cagctacccc cgcttcagcg actggctgta cactttcaac | 120 |
| gtgaggccgg aggtggtgca ggagatcccc cgagacctca cgctggatgc cctgctggag | 180 |
| atgaatgagg ccaaggtgaa ggagacgctg cggcgctgtg gggccagcgg ggatgagtgt | 240 |
| ggccgtctgc agtatgccct cacctgcctg cggaaggtga caggcctggc ttcatcaccc | 300 |
| cgcccaccac accccagctg cgacggcaca ccaagctgaa gccaccacgg acgcccccc | 360 |
| cacccagccg caaggtcttc cagctgctgc ccagcttccc cacactcacc cggagcaagt | 420 |
| cccatgagtc tcagctgggg aaccgcattg atgacgtctc ctcgatgagg tgagttggga | 480 |
| gcacgttcct gcacgtggct atgctgtggg gcctctctca tgagtcagag cggagggaga | 540 |
| cagctgtgcc tctggagtct gcttttaatt gtctggaaat gcagagatgt ctggtttttg | 600 |
| cctgagcaaa ataggagttt attttttgtac tatcccgagc tggctaagga gagtcacgta | 660 |
| gctgtgggcg gggtcttggg gatgaggagg ggtacagcag gcaggacta tgctgaagtg | 720 |
| gagctggctg taggaacccc agggaggcac agggggagca tgaagaggag ctacacttcc | 780 |
| ctcccttagt gcccgggcag aaactcccag ggccttcac agaaccttgg aggaacattc | 840 |
| aacacccca tctctaggac agccccagcc ttgtcatcct ccaattgctg tggtaacacg | 900 |
| gggactggag cagtgagatt attaggcctt cagggccagt gtctccatgc agatcagatg | 960 |
| gaggcggtgc ttggcacata caccacctca ctgcccatgc ccccagaagt tggtgcagat | 1020 |

-continued

```
cataaggtgg cttttggggc taattgattg aagttccaac atagtctgtt tctcctaggc      1080
tggtagctgg cacctttggc cccatgtgtt ttttaattat ttttctttt gagacgaaat       1140 ctcgctctat cacccaggct gaagtgcagt agtgcaatct cagctcactg cagcctctgc      1200
ctcccgggtt caagcaattc tcctgcctca gcctcccgag tagccaggat taaaggtgcc      1260
tgccaccaca catggctaat ttttgtattt taatagaga cggggtttca ccatgttagc       1320
caggctggtc tcaaactcct gacctcaggt gatcttcctg cctcagcctc ccaaagtgct      1380
gggattacag gtgtgagcca ctgcgcccag tcatgcccat gtgttttggt ggtcttggct      1440
gctgatgggt ggggtgagcc ccaggaggaa gttgggacaa gtcaacctca tggcagatgt      1500
gccagggaga gctgcgggtg agatagattg ttcctatccc cctctccttg atgtgggagg      1560
actcagtacc tccagcacac ccttctcatg gaggttggtt atgtggtact tggcctcaag      1620
tgaaccagca cttcatgagt ccagctttgt gctagaccag cacttgggat tgagggggggc     1680 agtggccacc ctcgggggac cttctgactc agaggacatg agatggccac actcgagcac      1740
tgtgttcctg acctttctgg gtcacaggtc accttgatga ttggatgaaa gtcttagatc      1800
ttctttccag agaaaagtct acaacattct actgaaccag tccagagggt tcccggaccc      1860
ccgaagccca cccatgggct ggctctggga ggcaatggcg ctgagtatgg gggcatctct      1920
cgcatggatc cccacagatg gtacggaggg atatcgggct gtcggtgacg cacaggttct      1980
ccaccaagtc ctggctgtcg caggtctgcc acgtgtgcca gaagagcatg atatttggag      2040
tgaagtgcaa gcattgcagg ttgaagtgtc acaacaaatg taccaaagaa gcccctgcct      2100
gtagaatatc cttcctgcca ctaactcggc ttcggaggac agaatctgtc ccctcggaca      2160
tcaacaaccc ggtggacaga gcagccgaac cccattttgg aaccctcccc aaagcactga      2220
caaagaagga gcaccctccg gccatgaatc acctggactc cagcagcaac ccttcctcca      2280
ccacctcctc cacaccctcc tcaccggcgc ccttcccgac atcatccaac ccatccagcg      2340
ccaccacgcc ccccaacccc tcacctggcc agcgggacag caggttcaac ttcccagctg      2400
cctacttcat tcatcataga cagcagttta tcttttccaga catttcagcc tttgcacacg      2460
cagccccgct ccctgaagct gccgacggta cccggctcga tgaccagccg aaagcagatg      2520
tgttggaagc tcacgaagcg gaggctgagg agccagaggc tggcaagtca gaggcagaag      2580
acgatgagga cgaggtggac gacttgccga gctctcgccg gccctggcgg ggccccatct      2640
ctcgcaaggc cagccagacc agcgtgtacc tgcaggagtg ggacatcccc ttcgagcagg      2700
tagagctggg cgagcccatc gggcagggcc gctggggccg ggtgcaccgc ggccgctggc      2760
atggcgaggt ggccattcgc ctgctggaga tggacggcca caaccaggac cacctgaagc      2820
tcttcaagaa agaggtgatg aactaccggc agacgcggca tgagaacgtg gtgctcttca      2880
tgggggcctg catgaacccc ccccacctgg ccattatcac cagcttctgc aaggggcgga      2940
cgttgcactc gtttgtgagg gaccccaaga cgtctctgga catcaacaag acgaggcaaa      3000
tcgctcagga gatcatcaag ggcatgggat atcttcatgc caagggcatc gtacacaaag      3060
atctcaaatc taagaacgtc ttctatgaca acggcaaggt ggtcatcaca gacttcgggc      3120 tgttgggat ctcaggcgtg gtccgagagg acggcgtga gaaccagcta aagctgtccc        3180
acgactggct gtgctatctg gcccctgaga ttgtacgcga tgacccccc gggaaggacg      3240 aggatcagct gccattctcc aaagctgctg atgtctatgc atttgggact gtttggtatg      3300
agctgcaagc aagagactgg gcccttgaaga accaggctgc agaggcatcc atctggcaga     3360
```

-continued

```
ttggaagcgg ggaaggaatg aagcgtgtcc tgacttctgt cagcttgggg aaggaagtca    3420
gtgagatcct gtcggcctgc tgggctttcg acctgcagga gagacccagc ttcagcctgc    3480
tgatggacat gctggagaaa cttcccaagc tgaaccggcg gctctcccac cctggacact    3540
tctggaagtc agctgagttg taggcctggc tgccttgcat gcaccagggg ctttcttcct    3600
cctaatcaac aactcagcac cgtgacttct gctaaaatgc aaaatgagat gcgggcacta    3660
acccagggga tgccacctct gctgctccag tcgtctctct cgaggctact tcttttgctt    3720
tgttttaaaa actggccctc tgccctctcc acgtggcctg catatgccca ag            3772
```

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
ggaaccttac ttctgtggtg tgac                                            24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
tagcagacac tctatgcctg tgtg                                            24

<210> SEQ ID NO 15
<211> LENGTH: 18
<212> TYPE: DNA
<213> ORGANISM: Artificial Sequence
<220> FEATURE:
<223> OTHER INFORMATION: sense oligonucleotide

<400> SEQUENCE: 15
cggaccctag aggcaaag                                                   18

<210> SEQ ID NO 16
<211> LENGTH: 20
<212> TYPE: DNA
<213> ORGANISM: Artificial Sequence
<220> FEATURE:
<223> OTHER INFORMATION: control oligonucleotide

<400> SEQUENCE: 16
cacgtcacgc gcgcactatt                                                 20

<210> SEQ ID NO 17
<211> LENGTH: 6
<212> TYPE: PRT
<213> ORGANISM: Homo sapiens

<400> SEQUENCE: 17

Gly Ser Leu Arg Gly Leu
1               5

<210> SEQ ID NO 18
<211> LENGTH: 6
<212> TYPE: PRT
<213> ORGANISM: Homo sapiens

```
<400> SEQUENCE: 18

Ala Val Ser Asn Asp Leu
1               5

<210> SEQ ID NO 19
<211> LENGTH: 6
<212> TYPE: PRT
<213> ORGANISM: Homo sapiens

<400> SEQUENCE: 19

Arg Thr Leu Glu Ala Lys
1               5

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
tatctccatc ggcagtct                                                 18

<210> SEQ ID NO 21
<211> LENGTH: 18
<212> TYPE: DNA
<213> ORGANISM: Artificial Sequence
<220> FEATURE:
<223> OTHER INFORMATION: primer

<400> SEQUENCE: 21
tcgacgctca cacttcaa                                                 18

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
ctgaccgctt cctcgtg                                                  17

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
atagagccca ccgcatcc                                                 18

<210> SEQ ID NO 24
<211> LENGTH: 2601
<212> TYPE: DNA
<213> ORGANISM: Homo sapiens

<400> SEQUENCE: 24
atgggagaga aggagggcgg tggcggggggg gatgcggcgg ccgcggaggg tggcgcaggg      60
gccgcggcca gccgggcgct gcagcagtgt gggcagctcc agaagctcat cgacatctcc     120
atcggcagtc tgcgcgggct gcgcaccaag tgcgcagtgt ctaacgacct cacccagcag     180
gagatacgga ccctagaggc aaagctggtc cgttacattt gtaagcagag gcagtgcaag     240
```

-continued

```
ctgagcgtgg ctcccggtga gaggacccca gagctcaaca gctaccccg cttcagcgac      300
tggctgtaca ctttcaacgt gaggccggag gtggtgcagg agatccccg agacctcacg      360
ctggatgccc tgctggagat gaatgaggcc aaggtgaagg agacgctgcg gcgctgtggg      420
gccagcgggg atgagtgtgg ccgtctgcag tatgccctca cctgcctgcg aaggtgaca       480
ggcctgggag gggagcacaa ggaggactcc agttggagtt cattggatgc gcggcgggaa      540
agtggctcag ggccttccac ggacaccctc tcagcagcca gcctgccctg cccccaggg       600
agctcccagc tgggcagagc aggcaacagc gcccagggcc cacgctccat ctccgtgtca      660
gctctgcccg cctcagactc ccccaccccc agcttcagtg agggcctctc agacacctgt      720
attcccctgc acgccagcgg ccggctgacc ccccgtgccc tgcacagctt catcaccccg      780
cccaccacac cccagctgcg acggcacacc aagctgaagc caccacggac gcccccccca      840
cccagccgca aggtcttcca gctgctgccc agcttcccca cactcacccg gagcaagtcc      900
catgagtctc agctggggaa ccgcattgat gacgtctcct cgatgaggtt tgatctctcg      960
catggatccc cacagatggt acggagggat atcgggctgt cggtgacgca caggttctcc     1020
accaagtcct ggctgtcgca ggtctgccac gtgtgccaga gagcatgat atttggagtg      1080
aagtgcaagc attgcaggtt gaagtgtcac aacaaatgta ccaaagaagc ccctgcctgt     1140
agaatatcct tcctgccact aactcggctt cggaggacag aatctgtccc ctcggacatc     1200
aacaacccgg tggacagagc agccgaaccc cattttggaa ccctcccaa agcactgaca      1260
aagaaggagc accctccggc catgaatcac ctggactcca gcagcaaccc ttcctccacc     1320
acctcctcca caccctcctc accggcgccc ttcccgacat catccaaccc atccagcgcc     1380
accacgcccc caaccccctc acctggccag cgggacagca ggttcaactt cccagctgcc     1440
tacttcattc atcatagaca gcagtttatc tttccagaca tttcagcctt tgcacacgca     1500
gccccgctcc tgaagctgc cgacggtacc cggctcgatg accagccgaa agcagatgtg       1560
ttggaagctc acgaagcgga ggctgaggag ccagaggctg gcaagtcaga ggcagaagac     1620
gatgaggacg aggtggacga cttgccgagc ctcgccggc cctggcgggg ccccatctct      1680
cgcaaggcca gccagaccag cgtgtacctg caggagtggg acatcccctt cgagcaggta     1740
gagctgggcg agcccatcgg gcaggccgc tgggccgggg tgcaccgcgg ccgctggcat      1800
ggcgaggtgg ccattcgcct gctggagatg gacggccaca accaggacca cctgaagctc     1860
ttcaagaaag aggtgatgaa ctaccggcag acgcggcatg agaacgtggt gctcttcatg     1920
ggggcctgca tgaacccgcc ccacctggcc attatcacca gcttctgcaa ggggcggacg     1980
ttgcactcgt tgtgaggga ccccaagacg tctctggaca tcaacaagac gaggcaaatc      2040
gctcaggaga tcatcaaggg catgggatat cttcatgcca agggcatcgt acacaaagat     2100
ctcaaatcta agaacgtctt ctatgacaac ggcaaggtgg tcatcacaga cttcgggctg     2160
tttgggatct caggcgtggt ccgagaggga cggcgtgaga accagctaaa gctgtcccac     2220
gactggctgt gctatctggc ccctgagatt gtacgcgaga tgaccccggg aaggacgag      2280
gatcagctgc cattctccaa agctgctgat gtctatgcat ttgggactgt ttggtatgag     2340
ctgcaagcaa gagactggcc cttgaagaac caggctgcag aggcatccat ctggcagatt     2400
ggaagcgggg aaggaatgaa gcgtgtcctg acttctgtca gcttgggaa ggaagtcagt      2460
gagatcctgt cggcctgctg ggcttttcgac ctgcaggaga cccagctt cagcctgctg      2520
atggacatgc tggagaaact tcccaagctg aaccggcggc tctcccaccc tggacacttc    2580
```

```
tggaagtcag ctgagttgta g                                              2601

<210> SEQ ID NO 25
<211> LENGTH: 121
<212> TYPE: DNA
<213> ORGANISM: Homo sapiens

<400> SEQUENCE: 25
ctccagaagc tcatcgacat ctccatcggc agtctgcgcg ggctgcgcac caagtgcgca     60
gtgtctaacg acctcaccca gcaggagata cggaccctag aggcaaagct ggtccgttac    120
a                                                                    121

<210> SEQ ID NO 26
<211> LENGTH: 40
<212> TYPE: PRT
<213> ORGANISM: Homo sapiens

<400> SEQUENCE: 26

Leu Gln Lys Leu Ile Asp Ile Ser Ile Gly Ser Leu Arg Gly Leu Arg
1               5                   10                  15

Thr Lys Cys Ala Val Ser Asn Asp Leu Thr Gln Gln Glu Ile Arg Thr
            20                  25                  30

Leu Glu Ala Lys Leu Val Arg Tyr
        35                  40

<210> SEQ ID NO 27
<211> LENGTH: 18
<212> TYPE: DNA
<213> ORGANISM: Homo sapiens

<400> SEQUENCE: 27
gcagtgtcta acgacctc                                                   18

<210> SEQ ID NO 28
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 28
ctttgcctct agggtccg                                                   18

<210> SEQ ID NO 29
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 29
cagcccgcgc agactgcc                                                   18

<210> SEQ ID NO 30
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 30
gccctccttc tctcccat                                                   18
```

```
<210> SEQ ID NO 31
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 31
acaaatgtaa cggaccag                                                 18

<210> SEQ ID NO 32
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 32
cctctcaccg ggagccac                                                 18

<210> SEQ ID NO 33
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 33
gaaagtgtac agccagtc                                                 18

<210> SEQ ID NO 34
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 34
tgcaccacct ccggcctc                                                 18

<210> SEQ ID NO 35
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 35
tgaggtctcg ggggatct                                                 18

<210> SEQ ID NO 36
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 36
caccttggcc tcattcat                                                 18

<210> SEQ ID NO 37
<211> LENGTH: 18
<212> TYPE: DNA
<213> ORGANISM: Artificial Sequence
<220> FEATURE:
<223> OTHER INFORMATION: antisense oligonucleotide
```

```
<400> SEQUENCE: 37
atccaatgaa ctccaact                                                  18

<210> SEQ ID NO 38
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 38
gagccacttt cccgccgc                                                  18
```

KINASE SUPPRESSOR OF RAS INACTIVATION FOR THERAPY OF RAS MEDIATED TUMORIGENESIS

CROSS REFERENCE TO RELATED APPLICATIONS

The present application is a Continuation-in-Part of co-pending PCT Application NO. PCT/US03/16961 filed May 29, 2003, which in turn, claims priority from U.S. Provisional Application Ser. No. 60/384,228, filed May 30, 2002, and U.S. Provisional Application Ser. No. 60/460,023, filed Apr. 3, 2003. Applicants claim the benefits of 35 U.S.C. § 120 as to the PCT application and priority under U.S.C. § 119(e) as to said United States Provisional applications, and the entire disclosures of all of which applications are incorporated herein by reference in their entireties.

GOVERNMENTAL SUPPORT

The research leading to the present invention was supported, at least in part, by a grant from the National Institutes of Health, Grant No.CA42385 and Grant No.CA52462. Accordingly, the Government may have certain rights in the invention.

FIELD OF THE INVENTION

The present invention relates to methods and compositions for the specific inhibition of kinase suppressor of Ras (KSR). In particular, the invention provides genetic approaches and nucleic acids for the specific inhibition of KSR, particularly of KSR expression. The invention relates to antisense oligonucleotides and the expression of nucleic acid complementary to KSR RNA to specifically inhibit KSR and block gf Ras mediated tumorigenesis.

BACKGROUND OF THE INVENTION

Ras plays an essential role in oncogenic transformation and genesis. Oncogenic H-, K-, and N-Ras arise from point mutations limited to a small number of sites (amino acids 12, 13, 59 and 61). Unlike normal Ras, oncogenic ras proteins lack intrinsic GTPase activity and hence remain constitutively activated (Trahey, M., and McCormick, F. (1987) Science 238: 542-5; Tabin, C. J. et al. (1982) Nature. 300: 143-9; Taparowsky, E. et al. (1982) Nature. 300: 762-5). The participation of oncogenic ras in human cancers is estimated to be 30% (Almoguera, C. et al (1988) Cell. 53:549-54).

Mutations are frequently limited to only one of the ras genes, and the frequency is tissue- and tumor type-specific. K-ras is the most commonly mutated oncogene in human cancers, especially the codon-12 mutation. While oncogenic activation of H-, K-, and N-Ras arising from single nucleotide substitutions has been observed in 30% of human cancers (Bos, J. L. (1989) Cancer Res 49, 4682-9), over 90% of human pancreatic cancer manifest the codon 12 K-ras mutation (Almoguera, C. et al. (1988) Cell 53, 549-54; Smit, V. T. et al. (1988) Nucleic Acids Res 16, 7773-82; Bos, J. L. (1989) Cancer Res 49, 4682-9). Pancreatic ductal adenocarcinoma, the most common cancer of the pancreas, is notorious for its rapid onset and resistance to treatment. The high frequency of K-ras mutations in human pancreatic tumors suggests that constitutive Ras activation plays a critical role during pancreatic oncogenesis. Adenocarcinoma of the exocrine pancreas represents the fourth-leading cause of cancer-related mortality in Western countries. Treatment has had limited success and the five-year survival remains less than 5% with a mean survival of 4 months for patients with surgically unresectable tumors (Jemal, A et al (2002) CA Cancer J Clin 52, 23-47; Burris, H. A., 3rd et al. (1997) J Clin Oncol 15, 2403-13). This point mutation can be identified early in the course of the disease when normal cuboidal pancreatic ductal epithelium progresses to a flat hyperplastic lesion, and is considered causative in the pathogenesis of pancreatic cancer (Hruban, R. H. et al (2000) Clin Cancer Res 6, 2969-72; Tada, M. et al. (1996) Gastroenterology 110, 227-31). The regulation of oncogenic K-ras signaling in human pancreatic cancer, however, remains largely unknown.

K-ras mutations are present in 50% of the cancers of colon and lung (Bos, J. L. et al. (1987) Nature. 327: 293-7; Rodenhuis, S. et al. (1988) Cancer Res. 48: 5738-41). In cancers of the urinary tract and bladder, mutations are primarily in the H-ras gene (Fujita, J. et al. (1984) Nature. 309: 464-6; Visvanathan, K. V. et al. (1988) Oncogene Res. 3: 77-86). N-ras gene mutations are present in 30% of leukemia and liver cancer. Approximately 25% of skin lesions in humans involve mutations of the Ha-Ras (25% for squamous cell carcinoma and 28% for melanomas) (Bos, J. L. (1989) Cancer Res. 49:4683-9; Migley, R. S. and Kerr, D. J. (2002) Crit Rev Oncol Hematol. 44:109-20).50-60% of thyroid carcinomas are unique in having mutations in all three genes (Adjei, A. A. (2001) J Natl Cancer Inst. 93: 1062-74).

Constitutive activation of Ras can be achieved through oncogenic mutations or via hyperactivated growth factor receptors such as the EGFRs. Elevated expression and/or amplification of the members of the EGFR family, especially the EGFR and HER2, have been implicated in various forms of human malignancies (as reviewed in Prenzel, N. et al. (2001) Endocr Relat Cancer. 8: 11-31). In some of these cancers (including pancreas, colon, bladder, lung), EGFR/HER2 overexpression is compounded by the presence of oncogenic Ras mutations. Abnormal activation of these receptors in tumors can be attributed to overexpression, gene amplification, constitutive activation mutations or autocrine growth factor loops (Voldborg, B. R. et al. (1997) Ann Oncol. 8:1197-206). For growth factor receptors, especially the EGFRs, amplification or/and overexpression of these receptors frequently occur in the cancers of the breast, ovary, stomach, esophagus, pancreatic, lung, colon neuroblastoma.

While various therapeutic strategies have been developed to inactivate key components of the Ras-Raf-MAPK cascade, specific inhibition of gain-of-function or constitutive Ras (gfRas) action has not been achieved clinically (Adjei, A. A. (2001) J Natl Cancer Inst 93, 1062-74; Cox, A. D. & Der, C. J. (2002) Curr Opin Pharmacol 2, 388-93).

Therefore, in view of the aforementioned deficiencies attendant with prior art methods to inactivate or inhibit the Ras pathway, and particularly Ras-mediated cancers, it should be apparent that there still exists a need in the art for methods and compositions for specific inhibition of the Ras pathway and particularly for inhibition of gfRas.

The citation of references herein shall not be construed as an admission that such is prior art to the present invention.

SUMMARY OF THE INVENTION

The present invention relates to methods and compositions for the specific inhibition of kinase suppressor of Ras (KSR). The compositions and methods of the present invention inhibit the expression and/or activity of KSR. In particular, the invention provides genetic approaches and nucleic acids for the specific inhibition of KSR. It is herein demonstrated that on specific inhibition of KSR the Ras pathway is disrupted and, specifically, Ras-mediated tumors and tumorigenesis is inhibited or blocked, existing tumors regress, metasasis is inhibited and proliferation of tumor or cancer cells is inhibited.

The present invention provides oligonucleotides and nucleic acids which specifically inhibit or block the expression and activity of KSR. In particular, antisense oligonucleotides and the expression of nucleic acid complementary to KSR RNA specifically inhibits expression of KSR and blocks gfRas mediated tumorigenesis.

The present invention provides an oligonucleotide which is substantially complementary to a region of KSR RNA, wherein said oligonucleotide inhibits the expression of KSR. The invention further provides an oligonucleotide which is substantially complementary to a nucleic acid encoding mammalian KSR. In particular embodiments, oligonucleotides are provided which are substantially complementary to nucleic acid encoding mammalian KSR, particularly human and mouse KSR.

In an aspect of the invention an oligonucleotide is provided which is substantially complementary to a translation initiation site, 5' untranslated region, coding region or 3' untranslated region of mRNA encoding mammalian KSR. In one such aspect, the invention thus provides an oligonucleotide which is substantially complementary to a translation initiation site, 5' untranslated region, coding region or 3' untranslated region of mRNA encoding human KSR as provided in FIG. 14 and SEQ ID NO:24. In a particular embodiment, the invention provides an antisense oligonucleotide substantially complementary to the N-terminal coding region of mammalian KSR mRNA, particularly to the region of nucleotides 1 through 761 of the coding region of mammalian KSR mRNA. In one embodiment, the invention includes an antisense oligonucleotide comprising a sequence substantially complementary to the CA1 region of KSR. The invention provides oligonucleotides comprising a sequence substantially complementary to nucleotides encoding amino acids 33 to 72 of the sequence of human KSR and amino acids 42 to 82 of the sequence of mouse KSR, or a portion thereof.

In a further embodiment, the invention includes an antisense oligonucleotide complising a sequence substantially complementary to nucleotides 97 to 216 of the coding sequence of human KSR (SEQ ID NO: 25) or nucleotides 124 to 243 of the coding sequence of mouse KSR (SEQ ID NO: 1), or a portion thereof, such nucleotides encoding amino acids 33 to 72 of human KSR (SEQ ID NO: 26) and amino acids 42 to 82 of mouse KSR (SEQ ID NO:2) or a portion thereof. In particular, oligonucleotides of the invention include oligonucleotides comprising a sequence substantially complementary to nucleotides selected from the group of: nucleotides 124 to 141 of human KSR, corresponding to nucleotides 151 to 168 of mouse KSR (SEQ ID NO: 3); nucleotides 154 to 171 of human KSR (SEQ ID NO: 27), corresponding nearly identically (with a single base pair difference at the 5' most nucleotide) to nucleotides 181 to 198 of mouse KSR (SEQ ID NO:4); and nucleotides 187 to 204 of human KSR, corresponding to nucleotides 214 to 231 of mouse KSR (SEQ ID NO:5). The invention includes antisense oligonucleotides comprising a sequence selected from the group of SEQ ID NOS: 6-8 and SEQ ID NOS: 29-38.

The oligonucleotides of the present invention may be labeled with a detectable label. In particular aspects, the label may be selected from enzymes, ligands, chemicals which fluoresce and radioactive elements. In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

In a particular aspect, the nucleic acids and oligonucleotides of the present invention may be modified, either by manipulation of the chemical backbone of the nucleic acids or by covalent or non-covalent attachment of other moieties. In each or any case, such manipulation or attachment may serve to modify the stability, cellular, tissue or organ uptake, or otherwise enhance efficacy of the nucleic acids and oligonucleotides. In further aspects of the invention, the oligonucleotides may be covalently linked to other molecules, including but not limited to polypeptides, carbohydrates, lipid or lipid-like moieties, ligands, chemical agents or compounds, which may serve to enhance the uptake, stability or to target the oligonucleotides.

In further embodiments, the oligonucleotides of the present invention are modified in their chemical backbone. In a particular embodiment, the oligonucleotides comprise at least one phosphorothioate (P-S) linkage.

Recombinant DNA molecules comprising a nucleic acid sequence which encodes on transcription an antisense RNA complementary to mammalian KSR RNA or a portion thereof are provided by the invention. Further, the recombinant DNA molecules comprise a nucleic acid sequence wherein said nucleic acid sequence is operatively linked to a transcription control sequence. Cell lines transfected with these recombinant DNA molecules are also included in the invention.

In a further aspect, an expression vector is provided which is capable of expressing a nucleic acid which is substantially complementary to the coding sequence of KSR RNA, or a portion thereof, wherein said nucleic acid inhibits the expression of KSR. In a particular aspect, this includes an expression vector capable of expressing an oligonucleotide which is substantially complementary to the CA1 region of the coding sequence of KSR RNA, particularly of mouse or human KSR (SEQ ID NO: 1 or SEQ ID NO: 25), or a portion thereof, wherein said oligonucleotide inhibits the expression of KSR.

Compositions of the nucleic acids and oligonucleotides are an additional aspect of the invention. The invention includes a composition comprising an oligonucleotide which is substantially complementary to a region of KSR RNA and a pharmaceutically acceptable carrier or diluent. The invention thus provides a pharmaceutical composition comprising a therapeutically effective amount of an oligonucleotide which is substantially complementary to a region of KSR RNA and a pharmaceutically acceptable carrier or diluent.

In a further aspect, compositions are provided comprising one or more chemotherapeutic or radiotherapeutic agent and an oligonucleotide which is targeted to a mRNA encoding mammalian KSR and which inhibits KSR expression.

In an additional embodiment, the invention provides a composition comprising an expression vector and a pharmaceutically acceptable carrier or diluent, wherein said expression vector is capable of expressing nucleic acid which is substantially complementary to the coding sequence of KSR RNA, or a portion thereof, wherein said nucleic acid inhibits the expression of KSR.

Methods for inhibiting expression of KSR are provided. In one aspect, a method of inhibiting the expression of mammalian KSR comprising contacting cells which express KSR with an effective amount of a nucleic acid which is complementary to a portion of the mRNA encoding KSR is included. In particular, a method of inhibiting the expression of mammalian KSR is provided, comprising contacting cells which express KSR with an effective amount of the oligonucleotide of the present invention whereby expression of mammalian KSR is inhibited. In an additional aspect, a method of inhibiting expression of KSR is provided, wherein tissues or a tumor, particularly a tissue or tumor expressing gƒ Ras or wherein the Ras pathway is hyperactivated or Ras is overexpressed or amplified, is contacted with an effective amount of the oligonucleotide or nucleic acid of the present invention, thus inhibiting the expression of KSR.

In a further embodiment, the invention provides compositions and methods for the inhibition or blockage of the activity of KSR, including the kinase or phosphorylation activity of KSR. In an additional aspect, a method of inhibiting expression of KSR is provided, wherein a tumor, tissue or cells expressing KSR, particularly a tissue or tumor expressing gƒ Ras or wherein the Ras pathway is hyperactivated or Ras is overexpressed or amplified, is contacted with an effective amount of the nucleic acid or composition of the present invention, thus inhibiting the activity of KSR.

The invention further includes a method of treating or preventing a hyperproliferative condition associated with the expression of gƒ-Ras or heightened expression of Ras in a mammal comprising administering to said mammal a therapeutically effective amount of a compound or agent which inhibits the expression of mammalian KSR protein. In one aspect of this method, said compound or agent is an antisense oligonucleotide which specifically hybridizes to a portion of the mRNA encoding KSR.

A method of treating or preventing a hyperproliferative condition associated with the expression of gƒ-Ras or heightened expression or hyperactivation of Ras in a mammal is provided, comprising expressing in said mammal or administering to said mammal a therapeutically effective amount of a nucleic acid which is complementary to a portion of the mRNA encoding KSR.

In a further aspect, a method of treating or inhibiting the progression of cancer in a mammal is included, comprising administering to a mammal a therapeutically effective amount of a compound or agent which inhibits the expression of mammalian KSR protein. Cancers which are susceptible to the invention's method include cancer selected from the group of pancreatic cancer, lung cancer, skin cancer, urinary tract cancer, bladder cancer, liver cancer, thyroid cancer, colon cancer, intestinal cancer, leukemia, lymphoma, neuroblastoma, head and neck cancer, breast cancer, ovarian cancer, stomach cancer, esophageal cancer and prostate cancer.

Thus, a method is provided for treating or inhibiting the progression of cancer in a mammal comprising administering to a mammal a therapeutically effective amount of one or more oligonucleotide of the present invention.

In addition, a method is provided for identifying compounds or agents which inhibit the expression of KSR comprising the steps of:
  (a) incubating a cell expressing KSR in the presence and absence of a candidate compound or agent; and
  (b) detecting or measuring the expression of KSR in the presence and absence of a candidate compound or agent, whereby a decrease in the expression of KSR in the presence of said candidate compound or agent versus in the absence of said candidate compound or agent indicates that said compound or agent inhibits the expression of KSR.

The invention includes additional compositions which can inhibit the expression of a protein, in particular KSR, at the transcriptional level by blocking translation of KSR mRNA or by facilitating destruction or destabilization of the RNA such that translation cannot efficiently take place. In this aspect, the invention provides a ribozyme that cleaves KSR mRNA.

The present invention naturally contemplates several means for preparation of the nucleic acids and oligonucleotides of the present invention, including as illustrated herein known recombinant techniques, and the invention is accordingly intended to cover such synthetic preparations within its scope. The knowledge of the cDNA and amino acid sequences of KSR as disclosed herein facilitates the preparation of the nucleic acids of the invention by such recombinant techniques, and accordingly, the invention extends to expression vectors prepared from the disclosed DNA sequences for expression in host systems by recombinant DNA techniques, and to the resulting transformed hosts.

Other objects and advantages will become apparent to those skilled in the art from a review of the following description which proceeds with reference to the following illustrative drawings.

BRIEF DESCRIPTION OF THE DRAWINGS

FIG. 11 depicts a comparative alignment of the mouse KSR polypeptide sequence (SEQ ID NO: 9) and human KSR polypeptide sequence (SEQ ID NO: 10).

FIG. 12. A, depicts the nucleic acid coding (cDNA) sequence of mouse ksr (SEQ ID NO: 11). B, depicts the partial nucleic acid coding (cDNA) sequence of human ksr (SEQ ID NO: 12).

FIG. 14 depicts the human KSR1 full length mRNA sequence (SEQ ID NO:24).

FIG. 15 depicts the human KSR nucleic acid and protein sequence annotated with the locations of the CA1 to CA5 domains and the target sequences for AS-ODNs. The CA1 through CA5 domains correspond respectively to SEQ ID NOS: 26, 40, 41, 42 and 43. The target amino acid sequences for AS-ODNs correspond to SEQ IDs as follows: AS-ODN3 (42-47) (SEQ ID NO:17); AS-ODN2(52-57) (SEQ ID NO: 18); AS-ODN1(63-68) (SEQ ID NO:19). The full length human KSR1 protein is predicted to have 866 amino acids.

FIG. 16 depicts the mouse KSR nucleic acid and protein sequence annotated with the locations of the CA1 to CA5 domains and the target sequences for the AS-ODNs. The CA1 through CA5 domains correspond respectively to SEQ ID NOS: 2, 44, 45, 46 and 47. The target amino acid sequences for AS-ODNs correspond to SEQ IDs as follows: AS-ODN3(51-56) (SEQ ID NO: 17); AS-ODN2(61-66) (SEQ ID NO:18); AS-ODNL(72-77) (SEQ ID NO: 19).

FIG. 17 depicts the human KSR-1 full length mRNA sequence with the nucleic acid target sequences for human AS-ODN1 through AS-ODNL12 depicted. The target nucleic acid sequences for AS-ODNs correspond to SEQ IDs as follows: AS-ODN4(1-18) (SEQ ID NO:48); AS-ODN3(124-141) (SEQ ID NO:3); AS-ODN2(154-171) (SEQ ID NO:27); AS-ODN1(187-204) (SEQ ID NO:5); AS-ODN5(205-222) (SEQ ID NO:49); AS-ODN6(247-264) (SEQ ID NO:50); AS-ODN7(298-315) (SEQ ID NO:51); AS-ODN8(321-338) (SEQ ID NO:52); AS-ODN9(351-368) (SEQ ID NO:53); AS-ODN10(379-396) (SEQ ID NO:54); AS-ODN11(5 11-528) (SEQ ID NO:55); AS-ODN12(531-548) (SEQ ID NO:56).

DETAILED DESCRIPTION

Figure 1A:
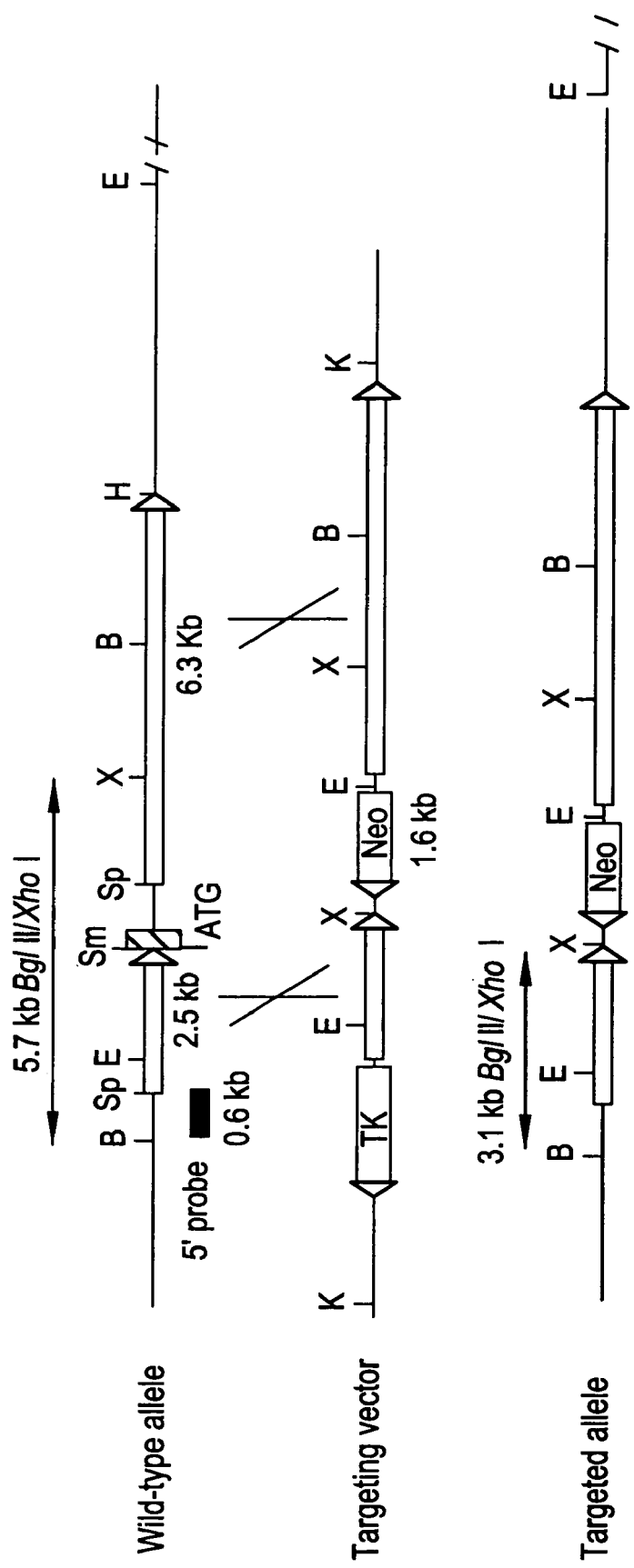
FIG. 1 depicts targeted disruption of the ksr gene in mice. A, Strategy for targeting the ksr allele. Simplified restriction maps of the 5' region of the wild-type ksr allele, the targeting vector, and the mutated allele are shown. Homologous recombination with endogenous ksr replaces an internal 1.1-kb SmaI-SpeI genomic fragment with a Neo cassette. B, Southern blot analysis of an ES clone showing the correct insertion of the targeting construct. Genomic DNA isolated from ES cells was digested with BglII and XhoI and hybridized to the 5' probe located just outside the 5' arm of the ksr targeting region as shown in A. The wild-type allele yields a 5.7-kb fragment whereas the mutant allele yields a 3.1-kb fragment. C, Genotyping of ksr$^{-/-}$ mice by PCR. The size of the PCR product is 493 bp for the wt allele and 312 bp for the mutated allele. D, Expression of ksr in wild type mouse embryos. The sizes of the two transcripts are 6.4 kb and 7.4 kb. E, Northern blot analysis of tissue ksr mRNAs. Poly-A$^+$ RNA, isolated from different tissues of adult ksr$^{+/+}$, ksr$^{+/-}$, and ksr$^{-/-}$ mice, was hybridized with a probe corresponding to domains CA2-CA4 in ksr cDNA. mRNA from NIH3T3 cells was used as control. F, KSR protein expression. Lysates prepared from wild-type and ksr$^{-/-}$ tissues were analyzed by western blot with a specific anti-KSR monoclonal antibody. Note that brain expresses the slightly shorter B-KSR1 isoform while lung and spleen express the longer KSR1 isoform. Lysates were also prepared from two independent sets of ksr$^{+/+}$ and ksr$^{-/-}$ MEFs. Equal loading was confirmed by reprobing blots with an anti-β-tubulin antibody.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S.J. Higgins, eds. (1984)]; "Animal Cell Culture" [R.I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "oligonucleotides", "antisense", "antisense oligonucleotides", "KSR ODN", "KSR antisense" and any variants not specifically listed, may be used herein interchangeably, and as used throughout the present application and claims refer to nucleic acid material including single or multiplenucleic acids, and extends to those oligonucleotides complementary to the nucleic acid sequences described herein, including as presented in FIGS. 12A, 12B and 14 and in SEQ ID NOS: 11, 12, and 24, including conserved and activity domains thereof as depicted in FIGS. 11, 15 and 16, and having the profile of activities set forth herein and in the Claims, particularly in being capable of inhibiting the expression of KSR. In particular, the oligonucleotides of the present invention may be substantially complementary to nucleic acid sequence specific to KSR, as provided in SEQ ID NO: 1 or SEQ ID NO:25, or to a portion thereof, as provided for example in SEQ ID NO: 3, 4, 5 and 28. Exemplary oligonucleotides include any of SEQ ID NOS 6-8 and SEQ ID NOS: 29-38. Accordingly, nucleic acids or analogs thereof displaying substantially equivalent or altered activity are likewise contemplated. These modifications may be deliberate, for example, such as modifications obtained through site-directed mutagenesis, or may be accidental, such as those obtained through mutations in hosts that are producers of the nucleic acids or of KSR.

$NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
| --- | --- | --- |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to conelate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage, virus, retrovirus or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to a nucleic acid of the present invention, is defined as a molecule comprised of two or more ribonucleotides, preferably more than three. Its exact size will depend upon many factors which, in turn, depend upon the ultimate function and use of the oligonucleotide. In particular, and in accordance with the present invention, the oligonucleotide should particularly associate with the RNA encoding KSR and should be of the appropriate sequence and size or length so as to specifically and stably associate with the target RNA such that expression (i.e., translation) of the RNA is blocked or such that stability of the RNA is negatively affected. In one particular aspect of the invention, the antisense oligonucleotides of the present invention are from about 8 to about 50 nucleotides in length, particularly oligonucleotides from 10 to 30 nucleotides in length, particularly oligonucleotides from 15 to 25 nucleotides.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a paiticular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA or nucleic acid sequences which code for KSR having the same amino acid sequence as the KSR sequences disclosed herein, including SEQ ID NO: 11 and SEQ ID NO: 12, but which are degenerate these sequences. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in ksr such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups

Alanine, Valine, Leucine, Isoleucine, Proline, Phenylalanine, Tryptophan, Methionine Amino Acids with Uncharged Polar R Groups Glycine, Serine, Threonine, Cysteine, Tyrosine, Asparagine, Glutamine Amino Acids with Charged Polar R Groups (Negatively Charged at Ph 6.0)

Aspartic Acid, Glutamic Acid
Basic Amino Acids (Positively Charged at pH 6.0)

Lysine, Arginine, Histidine (at pH 6.0)
Another grouping may be those amino acids with phenyl groups:

Phenylalanine, Tryptophan, Tyrosine
Another grouping may be according to molecular weight (i.e., size of R groups);

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, more preferably by at least 70 percent, most preferably by at least 90 percent, a clinically significant change in the mitotic activity of a target cellular mass, or other feature of pathology such as for example, reduced tumor mass, reduced tumor cell proliferation, reduction in metastatic capacity, or enhanced apoptosis, as may attend its presence and activity.

As used herein, "pg" means picogram, "ng" means nanogram, "ug" or "µg" mean microgram, "mg" means milligram, "ul" or "µl" mean microliter, "ml" means milliliter, "l" means liter.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The present invention relates to methods and compositions for the specific inhibition of expression and/or activity of kinase suppressor of Ras (KSR). In particular, the invention provides genetic approaches and nucleic acids for the specific inhibition of KSR. It is herein demonstrated that on specific inhibition of KSR the Ras pathway is disrupted and, specifically, that Ras-mediated tumors, tumorigenesis and metastasis regress, are inhibited, or are blocked. In particular antisense oligonucleotides and the expression of nucleic acid complementary to KSR RNA specifically inhibits expression of KSR and blocks gf Ras mediated tumorigenesis.

The present invention provides an oligonucleotide which is substantially complementary to a region of KSR RNA, wherein said oligonucleotide inhibits the expression of KSR. The invention further provides an oligonucleotide which is substantially complementary to a nucleic acid encoding mammalian KSR. In a particular embodiment, an oligonucleotide is provided which is substantially complementary to a nucleic acid encoding human KSR.

In an aspect of the invention an oligonucleotide is provided which is substantially complementary to a translation initiation site, 5' untranslated region, coding region or 3' untranslated region of mRNA encoding mammalian KSR. In one such aspect, the invention thus provides an oligonucleotide which is substantially complementary to a translation initiation site, 5' untranslated region, coding region or 3' untranslated region of mRNA encoding human KSR as provided in FIG. 14 and SEQ ID NO: 24. In a particular embodiment, the invention provides an antisense oligonucleotide substantially complementary to the N-terminal coding region of mammalian KSR mRNA, particularly to the region of nucleotides 1 through 761 of the coding region of mammalian KSR mRNA. In one embodiment, the invention includes an antisense oligonucleotide comprising a sequence substantially complementary to the CA1 region of KSR (SEQ ID NO:1 and SEQ ID NO:25). The invention provides oligonucleotides comprising a sequence substantially complementary to nucleotides encoding amino acids 33 to 72 of human KSR (SEQ ID NO:26) or 42 to 82 of mouse KSR (amino acids SEQ ID NO: 2), or a portion thereof, of the sequence of KSR.

In a further embodiment, the invention includes an antisense oligonucleotide comprising a sequence substantially complementary to nucleotides 97 to 216 of the coding sequence of human KSR (SEQ ID NO:25) corresponding to nucleotides 124 to 243 of mouse KSR (SEQ ID NO: 1), or a portion thereof. The invention provides an oligonucleotide comprising a sequence substantially complementary to nucleotides encoding amino acids 33 to 72 of human KSR (SEQ ID NO:26) and 42 to 82 of mouse KSR (SEQ ID NO: 2) or a portion thereof. In particular, oligonucleotides of the invention include oligonucleotides comprising a sequence substantially complementary to nucleotides selected from the group of: nucleotides 124 to 141 of human KSR, corresponding to nucleotides 151 to 168 of mouse KSR (SEQ ID NO: 3); nucleotides 154 to 171 of human KSR (SEQ ID NO:27), corresponding closely to nucleotides 181 to 189 of mouse KSR (SEQ ID NO: 4), with a single base change at the 5'-most nucleotide; and nucleotides 187 to 204 of human KSR, corresponding to nucleotides 214 to 231 of mouse KSR (SEQ ID NO: 5). The invention includes antisense oligonucleotides comprising a sequence selected from the group of SEQ ID NOS: 6-8 and SEQ ID NOS: 29-38.

In a particular aspect, the nucleic acids and oligonucleotides of the present invention may be modified, either by manipulation of the chemical backbone of the nucleic acids or by covalent or non-covalent attachment of other moieties. In each or any case, such manipulation or attachment may serve to modify the stability, cellular, tissue or organ uptake, or otherwise enhance efficacy of the nucleic acids and covalently linked to other molecules, including but not limited to polypeptides, carbohydrates, lipid or lipid-like moieties, ligands, chemical agents or compounds, which may serve to enhance the uptake, stability or to target the oligonucleotides.

In further embodiments, the oligonucleotides of the present invention are modified in their chemical backbone. In a particular embodiment, the oligonucleotides comprise at least one phosphorothioate linkage.

The oligonucleotides of the present invention may be combined with oligonucleotides directed to other targets, by mixture or by non-covalent or covalent attachment. For instance, the KSR antisense oligonucleotides of the present invention may be combined with antisense directed to raf as described in U.S. Pat. No. 6,391,636 (incorporated herein by reference) or to other oncogenic or proliferative proteins.

Recombinant DNA molecules comprising a nucleic acid sequence which encodes on transcription an antisense RNA complementary to mammalian KSR RNA or a portion thereof are provided by the invention. Further, the recombinant DNA molecules comprise a nucleic acid sequence wherein said nucleic acid sequence is operatively linked to a transcription control sequence. Cell lines transfected with these recombinant DNA molecules are also included in the invention.

In a further aspect, an expression vector is provided which is capable of expressing a nucleic acid which is substantially complementary to the coding sequence of KSR RNA, or a portion thereof, wherein said nucleic acid inhibits the expression of KSR. In a particular aspect, this includes an expression vector capable of expressing an oligonucleotide which is substantially complementary to the CA1 region of the coding sequence of KSR RNA, or a portion thereof, wherein said oligonucleotide inhibits the expression of KSR.

In an additional embodiment, the invention provides a composition comprising an expression vector and a pharmaceutically acceptable carrier or diluent, wherein said expression vector is capable of expressing nucleic acid which is substantially complementary to the coding sequence of KSR RNA, or a portion thereof, wherein said nucleic acid inhibits the expression of KSR.

Methods for inhibiting expression of KSR are provided. In one aspect, a method of inhibiting the expression of mammalian KSR comprising contacting cells which express KSR with an effective amount of a nucleic acid which is complementary to a portion of the mRNA encoding KSR is included. In particular, a method of inhibiting the expression of mammalian KSR is provided, comprising contacting cells which express KSR with an effective amount of the oligonucleotide of the present invention whereby expression of mammalian KSR is inhibited.

In addition, a method is provided for identifying compounds or agents which inhibit the expression of KSR comprising the steps of:

(a) incubating a cell expressing KSR in the presence and absence of a candidate compound or agent; and (b) detecting or measuring the expression of KSR in the presence and absence of a candidate compound or agent, whereby a decrease in the expression of KSR in the presence of said candidate compound or agent versus in the absence of said candidate compound or agent indicates that said compound or agent inhibits the expression of KSR.

Methods for inhibiting activity, including and preferably kinase or phosphorylation activity, of KSR are provided. In one aspect, a method of inhibiting the activity of mammalian KSR comprising contacting cells which express KSR with an effective amount of a compound or agent that inhibits or blocks KSR is included. In particular, a method of inhibiting the activity of mammalian KSR is provided, comprising contacting cells which express KSR with an effective amount of a compound, agent or composition of the present invention whereby activity of mammalian KSR is inhibited.

In addition, a method is provided for identifying compounds or agents which inhibit the activity, including kinase or phosphorylation activity, of KSR comprising the steps of:

(a) incubating a cell expressing KSR in the presence and absence of a candidate compound or agent; and (b) detecting or measuring the activity of KSR in the presence and absence of a candidate compound or agent, whereby a decrease in the activity of KSR in the presence of said candidate compound or agent versus in the absence of said candidate compound or agent indicates that said compound or agent inhibits the activity of KSR. In one aspect of the invention the activity and/or expression of KSR may be assessed or monitored by determining the phosphorylation status of the KSR kinase target or of a peptide comprising a kinase target sequence domain. For instance, the phosphorylation status of Raf or a Raf-derived peptide may be utilized in such an assessment. The activity or expression of KSR may also be assessed in vitro or in vivo in tumor cells or tumor animal models, whereby Ras mediated tumorigenesis, cell proliferation or metastasis is monitored, including as described in the Examples herein.

The present invention naturally contemplates several means for preparation of the nucleic acids and oligonucleotides of the present invention, including as illustrated herein known recombinant techniques, and the invention is accordingly intended to cover such synthetic preparations within its scope. The knowledge of the cDNA and amino acid sequences of KSR as disclosed herein facilitates the preparation of the nucleic acids of the invention by such recombinant techniques, and accordingly, the invention extends to expression vectors prepared from the disclosed DNA sequences for expression in host systems by recombinant DNA techniques, and to the resulting transformed hosts.

Another feature of this invention is the expression of the nucleic acids disclosed herein. As is well known in the art, nucleic acid or DNA sequences may be expressed by operatively linking them to an expression control sequence in an appropriate expression vector and employing that expression vector to transform an appropriate unicellular host. Such operative linking of a nucleic acid sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In addition, viral and retroviral vectors, including but not limited to adenovirus and adeno-associated virus, may be useful in such expression.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and tumor cells, transformed cells, human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins conectly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

The present invention further includes transgenic animals and animal models wherein KSR is knocked out or otherwise nullified (as in the ksr$^{-/-}$ animals described herein) or wherein KSR is overexpressed as further described herein. Such animal models include mammals for instance mice, rats, pigs, rabbits, dogs, monkeys, etc. and any other recognized vertebrate or invertebrate system for study, including ducks, fish, *drosphila, C. elegans*, etc. In the case of nullified KSR, these animals are useful for the study of oncogenesis or the blockage of tumorigenesis in a KSR null background, including to identify other factors in tumorigenesis or metastasis. In the case of KSR overexpressors, wherein tumorigenesis, cell proliferation and metastasis is enhanced, these systems may be useful for the rapid study of tumor models and for evaluating potential anti-cancer compounds or agents, including those targeting KSR as well as other pathways.

As mentioned above, nucleic acids and oligonucleotides of the present invention can be prepared synthetically rather than cloned. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule and interfering with the expression of mRNA into protein. Antisense methods have been used to inhibit the expression of many genes in vitro (Marcus-Sekura, 1988; Hambor et al., 1988).

The antisense oligonucleotides of the invention are selected as substantially complementary to a region of KSR mRNA. The oligonucleotides of the present invention may be complementary to regions including but not limited to: a) the 5'-cap site of an mRNA molecule (Ojala et al. (1997) Antisense Nucl. Drug Dev. 7:31-38); b) the transcription start site (Monia et al. (1992) J. Biol. Chem. 267:19954-19962); c) the translation initiation codon (Dean et al. (1994) Proc. Natl. Acad. Sci. U.S.A. 91:11762-11766); d) the translation stop codon (Wang et al. (1995) Proc. Natl. Acad. Sci. USA 92:3318-3322); e) mRNA splice sites (Agrawal et al. (1988) Proc. Natl. Acad. Sci. U.S.A. 86:7790-7794; Colige et al. (1993) Biochem. 32:7-11); f) the 5'-untranslated region of mRNA molecules (Duff et al. (1995) J. Biol. Chem. 270:7161-7166; Yamagami et al. (1996) Blood 87:2878-2884); g) the 3'-untranslated region of mRNA molecules (Bennett et al. (1994) J. Immunol. 152:3530-3540; Dean et al. (1994) J. Biol. Chem. 269:16146-16424); and h) the coding region (Laptev et al. (1994) Biochem. 33:11033-11039; Yamagami et al. (1996) Blood 87:2878-2884).

The skilled artisan can readily utilize any of several strategies to facilitate and simplify the selection process for nucleic acids and oligonucleotides effective in inhibition of KSR expression. Predictions of the binding energy or calculation of thermodynamic indices between an olionucleotide and a complementary sequence in an mRNA molecule may be utilized (Chiang et al. (1991) J. Biol. Chem. 266: 18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). Schmidt and Thompson (U.S. Pat. No. 6,416,951) describe a method for identifying a functional antisense agent comprising hybridizing an RNA with an oligonucleotide and measuring in real time the kinetics of hybridization by hybridizing in the presence of an intercalation dye or incorporating a label and measuring the spectroscopic properties of the dye or the label's signal in the presence of unlabelled oligonucleotide. In addition, any of a variety of computer programs may be utilized which predict suitable antisense oligonucleotide sequences or antisense targets utilizing various criteria recognized by the skilled artisan, including for example the absence of self-complementarity, the absence hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.).

In addition, antisense oligonucleotides suitable in the present invention may be identified by screening an oligonucleotide library, or a library of nucleic acid molecules, under hybridization conditions and selecting for those which hybridize to the target RNA or nucleic acid (see for example U.S. Pat. No. 6,500,615). Mishra and Toulme have also developed a selection procedure based on selective amplification of oligonucleotides that bind target (Mishra et al (1994) Life Sciences 317:977-982). Oligonucleotides may also be selected by their ability to mediate cleavage of target RNA by RNAse H, by selection and characterization of the cleavage fragments (Ho et al (1996) Nucl Acids Res 24:1901-1907; Ho et al (1998) Nature Biotechnology 16:59-630). Generation and targeting of oligonucleotides to GGGA motifs of RNA molecules has also been described (U.S. Pat. No. 6,277,981).

Inhibition of ksr gene expression can be measured in ways which are routine in the art, for example by Northern blot assay of mRNA expression or Western blot assay of protein expression as well known to the skilled artisan. Effects on cell proliferation or tumor cell growth can also be measured, in vitro or in vivo, in cell, tumor or animal model systems, by methods well known to the skilled artisan, including as taught in the examples of the instant application. Similarly, inhibition of KSR activity, particularly phosphorylation or kinase activity may be measured.

"Substantially complementary" is used to indicate a sufficient degree of complementarity such that stable and specific binding occurs between the DNA or RNA target and the oligonucleotide or nucleic acid. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression, and there is a sufficient degree of complementarity to avoid non-specific binding of the oligonucleotide to non-target sequences under physiological conditions in the case of in vivo assays or therapeutic treatment or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. Oligonucleotide includes oligomers comprising non-naturally occurring monomers, or portions thereof, which function similarly and such modified or substituted oligonucleotides may be preferred over native forms because of, for example, enhanced cellular uptake and increased stability against nucleases. The oligonucleotides of the present invention may contain two or more chemically distinct regions, each made up of at least one nucleotide, for instance, at least one region of modified nucleotides that confers one or more beneficial properties (for example, increased nuclease resistance, increased uptake into cells, increased binding affinity for the RNA target) and a region that is a substrate for enzymes capable of cleaving RNA:DNA or RNA:RNA hybrids (for example, RNase H—a cellular endonuclease which cleaves the RNA strand of an RNA:DNA duplex).

In a preferred embodiment, the region of the oligonucleotide which is modified to increase KSR mRNA binding affinity comprises at least one nucleotide modified at the 2' position of the sugar, most preferably a 2'—O-alkyl, 2'—O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. In another preferred embodiment, the oligonucleotide is modified to enhance nuclease resistance. Cells contain a variety of exo- and endo-nucleases which can degrade nucleic acids. A number of nucleotide and nucleoside modifications have been shown to confer relatively greater resistance to nuclease digestion.

Oligonucleotides which contain at least one phosphorothioate modification are presently more preferred (Geary, R. S. et al (1997) Anticancer Drug Des 12:383-93; Henry, S. P. et al (1997) Anticancer Drug Des 12:395-408; Banerjee, D. (2001) Curr Opin Investig Drugs 2:574-80). In some cases, oligonucleotide modifications which enhance target binding affinity are also, independently, able to enhance nuclease resistance.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones. The amide backbones disclosed by De Mesmaeker et al. (1995) Acc. Chem. Res. 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or.indirectly to the aza nitrogen atoms of the polyamide backbone (Nielsen et al., Science, 1991, 254, 1497). Oligonucleotides may also contain one or more substituted sugar moieties. Preferred oligonucleotides comprise one of the following at the 2' position: OH, SH, $SCH_3$, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

Oligonucleotides may also include, additionally or alternatively base modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (5-me-C) (Sanghvi, Y. S., in Crooke, S. T. and Lebleu, B., eds., Antisense Research and Applications, CRC Press, Boca Raton, 1993, pp. 276-278), 5-hydroxymethylcytosine (HMC), glycosyl HMC and gentobiosyl HMC, as well as synthetic nucleobases, including but not limited to, 2-aminoadenine, 2-thiouracil, 2-thiothymine, 5-bromouracil, 5-hydroxymethyluracil, 8-azaguanine, 7-deazaguanine (Kornberg, A., DNA Replication, W. H. Freeman & Co., San Francisco, 1980, pp75-77; Gebeyehu, G., et al., 1987, Nucl. Acids Res. 15:4513). A "universal" base known in the art, e.g., inosine, may be included.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al. (1989) Proc. Natl. Acad. Sci. USA 86: 6553), cholic acid (Manoharan et al. (1994) Bioorg. Med. Chem. Let. 4:1053), a thioether, for example, hexyl-S-tritylthiol (Manoharan et al. (1992) Ann. N.Y. Acad. Sci. 660: 306; Manoharan et al. (1993) Bioorg. Med. Chem. Let. 3: 2765), a thiocholesterol (Oberhauser et al. (1992) Nucl. Acids Res.20:533), an aliphatic chain, for example, dodecandiol or undecyl residues (Saison-Behmoaras et al. (1991) EMBO J. 10:111; Kabanov et al. (1990) FEBS Lett. 259:327; Svinarchuk et al. (1993) Biochimie 75:49), a phospholipid, a polyamine or a polyethylene glycol chain (Manoharan et al. (1995) Nucleosides & Nucleotides 14:969). Oligonucleotides comprising lipophilic moieties, and methods for preparing such oligonucleotides are known in the art, for example, U.S. Pat. Nos. 5,138,045, 5,218,105 and 5,459,255.

Farrel and Kloster (U.S. Pat. No. 6,310,047) describe the enhancement of delivery and of in vivo nuclease resistance of antisense oligonucleotides using high affinity DNA binding polynuclear platinum compounds.

It is not necessary for all positions in a given oligonucleotide to be uniformly modified, and more than one of the aforementioned modifications may be incorporated in a single oligonucleotide or even at a single nucleoside within an oligonucleotide.

The oligonucleotides in accordance with this invention preferably are from about 8 to about 50 nucleotides in length. Particularly prefelTed oligonucleotides are from 10 to 30 nucleotides in length, particularly preferred are from 15 to 25 nucleotides. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the skilled artisan. It is also well known to use similar techniques to prepare other oligonucleotides such as the phosphorothioates and alkylated derivatives.

The therapeutic possibilities that are raised by the methods and compositions, particularly oligonucleotides, of the present invention derive from the demonstration in the Examples herein that inactivation of KSR, including by genetic knockout, by inhibition of its expression utilizing antisense oligonucleotides, and by expression of reverse complement RNA or antisense DNA constructs, results in specific blockage of Ras-mediated tumorigenesis and cellular hyperproliferation, including via gf-Ras, and treatment or inhibition of progression of cancer. The present invention contemplates pharmaceutical intervention in the cascade of reactions in which overexpressed or amplified, hyperactivated or oncogenic Ras, including gf-Ras, is implicated, to regress, block, treat or inhibit the progression of Ras-mediated tumors, oncogenesis and metastasis. Thus, in instances where it is desired to reduce or inhibit Ras, including gf-Ras, the nucleic acids and oligonucleotides of the present invention could be introduced to block or inhibit the Ras pathway.

The invention further includes a method of treating or preventing a hyperproliferative condition associated with the expression of gf-Ras or heightened expression or hyperactivation of Ras or the Ras pathway in a mammal comprising administering to said mammal a therapeutically effective amount of a compound or agent which inhibits the expression or activity of mammalian KSR protein. In one aspect of this method, said compound or agent is an antisense oligonucleotide which specifically hybridizes to a portion of the mRNA encoding KSR.

A method of treating or preventing a hyperproliferative condition associated with the expression of g*f*-Ras or heightened expression or hyperactivation of Ras in a mammal is provided, comprising expressing in said mammal or administering to said mammal a therapeutically effective amount of a nucleic acid which is complementary to a portion of the mRNA encoding KSR.

In a further aspect, a method of treating or inhibiting the progression of cancer in a mammal is included, comprising administering to a mammal a therapeutically effective amount of a compound or agent which inhibits the expression or activity of mammalian KSR protein. Cancers which are susceptible to the invention's method include cancer selected from the group of pancreatic cancer, lung cancer, skin cancer, urinary tract cancer, bladder cancer, liver cancer, thyroid cancer, colon cancer, intestinal cancer, leukemia, lymphoma, neuroblastoma, head and neck cancer, breast cancer, ovarian cancer, stomach cancer, esophageal cancer and prostate cancer.

Thus, a method is provided for treating or inhibiting the progression of cancer in a mammal comprising administering to a mammal a therapeutically effective amount of one or more oligonucleotide of the present invention.

The present invention further contemplates therapeutic compositions useful in practicing the therapeutic methods of this invention. A subject therapeutic composition includes, in admixture, a pharmaceutically acceptable carrier (excipient) or diluent and one or more nucleic acid or oligonucleotide of the invention as described herein as an active ingredient. In a preferred embodiment, the composition comprises an oligonucleotide capable of inhibiting the expression of KSR.

Compositions of the nucleic acids and oligonucleotides are an additional aspect of the invention. The invention includes a composition comprising an oligonucleotide which is substantially complementary to a region of KSR RNA and a pharmaceutically acceptable carrier or diluent. The invention thus provides a pharmaceutical composition comprising a therapeutically effective amount of an oligonucleotide which is substantially complementary to a region of KSR RNA and a pharmaceutically acceptable carrier or diluent.

In a further aspect, compositions are provided comprising one or more chemotherapeutic or radiotherapeutic agent and an oligonucleotide which is targeted to a mRNA encoding mammalian KSR and which inhibits KSR expression.

The preparation of therapeutic compositions which contain nucleic acids, oligonucleotides, or analogs as active ingredients is well understood in the art. Such compositions can be prepared as injectables, either as liquid solutions or suspensions. Solid forms suitable for solution in, or suspension in, liquid prior to injection can also be prepared. The compositions may be prepared in solid pill form, including slow release formulations. The composition may be in a patch form for transdermal application, particularly in slow release format. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A nucleic acid or oligonucleotide can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammoninum, calcium, or ferric hydroxides, and such organic bases as isopropylamine, trimethylamine, 2-ethylamino ethanol, histidine, procaine, and the like.

The therapeutic nucleic acid-, oligonicleotide-, analog- or active fragment-containing compositions may be administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The therapeutic compositions may further include an effective amount of the nucleic acid or oligonucleotide, and one or more of the following active ingredients or agents: a chemotherapeutic agent, a radiotherapeutic agent, an immunomodulatory agent, an anti-mitotic agent.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absorption and distribution characteristics. U.S. Pat. No. 5,591,721 (Agrawal et al.) and may be suitable for oral administration. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intrathecal or intraventricular administration may include sterile aqueous solutions which may also contain buffers, diluents and other suitable additives. In addition to such pharmaceutical carriers, cationic lipids may be included in the formulation to facilitate oligonucleotide uptake. One such composition shown to facilitate uptake is Lipofectin (BRL Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on IC50s or EC50s in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

The oligonucleotides of the invention are also useful for detection and diagnosis of KSR expression. For example, radiolabeled oligonucleotides can be prepared by radioactive (e.g. $^{32}$P) labeling at the 5' end or 3' end (including with polynucleotide kinase), contacted with tissue or cell samples suspected of KSR expression or of gf-Ras and unbound oligonucleotide removed. Radioactivity remaining in the sample indicates bound oligonucleotide (which in turn indicates the presence of KSR or of gf-Ras) and can be quantitated using a scintillation counter or other routine means. Radiolabeled oligonucleotide can also be used to perform autoradiography of tissues to determine the localization, distribution and quantitation of KSR or gf-Ras expression for research, diagnostic or therapeutic purposes. In addition, the radiolabel may have a therapeutic effect in promoting cell death or blocking cellular proliferation. Analogous assays for fluorescent detection of raf expression can be developed using oligonucleotides of the invention which are conjugated with fluorescein or other fluorescent tag instead of radiolabeling.

The oligonucleotides of the present invention may be labeled with a detectable label. In particular aspects, the label may be selected from enzymes, chemicals which fluoresce and radioactive elements. In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re known currently available counting procedures may be utilized. In the instance where the label is an enzyme, detection may be accomplished by any of the presently utilized colorimetric, spectrophotometric, fluorospectrophotometric, amperometric or gasometric techniques known in the art. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Enzyme labels are also useful, and can be detected by any of the presently utilized colorimetric, spectrophotometlic, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known, including but not limited to peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The invention includes additional compositions which can inhibit the expression of a protein, in particular KSR, at the transcriptional level by blocking translation of KSR mRNA or by facilitating destruction or destabilization of the RNA such that translation cannot efficiently take place. In this aspect, the invention provides a ribozyme that cleaves KSR mRNA.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahlymena-type and "hammerhead"-type. (Hasselhoff and Gerlach, 1988) Tetrahlymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahlymena-type ribozymes for inactivating a specific mRNA species, and eighteen base recognition sequences are preferable to shorter recognition sequences.

The use of RNA interference strategies to inhibit the expression of KSR is further embodied in the invention. Thus, methods of RNA interference and small interfering RNA compositions are included in the methods and compositions of the present invention. RNA interference refers to the silencing of genes specifically by double stranded RNA (dsRNA) (Fine, A. et al (1998) Nature 391;806-811). In one embodiment, short or small interfering RNA (siRNA) is utilized (Elbashir, S.M. et al (2001) Nature 411:494-498). In addition, long double stranded RNA hairpins may be employed (Tavernarakis, N. et al (2000) Nature Genet 24:180-183; Chuang, C. F. and Meyerowitz, E. M. (2000) PNAS USA 97:4985-90; Smith, N A et al (2000) Nature 407:319-20). Virus-mediated RNA interference against K-Ras has been described (B rummelkamp, T.R. et al (2002) Cancer Cell 2:243-247).

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLES

These studies demonstrate that mammalian KSR integrates signaling through the EGFR/Ras/MAPK signaling module. That EGFR, Ras and KSR are on the same signaling pathway in mammalian cells is supported by the unusual hair follicle phenotype manifested in EGFR knockout mice and recapitulated in the KSR knockout, by the attenuation of EGF-induced MAPK signaling in MEFs, and by the abrogation of EGFR-/Ras-mediated tumorigenesis in multiple experimental models. Further, genetic and pharmacologic approaches identified KSR as required for various aspects of tumorigenesis in vitro and in vivo. In vitro, loss of KSR function reduced proliferation of MEFs, A431 and MCF-7 cells, abrogated Ras-mediated MEF transformation, and attenuated A431 and MCF-7 cell invasion. In vivo, inactivation of KSR antagonized v-Ha-Ras-mediated tumor formation and growth of an established EGFR-driven tumor that requires wild type Ras for neoplastic progression. As in C. elegans[2,3], KSR appears dispensable, for the most part, for normal development, but required when increased signaling through the EGFR/Ras pathway is necessary, as occurs acutely in response to EGF stimulation or chronically in Ras-mediated tumors. This suggests that pharmacologic inactivation might yield a therapeutic gain. Indeed, the results presented herein, including in vivo models of Ras-mediated tumorigenesis, show significant inhibition of cell proliferation and cell invasion on inactivation of ksr. These studies demonstrate the use of ksr antisense oligonucleotides (KSR-AS ODNs) as a therapeutic approach in cancer and tumorigenesis, particularly K-Ras mediated tumorigenesis.

Example 1

Abstract

In *Drosophila melanogaster* and *Caeniorhabditis elegans*, Kinase Suppressor of Ras (KSR) positively modulates Ras/mitogen-activated protein kinase (MAPK) signaling either upstream of or parallel to Raf[1-3]. The precise signaling mechanism of mammalian KSR, and its role in Ras-mediated transformation, however, remains uncertain. Utilizing cells markedly overexpressing recombinant KSR, some groups reported KSR inhibits MAPK activation and Ras-induced transformation[4-6] while others observed enhancing effects[7-10]. Evidence suggests these discrepancies reflect gene dosage effects[11]. To gain insight into KSR function in vivo, we generated mice homozygous null for KSR. ksr$^{-/-}$ mice are viable and without major developmental defects. Newborn mice, however, display a unique hair follicle phenotype previously observed in EGFR-deficient mice, providing genetic support for the notion that EGFR, Ras and KSR are on the same signaling pathway in mammals. Embryonic fibroblasts from ksr$^{-/-}$ animals were defective in EGF activation of the MAPK pathway, and displayed diminished proliferative potential and impaired Ras-dependent transformability. Tumor formation in Tg.AC mice, resulting from skin-specific v-Ha-ras expression, was abrogated in the ksr$^{-/-}$ background. Thus, evidence presented herein suggests KSR transduces EGFR-/Ras-mediated neoplasia, which may be potentially targeted by anti-KSR therapeutic strategies.

Introduction

Kinase suppressor of Ras (KSR) was identified in *Drosophiula melanogaster* and *Caenorhabditis elegans* as a positive modulator of Ras/mitogen-activated protein kinase (MAPK) signaling either upstream of or parallel to Raf (1-3). Although an intensive effort has been directed at elucidating the biochemical properties of mammalian KSR, its precise signaling mechanism remains uncertain. In particular, its role in Ras-mediated transformation has not been addressed convincingly. Some groups reported KSR inhibits MAPK activation and Ras-induced transformation (4-6) while others observed enhancing effects (8-10). These experiments utilized cell systems overexpressing recombinant KSR to levels far beyond endogenous KSR, and evidence suggests these discrepancies might reflect gene dosage (11). While we and others argue the necessity of both the kinase and scaffolding functions of KSR for its optimal activation of the Raf-MAPK cascade (26-30), others believe that KSR signals solely via its scaffolding function (9, 12, 31).

To gain insight into the in vivo function of KSR, we generated a mouse homozygous null for KSR. ksr$^{-/-}$ mice are viable and without major developmental defects. Newborn mice, however, display a unique hair follicle phenotype previously observed in EGFR-deficient mice. Mouse embryonic fibroblasts (MEFs) from ksr$^{-/-}$ animals displayed diminished proliferative potential and impaired oncogenic v-Ha-Ras-dependent transformation. Moreover, EGF and TPA activated the MAPK cascade to a similar extent in MEFs, yet only c-Raf-1 activation by mitogenic doses of EGF depended on ksr. The KSR knockout mouse thus allows the delineation of KSR-dependent and independent mechanisms of c-Raf-1 activation. Further, tumor formation in Tg.AC mice resulting from skin-specific v-Ha-ras expression, which utilizes MAPK signaling for transformation (32), was abrogated in the ksr$^{-/-}$ background. These defects in proliferation, transformation and tumor formation suggest KSR transduces some forms of Ras-mediated neoplasia.

Results and Discussion

Figure 1B:
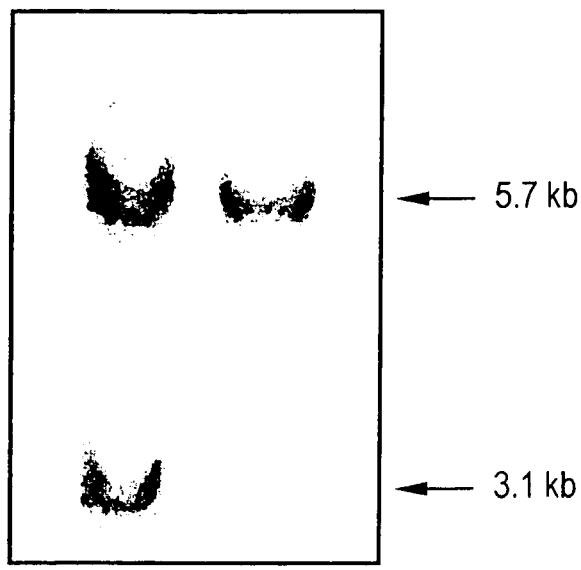
Figure 1C:
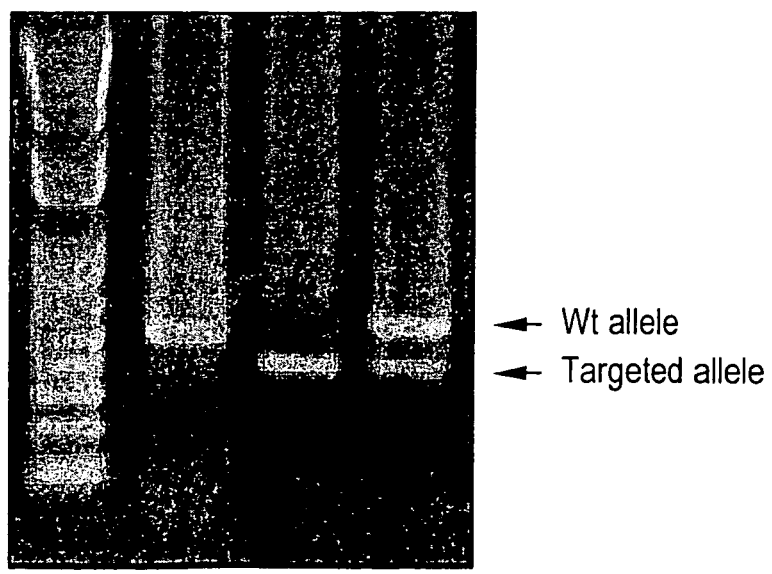

To investigate the in vivo function of KSR in mammals, we targeted the mouse ksr locus to obtain mice deficient in KSR expression. ksr$^{-/-}$ mice were generated by homologous recombination in embryonic stem (ES) cells using the pF9 targeting vector shown in FIG. 1a. The targeted region included the starting methionine (ATG codon at nt 83 in ksr cDNA) and the following 74 amino acids encompassing 85% of the KSR unique CA1 domain. Two targeted ES clones (FIG. 1b) were microinjected into C57BL/6 blastocysts and both resulted in chimeric mice that transmitted the mutated ksr allele through to the germline. Crosses of the ksr$^{+/-}$ mice generated progeny with genotypes of the expected Mendelian frequencies. A PCR-based screening strategy was developed to detect both the wild-type (wt) and mutated alleles from mouse genomic DNA (FIG. 1c).

Figure 1D:
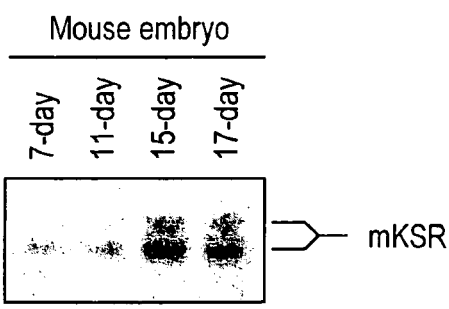
Figure 1E:
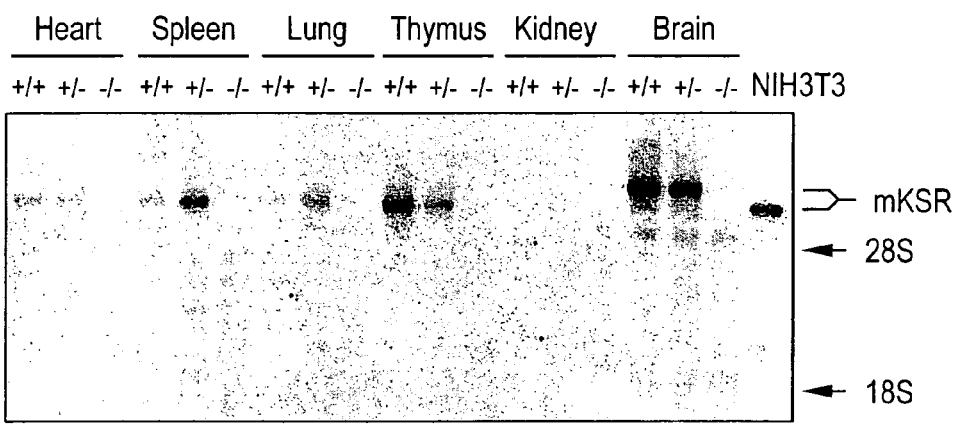
Figure 1F:
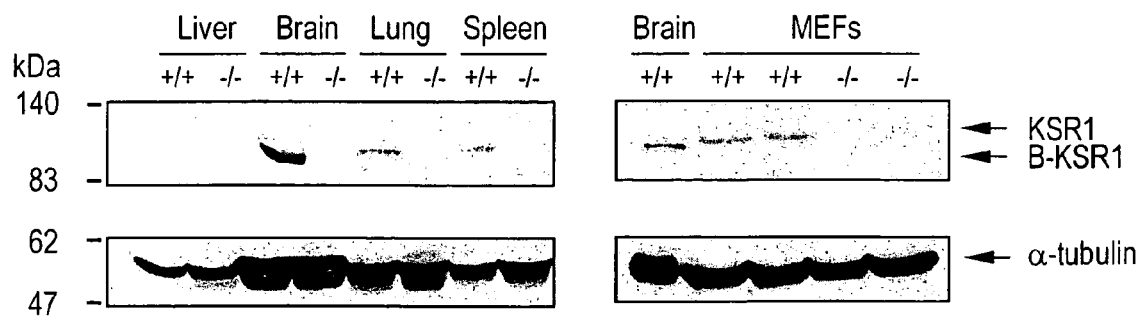

As previously reported (12), Northern blot analysis revealed wt KSR transcripts of 6.4 and 7.4 kb. The smaller transcript was detected by embryonic day 7, while the larger transcript was observed from day 11 on (FIG. 1d). In the adult, numerous tissues expressed ksr transcripts including heart, spleen, lung, thymus, and brain (FIG. 1e). Kidney displayed little if any ksr mRNA, while the larger transcript was restricted to brain. The existence of this larger mRNA was recently reported by Morrison and co-workers to represent a splice variant of murine KSR1, named B-KSR1 (12). Importantly, ksr$^{-/-}$ mice did not express detectable levels of either ksr mRNA in any tissue tested (FIG. 1e). KSR1 and B-KSR1 proteins were also not detected by Western blot analysis in tissues or in mouse embryo fibroblasts (MEFs) from ksr$^{-/-}$ mice (FIG. 1f). The lack of KSR was also confirmed by RT-PCR analysis with primers specific for the 3'-UTR of ksr cDNA (not shown). Our data thus suggest that replacement of the 5' region of ksr including the start coding site and most of the CA1 domain successfully abolished expression of both murine KSR forms.

Figure 2A:
FIG. 2 depicts skin phenotype in newborn ksr$^{-/-}$ mice. Full thickness skin cuts of 10-day old ksr$^{+/+}$, ksr$^{-/-}$ and egfr$^{-/-}$ mice were sectioned 4-6 μm thick, placed on glass slides, and stained with hematoxylin and eosin. s-serpentine, bl-blister, do-disoriented.
Figure 2B:
Figure 2C:
Figure 2D:
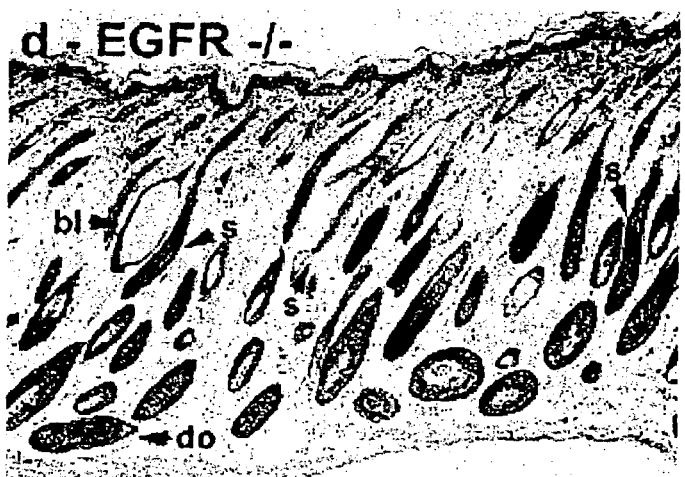

KSR knockout mice were viable and fertile, with no major developmental defects. No gross histologic abnormalities of the major organs were apparent in young mice or in adults up to one year of age. Animal weight, behavior and brood size were also unaffected in the KSR knockout. However, histologic examination of the skin of 10-day-old ksr$^{-/-}$ mice revealed noticeably fewer hair follicles, which were disorganized in dermal location (depth) and orientation (direction), and manifested asynchronous growth (FIG. 2a vs. 2b,c). Further, a significant proportion displayed a serpentine morphology (FIG. 2b). In other follicles, the inner root sheath separated from the hair shaft, resulting in formation of blisters or cysts (FIG. 2c). Strikingly, this phenotype closely resembles that found in the skin of EGFR-deficient mice (13) (FIG. 2d). Grossly, egfr$^{-/-}$ mice display short, wavy pelage hair and curly whiskers during the first weeks of age, with pelage and vibrissa hairs becoming progressively sparser and atrophic over time, eventually leading to alopecia (13). Although these gross phenotypes were not seen in ksr$^{-/-}$ mice, increased alopecia and sparse hair growth were observed following treatment with the phorbol ester 12-O-tetradecanoylphorbol 13-acetate (TPA) compared to similarly treated ksr$^{+/+}$ controls (not shown). The manifestation of this unique hair follicle phenotype by both knockouts supports the contention that EGFR and KSR might be on the same pathway in mice.

To further elucidate the effect of KSR disruption on activation of the EGFR/MAPK pathway, we generated MEFs from $ksr^{+/+}$ and $ksr^{-/-}$ littermates and evaluated their response to low, mitogenic doses of EGF and TPA, two growth stimuli known to activate the MAPK cascade. After 48 hr of serum starvation, MAPK activation in response to various doses of EGF (0.01-100 ng/ml) or TPA (10 nM-1 uM) was determined by Western blot analysis using the monoclonal and anti-phospho-p44/42 MAPK ($Thr^{202}$/$Tyr^{204}$) antibody. $ksr^{-/-}$ MEFs displayed a significant reduction in EGF- and TPA-induced MAPK (ERK½) activation at all doses examined, while total MAPK content remained largely unchanged (FIG. 3A). For EGF stimulation, inhibition of MAPK activation was manifest at doses as low as 0.01 ng/ml (not shown), whereas at 100 ng/ml EGF, MAPK activation was partially restored (FIG. 3A, upper panel, Lane 8).

Figure 3B:
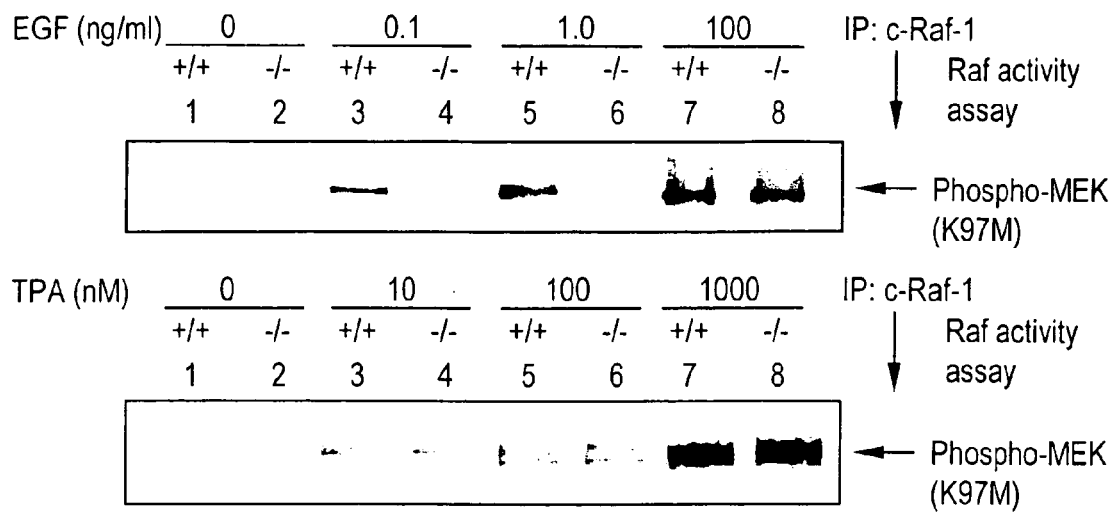
FIG. 3 depicts defects in EGF- and TPA-induced MAPK signaling and proliferation in ksr$^{-/-}$ MEFs. A, Western blot analysis of MAPK activity upon EGF and TPA treatments. Low-passage MEFs derived from $ksr^{+/+}$ and $ksr^{-/-}$ were made quiescent by 48 h incubation in serum-free medium and stimulated with low doses of EGF for 3 min(upper panel) or with TPA for 10 min (lower panel). Cells were lysed in NP40 buffer and activation of the MAPK cascade was examined by western blot with anti-phospho specific antibodies for the activated forms of MAPK(ERK1/2). Shown are representative blots from one of four independent experiments. B, Activation of endogenous Raf-1 upon EGF (upper panel) and TPA (lower panel) treatments were determined by Raf-1 activity assay as described herein in Methods. MEK1 phosphorylation was examined by western blot with anti-phospho specific antibodies for the activated forms of MEK1. Shown are representative blots from one or four independent experiments. C, Proliferation of MEFs. $0.15 \times 10^6$ $ksr^{+/+}$ or $ksr^{-/-}$ low-passage MEFs were seeded on 60 mm plates and grown as described in Methods. Cells were trypsinized every other day and counted by hemacytometer. Data (mean±SD) are compiled from three independent experiments.

To examine Raf-1 activation under conditions of MAPK inhibition, endogenous Raf-1 was evenly immunoprecipitated from all MEF lysates (not shown) and activity assayed using kinase-inactive MEK (K97M) as a substrate. While Raf-1 activity was greatly inhibited (>90%) in $ksr^{-/-}$ MEFs in response to mitogenic doses of EGF (FIG. 3B, upper panel, lanes 4 and 6), no inhibition was observed when stimulated with 100 ng/ml EGF (FIG. 3B, upper panel, lane 8). Thus, partial inhibition of MAPK activation in response to 100 ng/ml EGF in $ksr^{-/-}$ MEFs is independent of Raf-1 activation, likely resulting from the known MAK scaffolding function of KSR. These results indicate that EGF-stimulated Raf-1 activation in MEFs is dose-dependent and may occur via KSR-dependent and independent mechanisms, consistent with our previous findings (28).

The requirement for KSR for TPA-induced c-Raf-1 activation differed from that of mitogenic doses of EGF. In contrast to complete inhibition of c-Raf-1 activation after stimulation with mitogenic doses of EGF upon deletion of ksr, TPA-induced Raf-1 activation was not altered in $ksr^{-/-}$ MEFs (FIG. 3B, lower panel). Thus, the use of the KSR knockout MEFs allows for the definition of two mechanisms of c-Raf-1 activation, a KSR-dependent mechanism necessary for mitogenic EGF stimulation, and a KSR-independent mechanism used by TPA, and perhaps pharmacologic doses of EGF. Loss of KSR thuis can impact MAPK activation by two mechanisms, via loss of c-Raf-1 activation as well as the MEK scaffolding function of KSR.

Figure 3C:
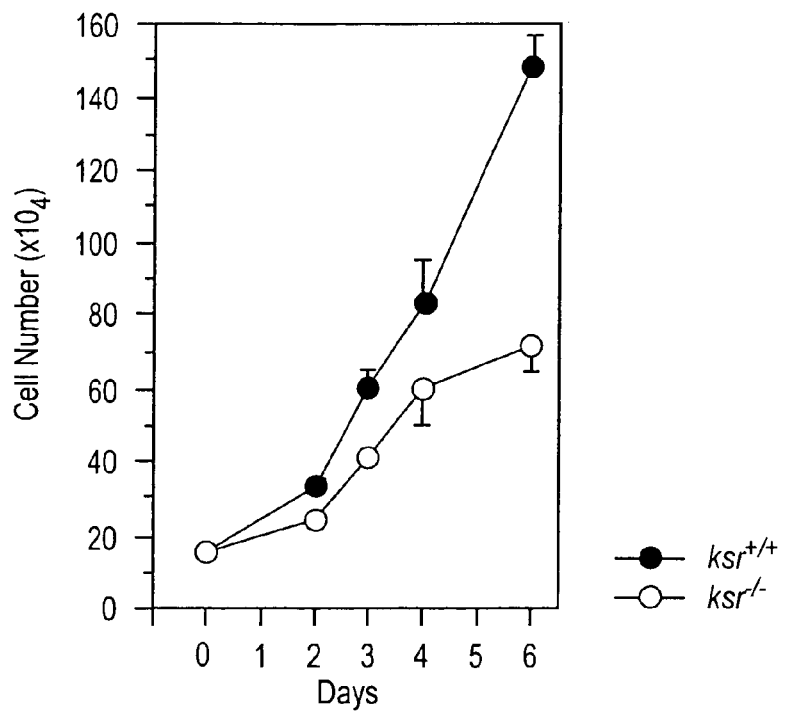

To examine the biologic consequence of MAPK inhibition on cell proliferation in vivo, a proliferation assay was performed using MEFs in the exponential phase of cell growth. Consistent with reduction in signaling through the MAPK mitogenic pathway, which provides proliferative signals, a 50% reduction in growth rate in $ksr^{-/-}$ MEFS was observed (FIG. 3C).

To determine the potential impact of KSR inactivation in Ras-mediated transformation, c-Myc and Ha-rasV12 constructs were transduced into $ksr^{+/+}$ and $ksr^{-/-}$ early-passage MEFs using high-titer retroviruses, and the ability to grow as colonies in soft agar was assessed as described (15). While $ksr^{+/+}$ fibroblasts did not form colonies in soft-agar, they did so in the presence of Myc and Ras oncogenes (not shown). In contrast, $ksr^{-/-}$ MEFs could not be transformed by Ha-rasV12, even though they were immortalized by c-Myc. Taken together, all these results show that inactivation of KSR by genetic deletion attenuates signaling through the EGFR/Ras/MAPK pathway.

The participation of oncogenic ras in human cancers is estimated to be 30% (33) and approximately 25% of skin lesions in humans involve mutations of the Ha-Ras (25% for squamous cell carcinoma and 28% for melanomas) (34,35). Since $ksr^{-/-}$ mice showed a defect in normal development of the hair follicle, presumably via impairment of EGFR signaling, we examined the role of KSR in gain-of-function Ras in the skin. For these studies, we employed Tg.AC mice, which harbor oncogenic v-Ha-ras fused to the ζ-globin promoter (16-18), a standardized model for the study of two-stage skin carcinogenesis. The v-Ha-ras transgene of Tg.AC mice is transcriptionally silent until induced in latent neoplastic cells (putative stem cells) closely associated with the outer root sheath cells of the hair follicle (19), a site consistent with our localization of KSR in mouse skin (not shown). Tg.AC mice (in FVB/N strain background) were crossed with $ksr^{-/-}$ mice (in a mixed C57BL/6:129sv background). F1 offspring heterozygous for the ksr gene were then interbred to obtain F2 offspring carrying the v-Ha-ras transgene in the $ksr^{+/+}$ and $ksr^{-/-}$ background. To determine if disruption of ksr might influence tumorigenesis in this model, we topically treated the dorsum of F2 mice twice weekly for 15 weeks with vehicle (acetone), or with 5 μg of TPA. Animals were monitored for development of skin malignancies for 20 weeks.

Figure 4A:
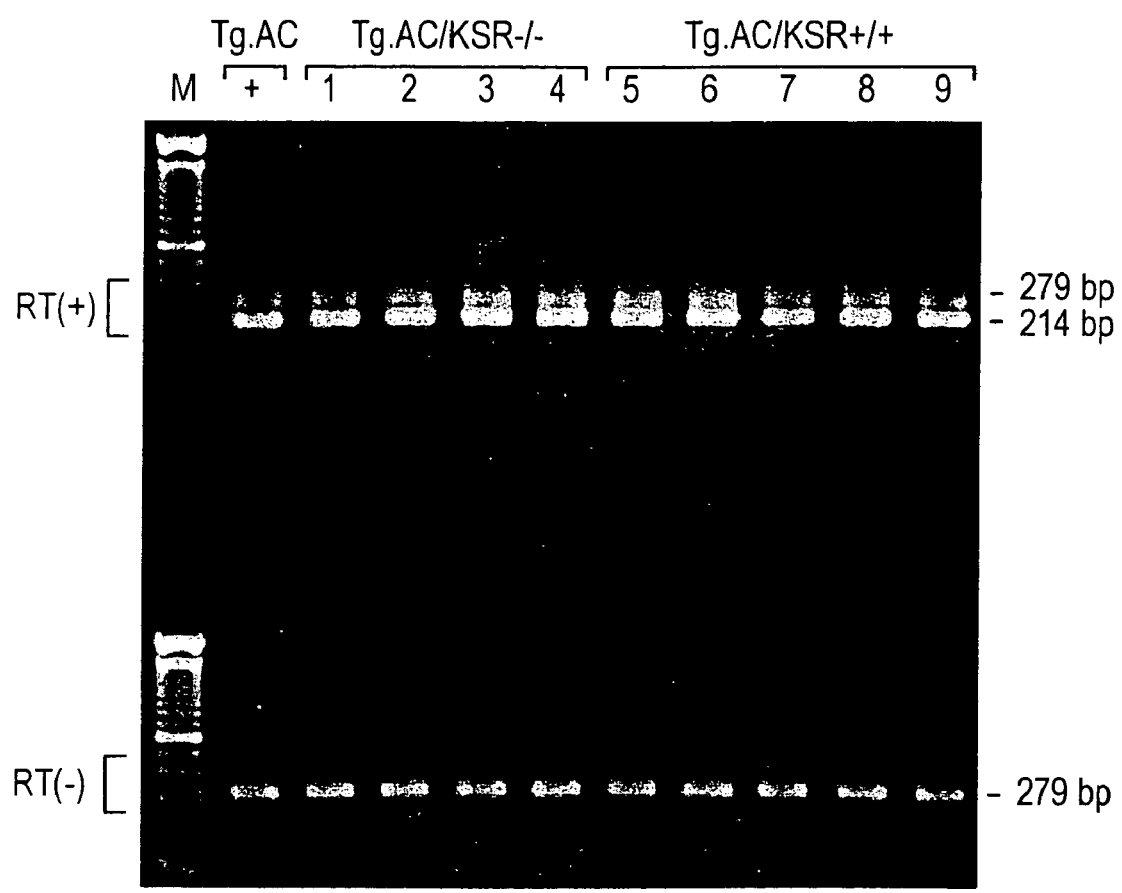
FIG. 4. Disruption of ksr gene abrogated oncogenic Ras-mediated tumorigenesis in $ksr^{-/-}$ mice. A, RT-PCR detection of v-Ha-ras expression from total RNA isolated from the epidermis of Tg.AC/$ksr^{+/+}$ and Tg.AC/$ksr^{-/-}$ mice following TPA treatment. Intron spanning primers specific for the 3'UTR region of the v-Ha-ras transgene were used. The larger 279 bp amplicon, detected in the absence of reverse transcriptase [RT(–)], is derived from DNA and unspliced RNA. The smaller 214 bp amplicon is derived from spliced mRNA and is indicative of transgene expression. B, Mice, grouped according to genotype (10/group), were treated with 5 μg of TPA twice a week for 15 weeks. Papillomas were counted weekly for 20 weeks.

Initial control studies using RT-PCR to detect the v-Ha-ras transgene mRNA showed that loss of KSR function in $ksr^{-/-}$ mice had no impact on TPA-induced expression of the oncogenic v-Ha-ras transgene in the skin (FIG. 4A). However, 70% of Tg.AC transgenic mice in a $ksr^{+/+}$ background developed papillomas, while only 10% in a $ksr^{-/-}$ background displayed papillomas (FIG. 4B). The average number of papillomas in our study was 2-4 per mouse in each group. These studies with Tg.AC mice demonstrate that genetic inactivation of KSR prevents EGFR-/Ras-mediated skin tumorigenesis.

In summary, these studies demonstrate that mammalian KSR integrates signaling through the EGFR/Ras/MAPK signaling module. That EGFR, Ras and KSR are on the same signaling pathway in mammalian cells is supported by the unusual hair follicle phenotype manifested in EGFR knockout mice and recapitulated in the KSR knockout, by the attenuation of EGF-induced MAPK signaling in MEFs, and by the abrogation of EGFR-/Ras-mediated tumorigenesis in multiple experimental models (see also Example 2). These studies further demonstrate that Raf-1 activation may occur by KSR-dependent and independent mechanisms. We believe this observation may help to resolve some of the questions regarding upstream elements of the Ras/Raf-1-MAPK module and provides new targets and reagents for additional investigation. In *C. elegans* (2,3), KSR appears dispensable, for the most part, for normal development, but required when increased signaling through the EGFR/Ras pathway is necessary and for some forms of oncogenic Ras-transduced MAPK-mediated tumorigenesis, as occurs acutely in response to EGF stimulation or chronically in Ras-mediated tumors, indicating that KSR inactivation could yield a therapeutic gain, particularly for selective abrogation of the Ras/MAPK signaling of human tumorigenesis.

Methods

Gene targeting. Mouse ksr genomic DNA clones were isolated by screening a λFixII phage library prepared from mouse strain 129/sv (Stratagene, La Jolla, Calif.) using the 5' coding region (nt 1-786) of mouse ksr cDNA (Genbank accession # U43585). The mouse ksr cDNA sequence is provided in FIG. 12A. The targeting vector pF9 was constructed by inserting a 2.5-kb SpeI-SmaI fill-in fragment from the 5' end of the mouse ksr genomic clone into the NotI fill-in site of pPGK-NTK vector (a gift from Dr. Frank Sirotnak). A 6.3-kb SpeI-HindIII fill-in fragment from the 3' downstream region of the mouse ksr genomic clone was inserted into the vector at the ClaI fill-in site. The resulting plasmid was linearized with KpnI and electroporated into 129/Sv-derived W9.5 ES cells (Chrysalis DNX Transgenic Sciences, Princeton, N.J.). Two hundred G418/Gancyclovir-resistant ES cell clones were analyzed by Southern blot using a 0.6 kb BglII-SpeI probe derived from genomic sequences located immediately outside (5') those present in pF9. This probe hybridizes to a 5.7-kb DNA fragment for the wt ksr allele and a 3.1-kb fragment from the disrupted allele. Heterozygous ES cells were microinjected into blastocyst-stage C57BL/6mouse embryos at the Sloan-Kettering Institute's Transgenic Core Facility. Injected blastocysts were then transplanted into the uterus of pseudopregnant C57BL/6 mice. Chimeric males were crossed to C57BL/6 females. Germline transmission was monitored by Southern blot in agouti F1 offspring. For mouse genotyping, genomic DNA was isolated from mouse tails with the DNeasy kit (Qiagen Inc., Valencia, Calif.) and was either digested with BglII and XhoI and examined by Southern blot as for ES cells, or analyzed by PCR amplification with two sets of primers. Primers for the wt allele were derived from the cDNA sequence of mouse ksr CA1 domain: upstream primer, 5'-TATCTCCATCGGCAGTCT-3' (SEQ ID NO:20), downstream primer, 5'-TCGACGCTCACACT TCAA-3' (SEQ ID NO:21). The primers for the mutant allele were from the sequence of the neomycin phosphotransferase gene: upstream primer, 5'-CTGACCGCTTCCTCGTG-3' (SEQ ID NO:22); downstream primer, 5'-ATAGAGC-CCACCGCATCC-3'(SEQ ID NO:23). The size of the expected product is 493-bp for the wt and 312-bp for the disrupted allele. Standard PCR conditions were employed: initial denaturation of 5 min at 94° C., followed by 30 cycles with annealing at 56° C., extension at 72° C., and denaturation at 94° C., all for 30 sec.

Northern and western blot analysis. Poly A$^+$RNA was prepared from adult mouse tissues using the Oligotex kit from Qiagen Inc. (Valencia, Calif.). The blots were hybridized with a specific $^{32}$P-labeled probe corresponding to the CA2-CA4 domains of murine ksr cDNA (1.47-kb). For embryonic tissues, we used a Mouse Embryo MTN Blot (BD Biosciences, San Diego, Calif.). Protein homogenates were prepared from ksr$^{+/+}$ and ksr$^{-/-}$ tissues, or MEFs in RIPA buffer and fractionated by SDS-PAGE (100 μg protein/lane). KSR expression was detected by western blot with a mouse monoclonal anti-KSR antibody (BD Biosciences, San Diego, Calif.) or a goat polyclonal anti-KSR antibody generated to amino acids 855 to 871 of KSR (c-19, Santa Cruz Biotechnology, Santa Cruz, Calif.). MEK and MAPK activation in MEFs were detected by western blot with anti-phospho-MEK and anti-phospho-MAPK specific antibodies: polyclonal anti-MEK, polyclonal anti-p44/42 MAPK, monoclonal anti-phospho-p44/42 MAPK (Thr$^{202}$/Tyr$^{204}$) and polyclonal anti-phosph-MEK½ (Ser$^{217}$/Ser$^{221}$) (Cell Signaling, Beverly, Calif.).

Histology. Skin tissues were collected from 10-day old ksr$^{+/+}$, ksr$^{-/-}$ and egfr$^{-/-}$ (kindly provided by Dr. Laura Hansen) mice and fixed for 15-18 hours in 10% neutral buffered formalin, washed 2 hours in 70% ethanol and embedded in paraffin blocks. The blocks were sectioned 4-6 μm thick, placed on glass slides and stained with hematoxylin and eosin.

MEF studies. MEFs, derived from ksr$^{+/+}$ and ksr$^{-/-}$ day 12-13 embryos, were prepared as described[15]. 0.25×10$^6$ early passage MEFs (PDL<6) were seeded in 6-well plates and grown in DMEM supplemented with 10% FBS for 24 h at 37° C. After 48 h in serum-free medium, cells were stimulated with 0.05-1.0 ng/ml EGF for 3 min, washed with PBS and lysed in 0.2 ml of NP-40 lysis buffer (20 mM Tris-HCl, 137 mM NaCl, 2 mM EDTA, 10% Glycerol, 1% Nonidet P-40 plus protease and phosphatase inhibitors). Raf-1 activity was performed as previously described (27). Briefly, 300 ug of total lysate was immunoprecipitated with a polyclonal anti-Raf-1 antibody (Upstate Biotechnology, Lake Placid, N.Y.), washed with NP-40 buffer containing 0.5M NaCl and incubated with the kinase-dead GST-MEK-1 (K97M). Activated MEK-1 was visualized by Western blot with a polyclonal anti-phospho-MEK antibody (Cell Signaling, Beverly, Calif.). To analyze cell proliferation, 0.15×10$^6$ ksr$^{+/+}$ or ksr$^{-/-}$ low-passage MEFs were seeded on 60 mm plates and counted at the indicated time points by hemacytometer. Data (mean+/−SD) are compiled from three independent experiments. To assess transformation capacity, MEFs from ksr$^{+/+}$ and ksr$^{-/-}$ mice were transduced sequentially with retroviral plasmids pWZL-Hygro-c-myc and pBabe-Puro-H-RasV12 (kindly provided by Scott Lowe, Cold Spring Harbor Laboratories), resuspended in 0.3% noble agar and seeded in 60 mm plates as described (15). Colonies consisting of at least 50 cells were counted after 3 weeks.

Generation of Tg.AC/ksr$^{-/-}$ mice. Homozygous male and female Tg.AC transgenic mice (16) were obtained at 3-4 week of age from Charles River Laboratories Inc. (Wilmington, Mass.). To produce the target population, ksr$^{-/-}$ mice were first bred to hemizygous Tg.AC mice containing the v-Ha-ras transgene. The resulting F1 females and males, heterozygous for ksr and hemizygous for the Tg.AC transgene, were then bred to obtain offspring in the ksr background. Nonresponder Tg.AC mice (17) were excluded from the study group. Presence of the Tg.AC transgene was determined by PCR amplification as follows: initial denaturation of 1 min 10 sec at 74° C., followed by 30 cycles with annealing at 55° C. for 1min, extension at 72° C. for 3 min, and denaturation at 94° C. for 1 min. The sequence of the Forward Primer was 5'-GGAACCTTACTTCTGTGGTGT-GAC-3' (SEQ ID NO:13), and the sequence of the Reverse Primer was 5'-TAGCAGACACTCTATGCCTGTGTG-3' (SEQ ID NO:14). PCR results were confirmed by Southern blot analysis as described (17).

Skin tumor experiments. Mice were treated twice weekly with 5 μg TPA (Sigma Chemical Company, St. Louis, Mo.) for 15 weeks and observed for papilloma development as described (16). Offspring from the original Tg.AC mice in the FVB/N background from Charles River Laboratory were used as controls. Papillomas were counted weekly for 20 weeks. v-Ha-ras transgene expression in skin after TPA treatment was assessed by nested PCR as described (24).

REFERENCES

1. Therrien, M. et al. KSR, a novel protein kinase required for RAS signal transduction. *Cell* 83, 879-88 (1995).
2. Komfeld, K., Hom, D. B. & Horvitz, H. R. The ksr-1 gene encodes a novel protein kinase involved in Ras-mediated signaling in *C. elegans*. *Cell* 83, 903-13 (1995).
3. Sundaram, M. & Han, M. The *C. elegans* ksr-1 gene encodes a novel Raf-related kinase involved in Ras-mediated signal transduction. *Cell* 83, 889-901 (1995).

4. Denouel-Galy, A. et al. Murine Ksr interacts with MEK and inhibits Ras-induced transformation. *Curr Biol* 8, 46-55 (1998).
5. Yu, W., Fantl, W. J., Harrowe, G. & Williams, L. T. Regulation of the MAP kinase pathway by mammalian Ksr through direct interaction with MEK and ERK. *Curr Biol* 8, 56-64 (1998).
6. Joneson, T. et al. Kinase suppressor of Ras inhibits the activation of extracellular ligand-regulated (ERK) mitogen-activated protein (MAP) kinase by growth factors, activated Ras, and Ras effectors. *J Biol Chem* 273, 7743-8 (1998).
7. Zhang, Y. et al. Kinase suppressor of Ras is ceramide-activated protein kinase. *Cell* 89, 63-72. (1997).
8. Xing, H., Kornfeld, K. & Muslin, A. J. The protein kinase KSR interacts with 14-3-3 protein and Raf. *Curr Biol* 7, 294-300 (1997).
9. Michaud, N. R. et al. KSR stimulates Raf-1 activity in a kinase-independent manner. *Proc Natl Acad Sci USA* 94, 12792-6 (1997).
10. Basu, S., Bayoumy, S., Zhang, Y., Lozano, J. & Kolesnick, R. BAD enables ceramide to signal apoptosis via Ras and Raf-1. *J Biol Chem* 273, 30419-26 (1998).
11. Cacace, A. M. et al. Identification of constitutive and ras-inducible phosphorylation sites of KSR: implications for 14-3-3 binding, mitogen-activated protein kinase binding, and KSR overexpression. *Mol Cell Biol* 19, 229-40 (1999).
12. Muller, J., Cacace, A. M., Lyons, W. E., McGill, C. B. & Morrison, D. K. Identification of B-KSR1, a novel brain-specific isoform of KSR1 that functions in neuronal signaling. *Mol Cell Biol* 20, 5529-39 (2000).
13. Hansen, L. A. et al. Genetically null mice reveal a central role for epidermal growth factor receptor in the differentiation of the hair follicle and normal hair development. *Am J Pathol* 150, 1959-75. (1997).
14. Wennstrom, S. & Downward, J. Role of phosphoinositide 3-kinase in activation of ras and mitogen-activated protein kinase by epidermal growth factor. *Mol Cell Biol* 19, 4279-88 (1999).
15. Serrano, M., Lin, A. W., McCurrach, M. E., Beach, D. & Lowe, S. W. Oncogenic ras provokes premature cell senescence associated with accumulation of p53 and p16INK4a. *Cell* 88, 593-602 (1997).
16. Leder, A., Kuo, A., Cardiff, R. D., Sinn, E. & Leder, P. v-Ha-ras transgene abrogates the initiation step in mouse skin tumorigenesis: effects of phorbol esters and retinoic acid. *Proc Natl Acad Sci USA* 87, 9178-82 (1990).
17. Kantz, D. C., Lacks, G. D. & Cannon, R. E. Chemiluminescence-based method for genotyping Tg.AC responder mice. *Biotechniques* 27, 278-80 (1999).
18. Humble, M. C. et al. Radial transformation-associated recombination cloning from the mouse genome: isolation of Tg.AC transgene with flanking DNAs. *Genomics* 70, 292-9. (2000).
19. Hansen, L. A. & Tennant, R. W. Follicular origin of epidermal papillomas in v-Ha-ras transgenic TG.AC mouse skin. *Proc Natl Acad Sci USA* 91, 7822-6. (1994).
20. Merlino, G. T. et al. Amplification and enhanced expression of the epidermal growth factor receptor gene in A431 human carcinoma cells. *Science* 224, 417-9. (1984).
21. Ogiso, Y., Sakai, N., Watari, H., Yokoyama, T. & Kuzumaki, N. Suppression of various human tumor cell lines by a dominant negative H-ras mutant. *Gene Ther* 1, 403-7. (1994).
22. Cotter, F. E. et al. Antisense oligonucleotides suppress B-cell lymphoma growth in a SCID-hu mouse model. *Oncogene* 9, 3049-55. (1994).
23. Agrawal, S., Temsamani, J. & Tang, J. Y. Pharmacokinetics, biodistribution, and stability of oligodeoxynucleotide phosphorothioates in mice. *Proc Natl Acad Sci USA* 88, 7595-9. (1991).
24. Battalora, M. S. et al. Age-dependent skin tumorigenesis and transgene expression in the Tg.AC (v-Ha-ras) transgenic mouse. *Carcinogenesis* 22, 651-9. (2001).
25. Xing, R. H., Mazar, A., Henkin, J. & Rabbani, S. A. Prevention of breast cancer growth, invasion, and metastasis by antiestrogen tamoxifen alone or in combination with urokinase inhibitor B-428. *Cancer Res* 57, 3585-93. (1997).
26. Wang, X and Studzinski, G. P, Phosphorylation of raf-1 by kinase suppressor of ras is inhibited by "MEK-specific" inhibitors PD 098059 and U 0126 in differentiating HL60 cells, Exp Cell Res. 268:294-300, 2001.
27. Xing, H, R., Lozano, J., and Kolesnick, R. Epidermal growth factor treatment enhances the kinase activity of kinase suppressor of Ras, J Biol Chem. 275:17267-80, 2000.
28. Xing, H. R. and Kolesnick R. Kinase suppressor of Ras signals through Thr269 of c-Raf-1, J Biol Chem. 276: 9733-41., 2001.
29. Yan, F., John, S. K., and Polk, D. B. Kinase suppressor of Ras determines survival of intestinal epithelial cells exposed to tumor necrosis factor, Cancer Res. 61:8668-75., 2001.
30. Yan, F. and Polk, D. B. Kinase suppressor of ras is necessary for tumor necrosis factor alpha activation of extracellular signal-regulated kinase/mitogen-activated protein kinase in intestinal epithelial cells, Cancer Res. 16:963-9., 2001.
31. Roy, F., Laberge, G., Douziech, M., Ferland-McCollough, D., and Therrien, M. KSR is a scaffold required for activation of the ERK/MAPK module, Genes Dev. 16:427-38., 2002.
32. Hamilton, M. and Wolfman, A. Oncogenic Ha-Ras-dependent mitogen-activated protein kinase activity requires signaling through the epidermal growth factor receptor, J Biol Chem. 273:28155-62., 1998.
33. Almoguera, C., Shibata, D., Forrester, K., Martin, J., Arnheim, N., and Perucho, M. Most human carcinomas of the exocrine pancreas contain mutant c-K-ras genes, Cell. 53:549-54., 1988.
34. Bos, J., L. ras oncogenes in human cancer: a review, Cancer Res. 49:4683-9., 1989.
35. Migley, R. S. and Kerr, D. J. Ras as a target in cancer therapy, Crit Rev Oncol Hematol. 44:109-20., 2002.

Example 2

Abstract

Given the prevalence of oncogenic ras mutations in human cancers, selective inactivation of gain-of-function (g$f$) Ras signaling represents a highly attractive therapeutic approach, although it has not been achieved clinically. Here, g$f$ Ras signaling was targeted indirectly via genetic or pharmacologic inactivation of Kinase Suppressor of Ras1 (KSR1), an immediate downstream effector selective for g$f$ Ras. KSR1 inactivation abrogated g$f$ Ras-mediated tumorigenesis induced by constitutively activated epidermal growth factor receptor or oncogenic K-Ras mutation in several human tumor cell lines and in nude mice xenografts.

Inhibition of ksr1 via continuous infusion of KSR antisense oligonucleotides (AS-ODNs) prevented growth of oncogenic K-ras-dependent human PANC-1 pancreatic and A549 non-small-cell lung carcinoma (NSCLC) xenografts in nude mice, effected regression of established PANC-1 tumors, and inhibited A549 lung metastases, without apparent toxicity. These studies suggest KSR AS-ODNs as a treatment for gf Ras-dependent human malignancies, in particular pancreatic cancer for which there is presently no effective curative therapy.

Introduction

Adenocarcinoma of the exocrine pancreas represents the fourth-leading cause of cancer-related mortality in Western countries. Treatment has had limited success and the five-year survival remains less than 5% with a mean survival of 4 months for patients with surgically unresectable tumors (1,2). While oncogenic activation of H-, K-, and N-Ras arising from single nucleotide substitutions has been observed in 30% of human cancers (5), over 90% of human pancreatic cancer manifest the codon 12 K-ras mutation (3-5). This point mutation can be identified early in the course of the disease when normal cuboidal pancreatic ductal epithelium progresses to a flat hyperplastic lesion, and is considered causative in the pathogenesis of pancreatic cancer (6,7). The regulation of oncogenic K-ras signaling in human pancreatic cancer, however, remains largely unknown. While various therapeutic strategies have been developed to inactivate key components of the Ras-Raf-MAPK cascade, specific inhibition of gf Ras action has not been achieved clinically (8,9).

Recent studies demonstrated that Kinase Suppressor of Ras (KSR1) positively modulates the Ras/MAPK signaling arm of the EGFR/Ras pathway. KSR1 acts downstream of Ras, either upstream of or parallel to Raf in *Drosophila* and *C. elegans* (10-12). Mammalian forms of KSR1, identified on the basis of sequence homology (12), suggest that KSR signaling is evolutionarily conserved. The precise mechanisms of mammalian KSR signaling and its biological functions, however, remain largely unknown. Genetic studies from ksr1-deficient *C. elegans* and mice demonstrate that while ksr1 is dispensable for normal development (10,11, 13), it may be obligate for gfRas signaling through the MAPK cascade (see Example 1 above). In *C. elegans*, KSR loss-of-function (lf) reverts the gf Ras-mediated multivulva phenotype (10,11) caused by the same codon 13 mutation that confers oncogenic potential onto mammalian Ras.

To elucidate the role of KSR1 in Ras-mediated human malignancies, especially in pancreatic cancer, and to explore the feasibility of employing KSR1 as a therapeutic target, antisense approaches were employed to genetically and pharmacologically inactivate mammalian ksr1. We report here that both approaches to KSR1 inactivation abrogated gf Ras signaling of tumoligenesis, either via constitutively activated EGFR or oncogenic K-Ras mutation. Further, antisense-mediated inhibition of ksr1 gene expression via continuous infusion of KSR AS-ODNs prevented the onco-genic K-ras-dependent growth of human PANC-1 pancreatic and A549 non-small-cell lung carcinoma (NSCLC) xenografts in nude mice, elicited regression of established PANC-1 tumors, and inhibited A549 lung metastases without apparent toxicity. These studies demonstrate that KSR AS-ODNs might represent a tumor-specific therapeutic agent for the treatment of oncogenic K-ras-dependent human malignancies.

Results

Inhibition of ksr1 gene expression induces morphologic chances in A431 cells.

Figure 5A:
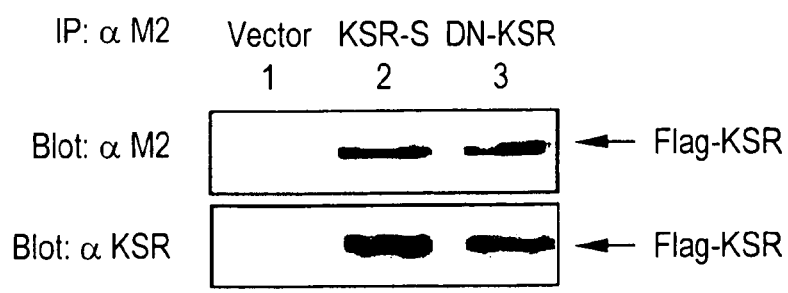
FIG. 5. Inducible A431-Tet-Off-pTRE-KSR cells. A and B, Western blot analysis of wild type Flag-KSR-S and Flag-DN-KSR expression (A), and inhibition of endogenous KSR1 expression by KSR-AS (B). Flag-KSR-S and DN-KSR were immunoprecipitated (IP) with the monoclonal anti-Flag (M2) antibody and detected by WB. The identity of Flag-KSR was confirmed by re-probing with a monoclonal anti-KSR antibody (BD Biosciences). Endogenous KSR1 was immunoprecipitated as described in Methods and detected as above. C, Dose-dependent inhibition of Flag-KSR-S expression by doxycycline. KSR-S cells were treated with indicated doses of Dox for 24 h and Flag-KSR-S expression after Dox treatment was determined by WB as above. D and E, Inactivation of KSR1 by KSR-AS or DN-KSR leads to alterations in morphology (D), and the development of a multinuclei phenotype (E). A431-pTRE cells were examined under the phase-contrast microscope and photographed at 20× magnification for cell morphology (D) and 40× magnification for multinucleation (E).
Figure 5B:
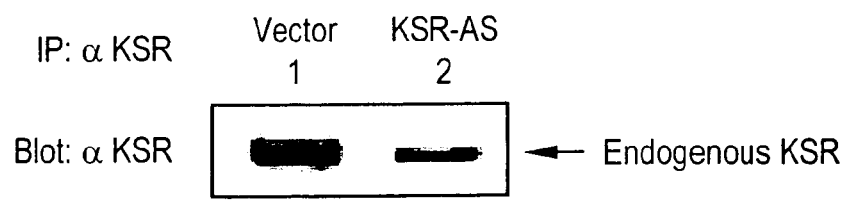
Figure 5C:
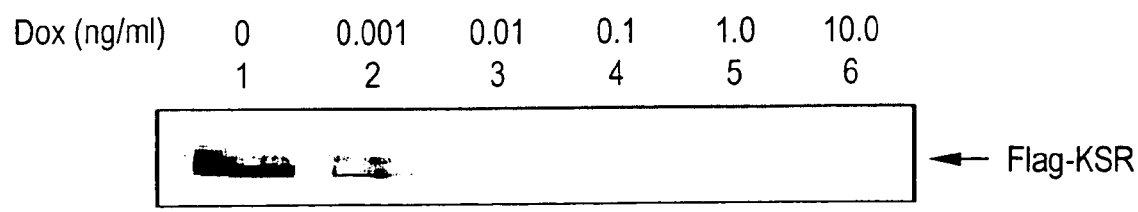

In *C. elegais*, KSR1 regulates gf Ras signaling of vulval development, a pathway initiated through LET-23, the EGFR homolog (10,11). To explore the role of mammalian KSR1 in EGFR-mediated tumorigenesis, we employed the A431 human epidermoid carcinoma tumor line in which tumor growth is driven through wild type Ras by a 100-fold excess of activated EGFR/HER1 ($10^7$ receptors/cell) (14). We generated A431 cell lines stably expressing inducible forms of wild type KSR1 (KSR-S), antisense KSR1 (KSR-AS) and dominant negative KSR1 (DN-KSR) using the Retro-Tet-Off system. While Flag-tagged KSR-S and DN-KSR were expressed to similar levels (FIG. 5A), stable expression of the KSR-AS resulted in a 60% reduction of endogenous KSR expression (FIG. 5B). Further, doxycycline (Dox) treatment elicited a dose-dependent inhibition of KSR-S expression (FIG. 5C), and Dox withdrawal following its addition effectively restored KSR-S expression (not shown). Similar results were found in the DN-KSR and KSR-AS cells (not shown). These observations indicate that the KSR-Tet-Off system is tightly regulated by Dox.

The effect of manipulating KSR1 levels on the morphology of stably transfected A431 cells was examined first. While non-transfected (not shown), vector-transfected and KSR-S-transfected A431 cells displayed the similar cobblestone morphology of poorly differentiated squamous epithelial cells (FIG. 5D), abrogation of ksr1 expression by KSR-AS produced a marked change in cell morphology. The KSR-AS cell somata gradually enlarged and flattened, cytoplasmic processes retracted, and cells grew in a more scattered pattern (FIG. 5D). Further, these cells became multinucleated (FIG. 5E), indicative of the failure to complete cytokinesis with a resultant proliferation defect (see below) (15). Phase-contrast microscopy reveals that while over 80% of KSR-AS cells contained multiple nuclei, multinucleated cells were rarely seen (<8%) in control or KSR-S cells. Similar morphologic changes were observed in DN-KSR cells (FIG. 5D and SE) indicating that inhibition of ksr1 gene expression in A431 cells might have profound effects on EGFR-mediated biological events in this tumor cell line.

Figure 6A:
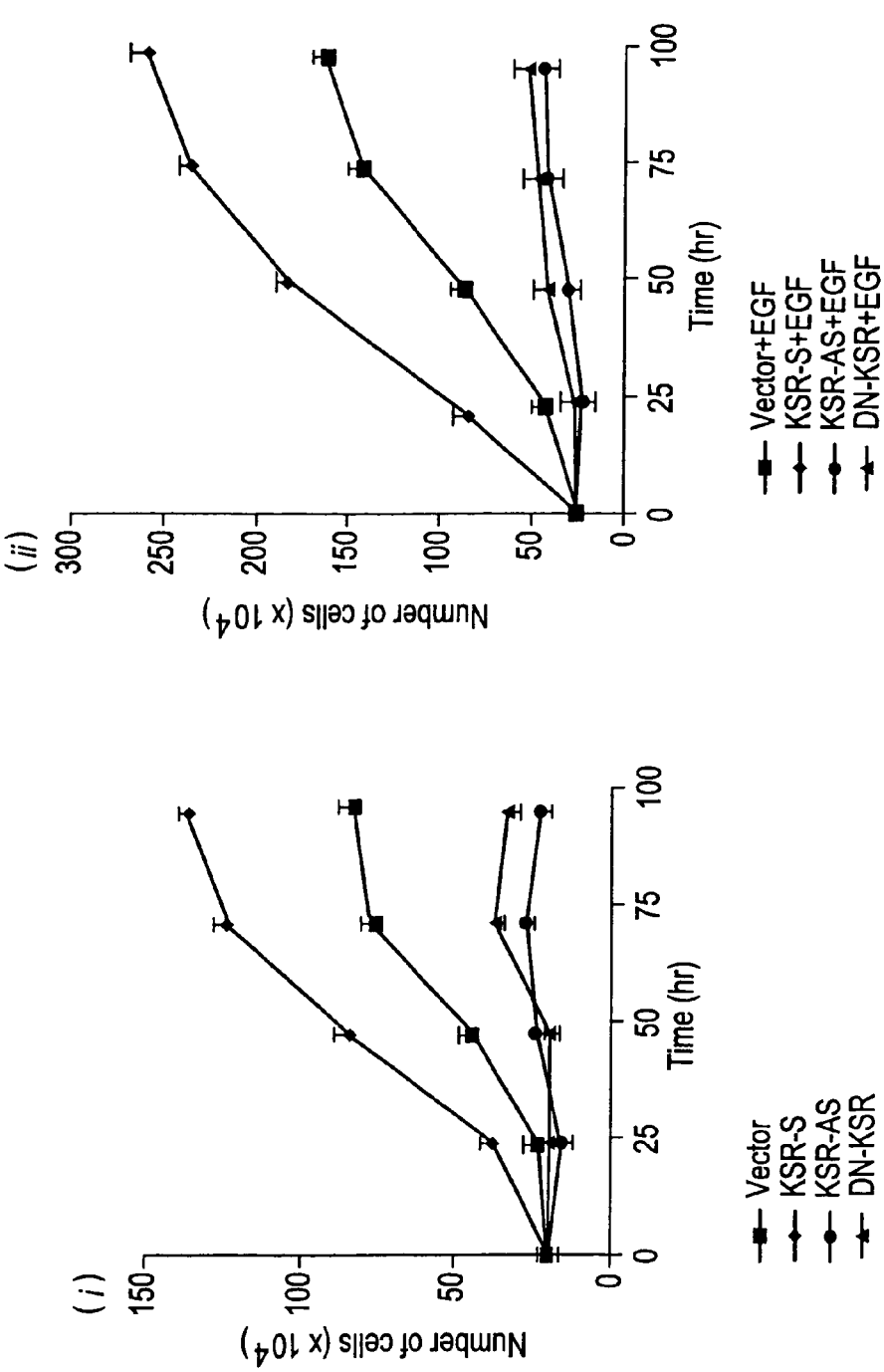
FIG. 6. Inactivation of KSR1 abolishes EGF-stimulated biological responses in A431 cells. A, Cell proliferation assay without (i) and with (ii) EGF stimulation. Proliferation assays were performed as described in Methods. B, Cell cycle distribution of A431-pTRE cells was determined by FACS analysis as described in Methods. The proportion of cells in the different phases of the cell cycle was calculated from the experimental fluorescence histograms. C, Matrigel invasion assay in response to EGF stimulation. To optimize the stimulatory effect of overexpression of KSR-S on A431 cell invasion, the assay was terminated after 12 h (i). To maximize the inhibitory effect of KSR-AS and DN-KSR on A431 cell invasion, the assay was terminated after 18 h (ii). D, Soft agar colony formation assays in response to EGF stimulation were performed as in Methods. For each cell line or treatment, 4 plates were counted. These results represent one of four similar studies.
Figure 6C:
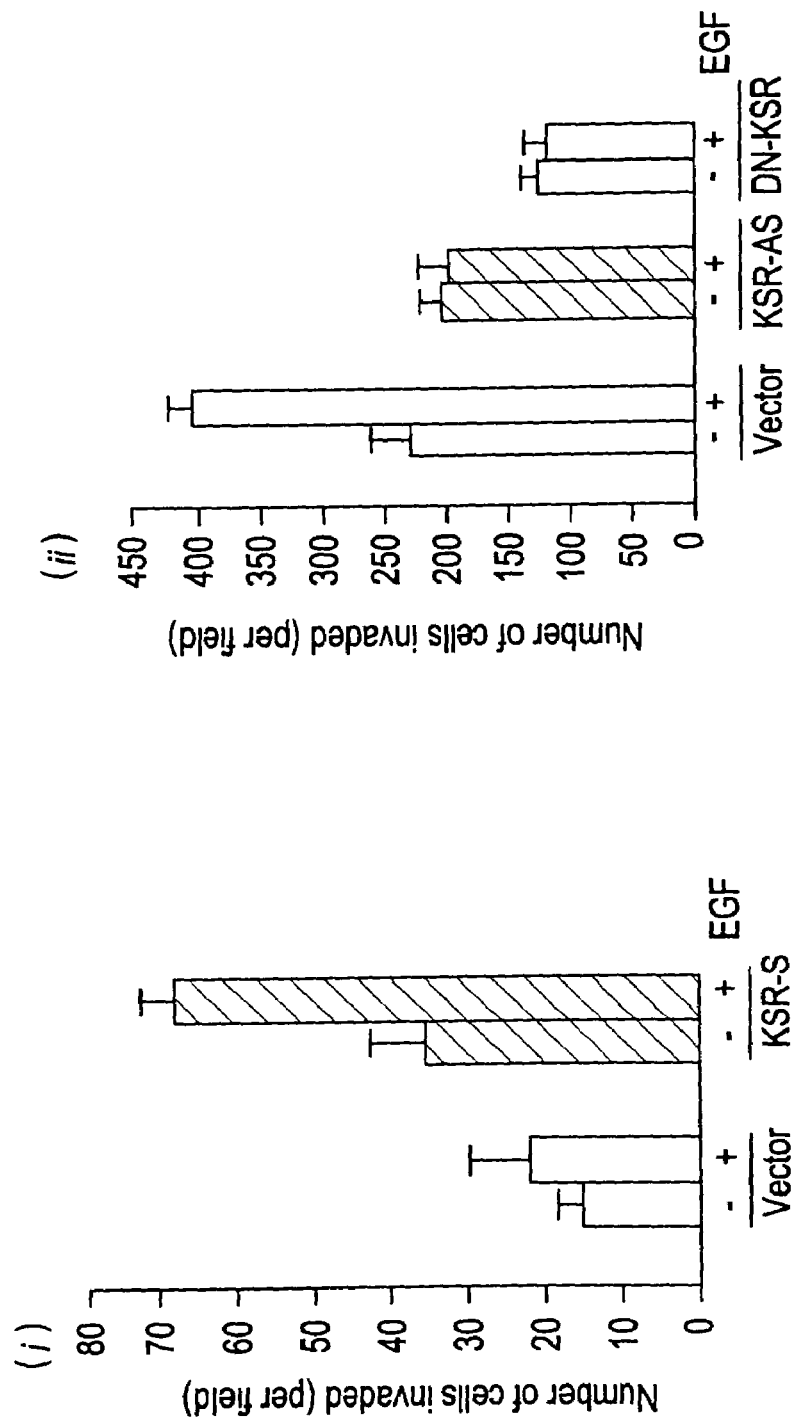
Figure 6D:
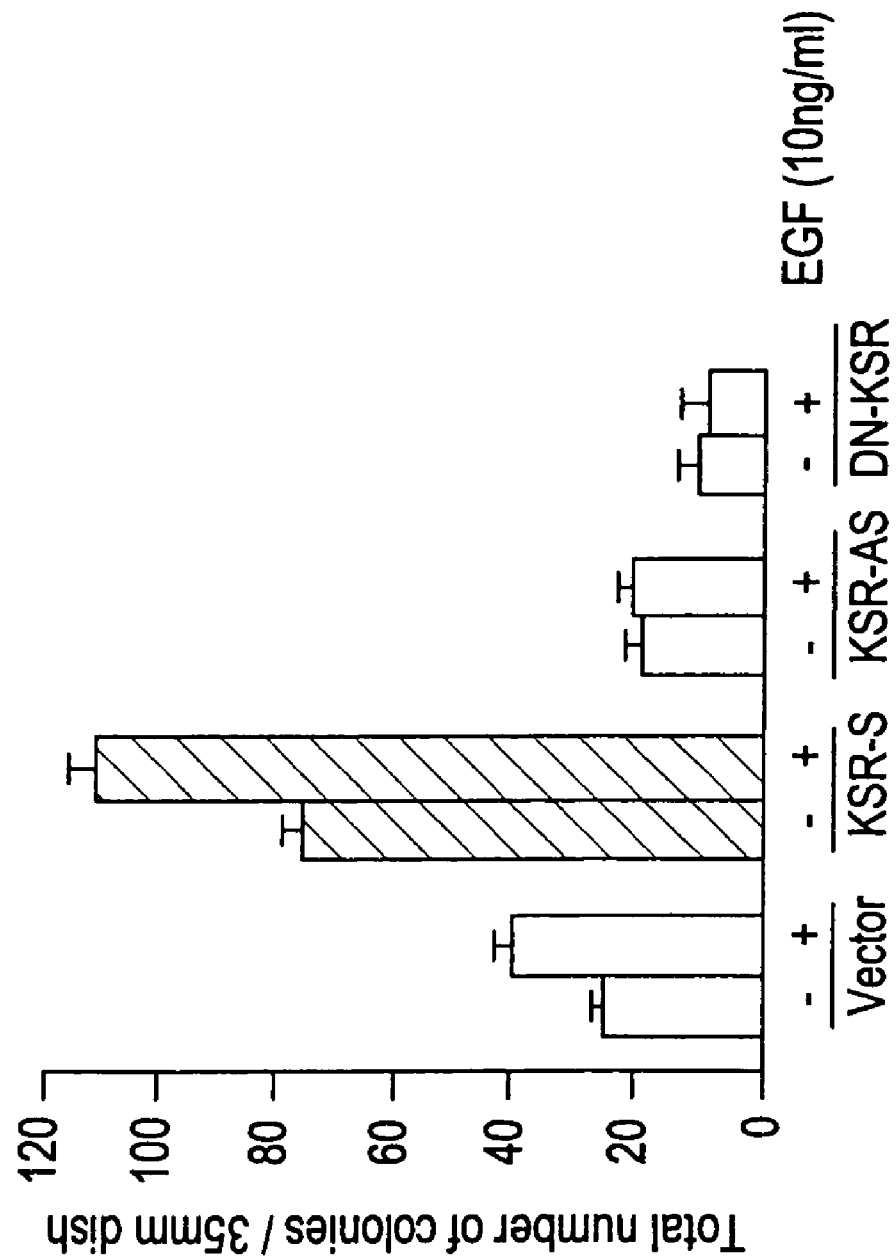

Inhibition of ksr1 oene expression attenuates A431 tumorigenesis. To assess the consequences of KSR1 inhibition on the malignant properties of A431 cells and their response to EGF in vitro, cell proliferation, invasion and transformation assays were performed. When KSR-S was overexpressed by A431 cells, both baseline and EGF-stimulated proliferation (FIG. 6A), invasion (FIG. 6C) and transformation (FIG. 6D) were markedly enhanced. In contrast, depletion of ksr1 expression in KSR-AS cells resulted a significant inhibition of baseline proliferation, invasion and transformation (FIG. 6, p<0.05 in each case), and the abrogation of EGF responses (FIG. 6). The DN-KSR effect was similar to that observed with KSR-AS (FIG. 6).

Consistent with the observed alterations in cell growth, KSR significantly impacted cell cycle distribution as determined by FACS analysis (FIG. 6B). While there was a significant elevation of S-phase cells in exponentially growing KSR-S cells, a sharp reduction in S-phase cells coupled with a concomitant increase of G2/M-phase cells was observed in KSR-AS cells compared to vector-transfected controls (p<0.05 in each case). These observations were confirmed by Ki-67 staining (not shown). The specificity of KSR-S and KSR-AS in mediating stimulation and inhibition, respectively, of proliferation, invasion and transformation was confirmed by turning off the KSR-S and KSR-AS expression by Dox treatment (not shown). These observations demonstrate that while overexpression of KSR enhanced the neoplastic properties of A431 cells, inactivation of KSR by KSR-AS or DN-KSR rendered A431 cells less malignant.

Figure 7A:
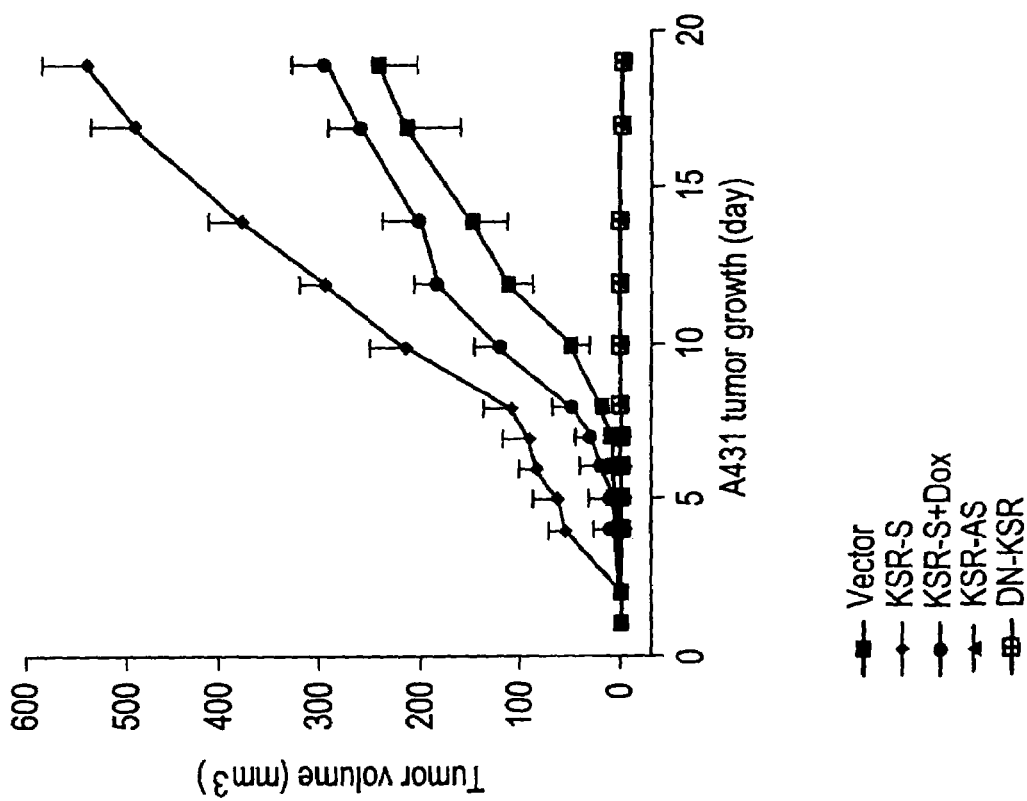
FIG. 7. Inactivation of KSR1 prevents A431 tumorigenesis. A, Growth curve of A431 tumors. $10^6$ A431-pTRE cells were injected s.c. into nude mice as described in Methods. To determine the specificity of KSR-S on A431 tumorigenesis, Dox (100 mg/ml) was added to the drinking water of a group of KSR-S tumor-bearing mice (KSR-S+Dox) 3 days prior to tumor implantation and continued throughout the experiment to turn off KSR-S expression. Mice receiving KSR-AS and DN-KSR cells were monitored up to 120 days. These results represent one of three similar experiments. There were 5 mice in each experimental group. B, H&E staining of A431 tumors. Formalin-fixed, paraffin-embedded and 5 mm-cut A431-pTRE tumor sections were stained with H&E as described in Methods. Black arrows in (i) and (ii) indicate squamous differentiation. Black arrows in (iii) and (iv) indicate multinucleated tumor cells, and (v) is the enlargement of the framed field in (iii) of a multinucleated cell.
Figure 7B:
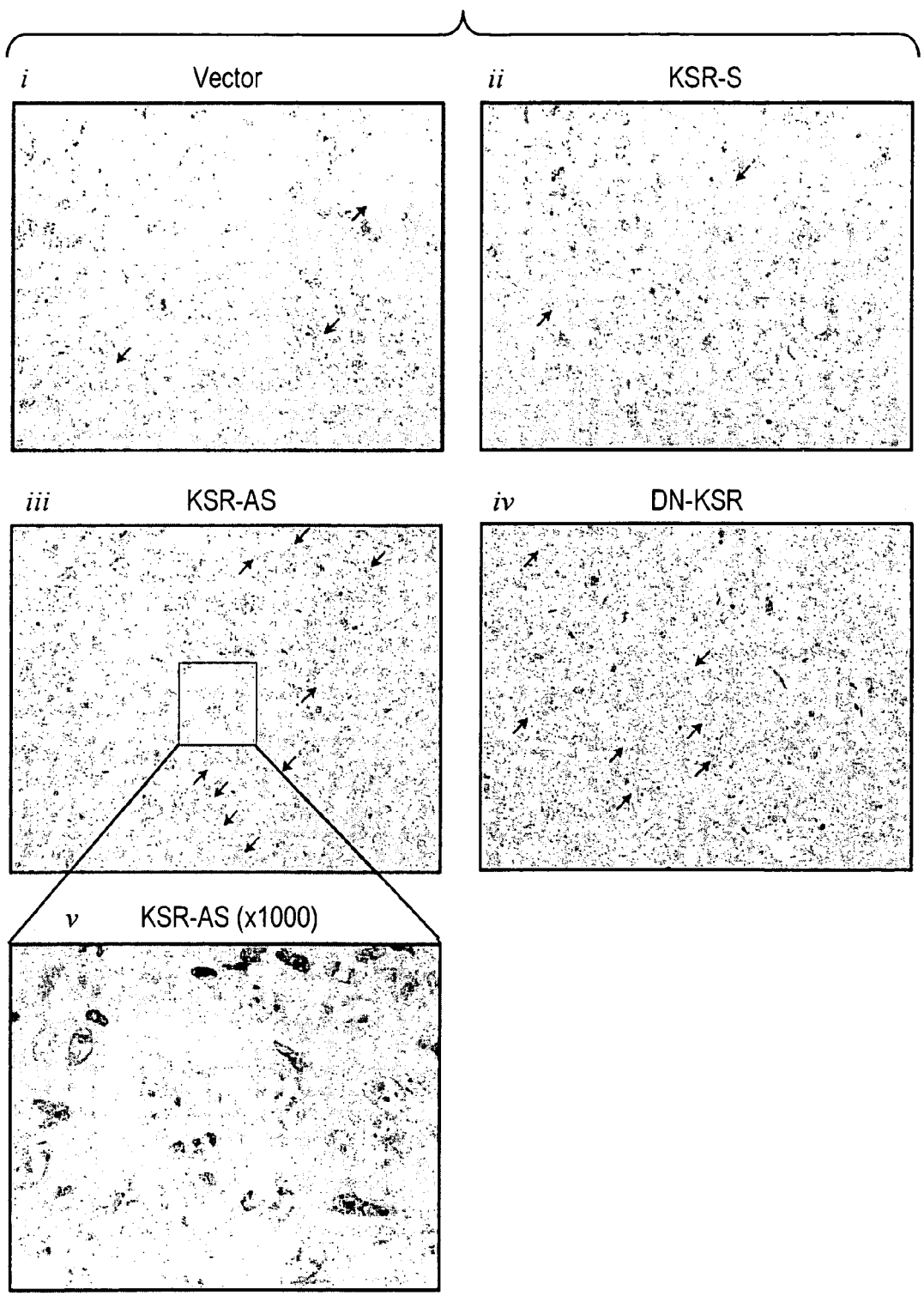

To elucidate whether KSR1 down-regulation might have a similar anti-proliferative effect in vivo, $10^6$ KSR-S, KSR-AS, DN-KSR or vector-transfected A431 cells were injected subcutaneously (s.c.) into the right flank of immunodeficient (nude) mice. While tumor take was 100% in mice receiving KSR-S and vector-transfected cells, KSR-S tumors had an earlier onset (FIG. 7A, left-shifted growth curve, $p<0.05$), were 200% larger in size on day 25, and had 2.5-fold more Ki-67 positive cells than vector-transfected tumors of the comparable size (not shown). Examination of tumor specimens removed on day 25 revealed continued expression of Flag-KSR-S (not shown). The specificity of KSR-S in mediating these effects was confirmed by feeding a group of KSR-S tumor-bearing mice with Dox-containing water which shut off tumoral KSR-S expression efficiently (not shown), and almost completely prevented the growth stimulatory effect of KSR-S on A431 tumors (FIG. 7A, KSR-S vs. KSR-S+Dox, $p<0.01$). In contrast, mice injected with $10^6$ A431 KSR-AS or DN-KSR cells failed to develop any tumors when observed up to 120 days (FIG. 7A and not shown). When the inocula size was increased to $10\times10^6$ and prepared in 50% Matrigel, only 1 out of 20 mice in each case developed a late onset (day 42 for KSR-AS and day 36 for DN-KSR) slow growing tumor. Further, squamous differentiation was evident in both the vector- and KSR-S tumors (FIG. 7B (i) and (ii), black arrows), although KSR-S tumors had less kertohyalin granules and a higher mitotic index (not shown). In contrast, squamous differentiation was absent from KSR-AS and DN-KSR tumors (FIG. 7B (iii) and (iv)). Moreover, consistent with our observations in vitro, 25% of the KSR-AS and 18% of the DN-KSR tumor cells were multinucleated in vivo (FIG. 7B (iii) and (iv), black arrows, and (v)).

Figure 8C:
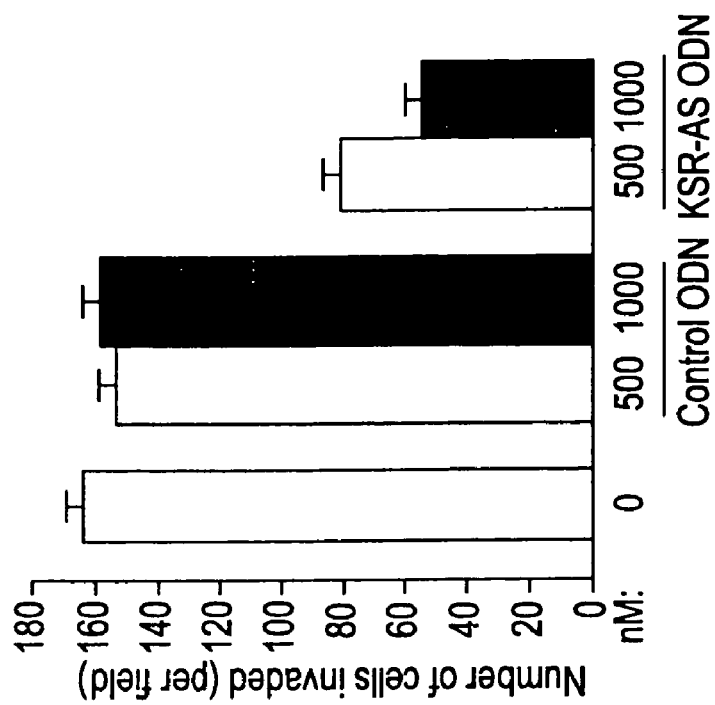
FIG. 8. Inactivation of KSR1 by AS-ODN attenuates A431 tumorigenesis. A, Immunofluorescence staining of endogenous KSR1 expression after treatment with 1 mM Control- or AS-ODNs was performed as in Methods. Nuclei were counter stained with DAPI. To compare the intensity of fluorescence labeling, all images of KSR expression were taken with the same exposure time. B and C, Dose-dependent inhibition of A431 cell proliferation (B) and invasion (C) by AS-ODN treatment. For the proliferation assay, 30% confluent A431 cells were treated with the indicated doses of Control- or AS-ODNs as in FIG. 3. Cell proliferation after ODN treatment was calculated as percent of non-treated controls. Invasion assays were set up after 48 h of ODN treatment as above. D, Attenuation of A431 tumorigenesis by continuous infusion of AS-ODN at 5 mg/kg/day. A431 seed tumor fragments freshly prepared as described in Methods, were transplanted s.c. into the right lateral flank of nude mice. Continuous infusion of ODNs was initiated 2 days prior to tumor transplantation. There were 5 mice in each treatment group. These results represent one of three similar experiments.
Figure 8B:
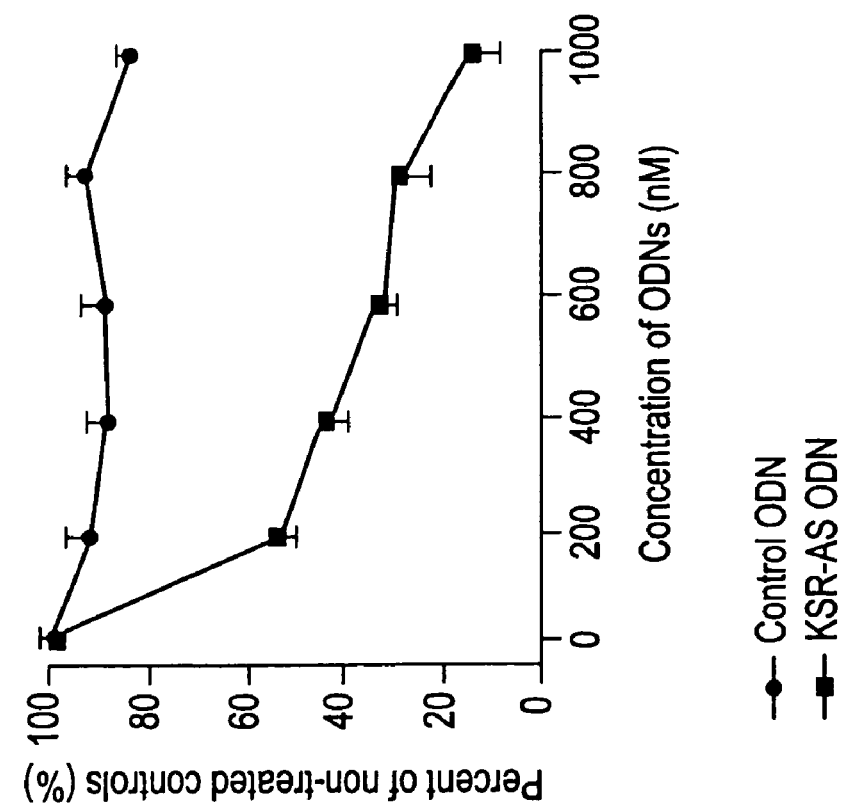

These observations demonstrate that inhibition of A431 tumorigenesis by KSR-AS involves attenuation of proliferation and induction of multinucleation. To confirm that prevention of A431 tumorigenesis by KSR-AS is due to inhibition of ksr1 expression by KSR-AS, we designed phosphorothioate AS-ODNs against the unique CA1 domain (SEQ ID NO: 1) (amino acids 42-82 (SEQ ID NO:2)) of KSR1, which is conserved between the mouse and human (12), to inactivate ksr1 expression pharmacologically. Among the AS-ODNs tested, the AS-ODN against nucleotides 214 to 231 (SEQ ID NO:5) of KSR1 (designated AS-ODN1(214-231)), which has no sequence homology to any other mammalian gene, exhibited the most potent and specific antisense effect, and was chosen for further characterization. In vitro treatment of A431 cells with 1 μM KSR AS-ODN (SEQ ID NO: 8) for 24 h resulted in a 90% reduction of endogenous KSR1 expression as determined by immunofluorescence staining (FIG. 8A) and Western blotting (not shown), while control ODNs had no apparent effect (FIG. 8A and not shown). Moreover, expression of other cellular proteins including the EGFR, H-Ras, c-Raf-1 and MAPK was not altered by treatment with KSR AS-ODN or control ODNs (not shown), indicating that the antisense effect was specific for KSR. Similar to inactivation of KSR by stable expression of full-length KSR-AS, KSR AS-ODN treatment attenuated A431 cell proliferation (FIG. 8B) and invasion (FIG. 8C) in a dose-dependent fashion ($p<0.05$). At 1 mM, KSR AS-ODN inhibited A431 cell proliferation and invasion by 80% and 70%, respectively. In contrast, Control-ODN (FIG. 8C), which lacks homology to any mammalian gene (16), or Sense-ODN or mismatch AS-ODNs (not shown), were ineffective.

Figure 8D:
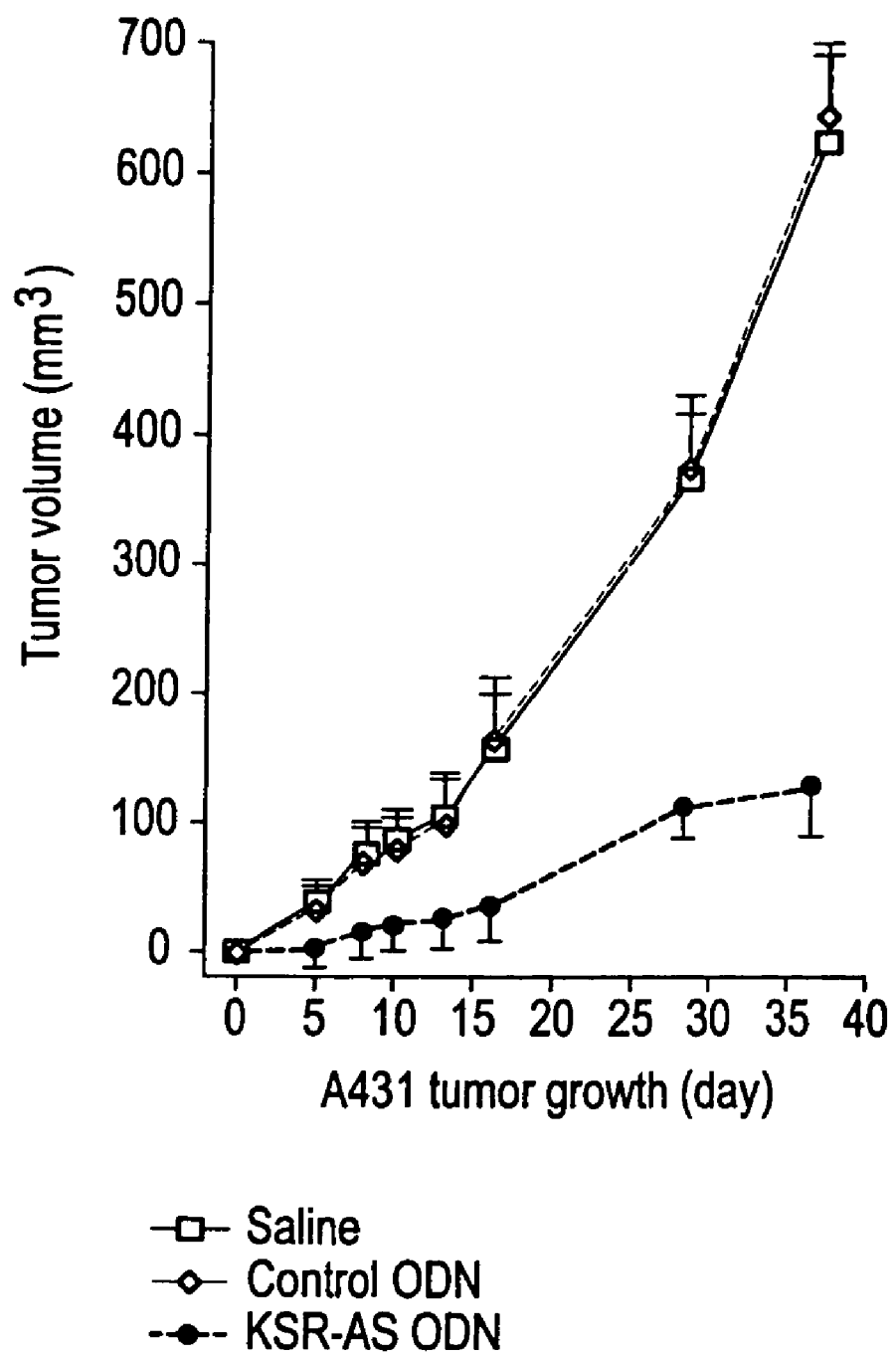

To assess the antitumor activity of KSR AS-ODNs in vivo, AS-ODNs or control ODNs were delivered via continuous s.c. infusion to provide sustained tumor exposure. Infusion was initiated two days prior to tumor implantation in order to reach a steady state ODN plasma level. $10^6$ A431 cells were injected s. c. into nude mice to obtain seed tumors of 400 mm$^3$. Approximately 50 mg of the freshly prepared seed tumor fragments were then transplanted to AS-ODN- or Control ODN-treated mice. Treatment with KSR AS-ODN at a low dose of 5 mg/kg/day effectively reduced tumoral KSR1 levels by 85% and attenuated A431 tumor growth by 80% (FIG. 8D, $p<0.01$), without apparent toxicity, consistent with the known lack of toxicity of this therapeutic approach (17). In contrast, no antitumor effects were observed following treatment with vehicle alone (saline) or with identical doses of the Control-ODN, or Sense-ODN (FIG. 8D and not shown). Similar results were obtained when treatment was initiated using mice with established A431 tumors of 150 mm$^3$ (not shown). Collectively, these results demonstrate that KSR1 is obligate for EGFR signaling of A431 tumorigenesis in vivo via hyperactivated wild type Ras. Further, the antitumor activity of KSR AS-ODNs appeared to be achieved via selective inhibition of ksr1 gene expression with high specificity. These studies suggest that it might be feasible to use KSR AS-ODN to abrogate EGFR/Ras signaling of human tumorigenesis.

Figure 9A:
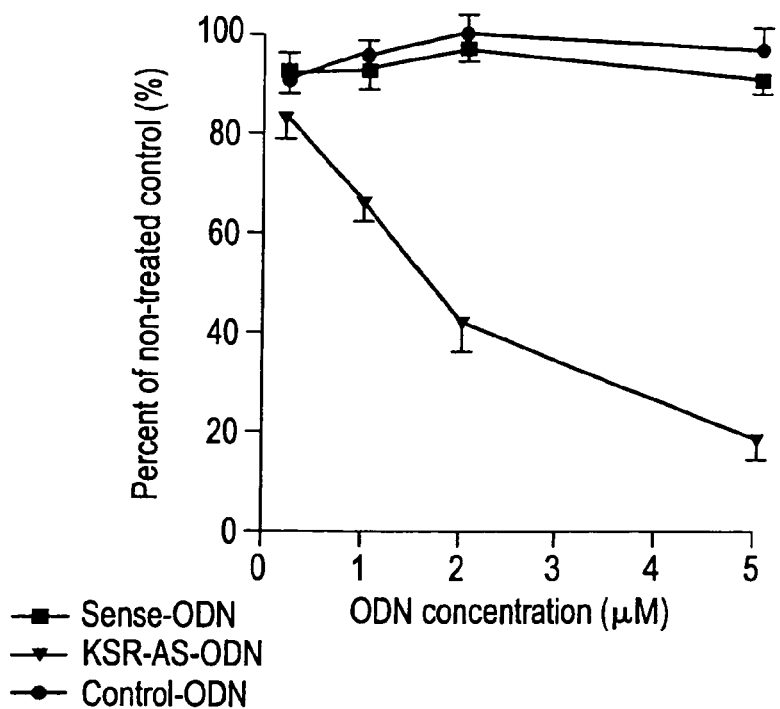
FIG. 9. Inactivation of KSR1 by AS-ODN inhibits oncogenic K-ras signaling in vitro in PANC-1. A, Dose-dependent inhibition of PANC-1 cell proliferation by AS-ODN treatment. PANC-1 cells were treated with the indicated doses of Control- or AS-ODNs and cell proliferation assays were performed as in FIG. 7. B, AS-ODN treatment (5 μM) attenuated the proliferation of a panel of human pancreatic cancer cell lines. The seeding density for each cell lines was determined in preliminary studies so that all cell lines were 30-40% confluent when transfected with ODNs. C and D, c-Raf-1 is epistatic to KSR1. PANC-1 cells were first treated with Sense- or AS-ODNs for 48 h and then transfected with the BXB-Raf as in Methods. 48 h after transfection, invasion and colony formation assays were set up as in FIG. 7. The inhibitory effect of AS-ODN on PANC-1 cell invasion (C) and transformation (D) was reversed by dominant positive BXB-Raf. E, AS-ODN treatment inhibited endogenous KSR1 expression in PANC-1 cells. Endogenous KSR1 was immunoprecipitated from non-treated (NT), Sense-ODN-treated or AS-ODN-treated PANC-1 cells, and KSR1 expression was determined by WB as described in Methods. Purified Flag-KSR served as a positive control for the WB. F, MAPK and PI-3 kinase activation in AS-ODN-treated and BXB-Raf-1-transfected PANC-1 cells in response to EGF were determined by WB analysis using phospho-MAPK and phospho-Akt specific antibodies as described in Methods. Under these conditions, b-actin and total Akt were unchanged (not shown). These results represent one of three similar experiments.
Figure 9B:
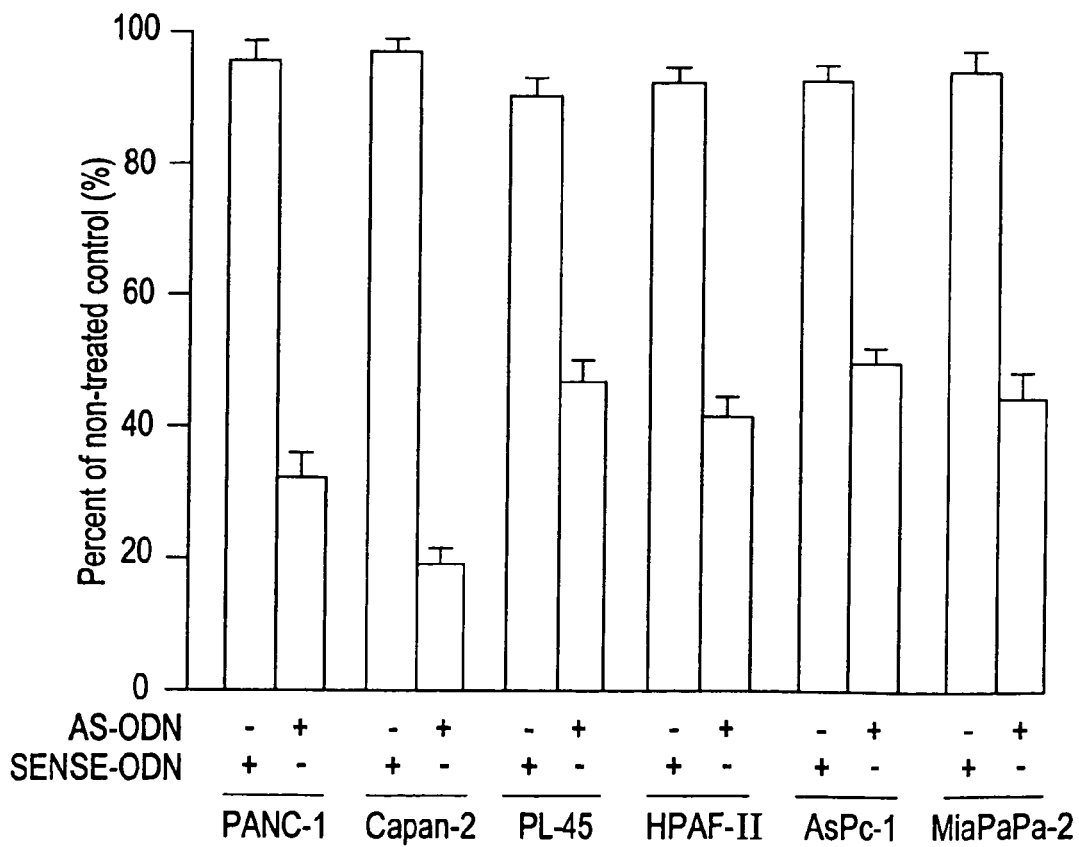
Figure 9E:
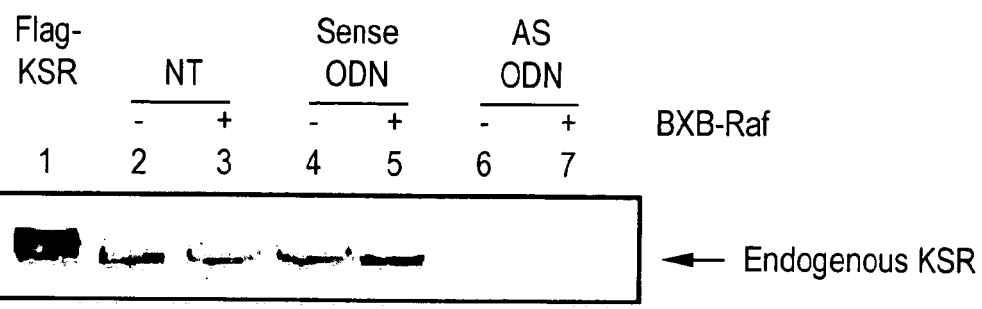

Inhibition of ksr1 expression abrogates oncogenic K-ras-mediated human pancreatic tumorigenesis via specific attenuation of Ras/Raf-MAPK signaling. To elucidate the importance of KSR1 in mediating oncogenic Ras signaling of human tumorigenesis and to explore the therapeutic potential of KSR AS-ODNs, we employed the human pancreatic cancer PANC-1 xenograft mouse model. This tumor manifests the oncogenic codon 12-mutation of K-ras. Similar to A431 cells, treatment of PANC-1 cells in vitro with KSR AS-ODNs attenuated cell proliferation (FIG. 9A), invasion (FIG. 9C) and transformation (FIG. 9D) in a dose-dependent fashion (FIG. 9 and not shown) ($p<0.05$ in each case). Further, treatment with 5 μM AS-ODN led to a 90% reduction of endogenous KSR1 expression (FIG. 9E). To confirm the effectiveness of KSR AS-ODN in inhibiting oncogenic K-ras function, a panel of codon-12 K-ras mutated human pancreatic cancer cell lines were treated with 5 μM of KSR AS-ODN and assayed for cell proliferation. While cell growth was inhibited by 50 to 80% in all cell lines after AS-ODN treatment ($p<0.01$ each), Sense-ODN had no apparent effect (FIG. 9B).

Figure 9F:
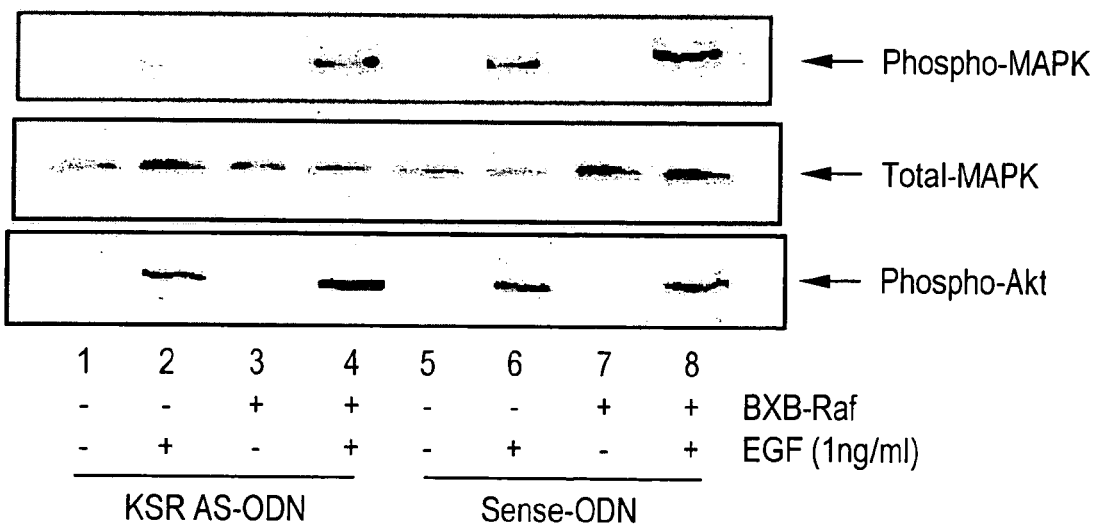
Figure 10A:
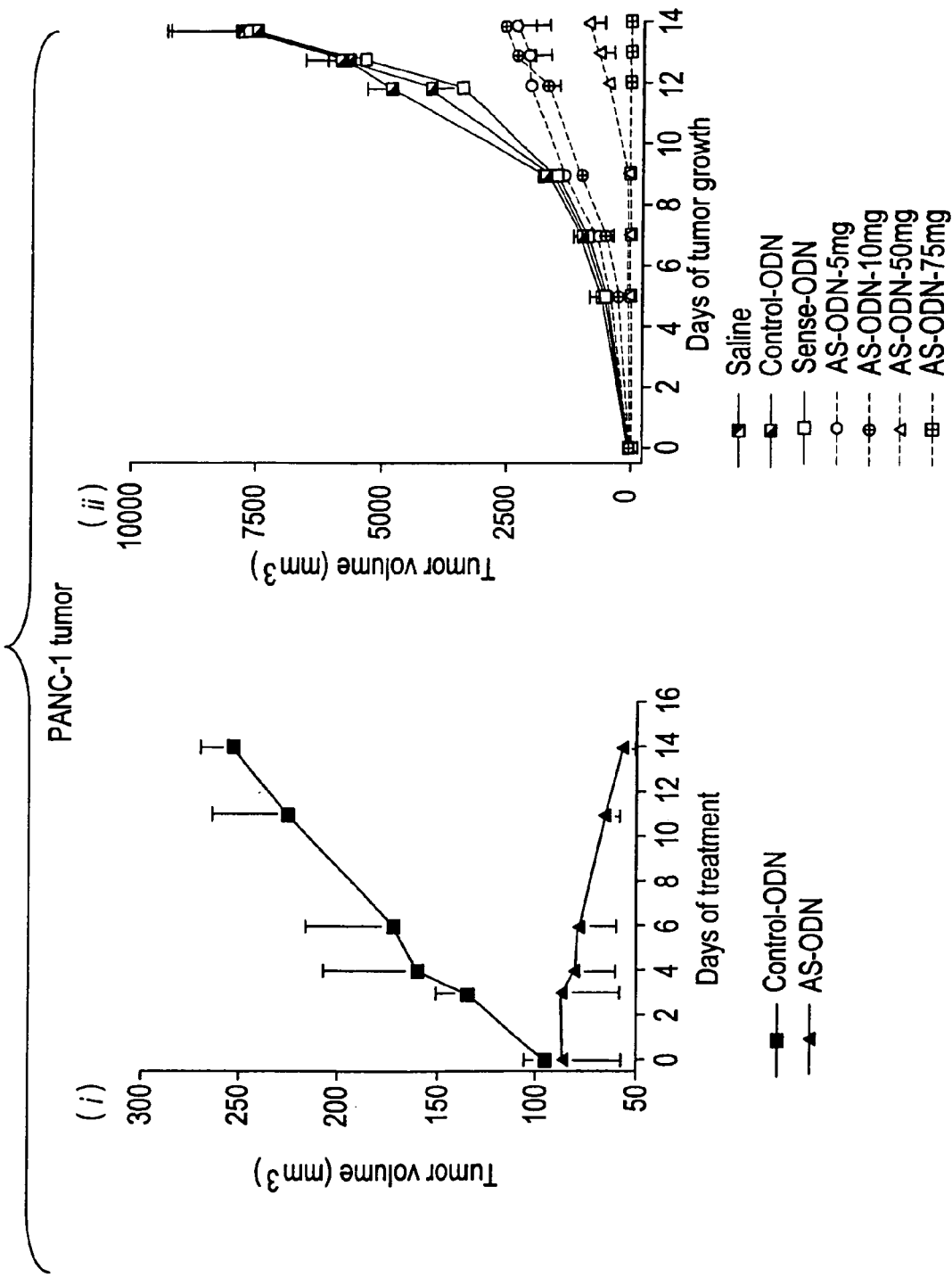
FIG. 10. AS-ODN treatment abolished PANC-1 and A549 tumorigenesis in vivo. A, Continuous infusion of AS-ODN abolished PANC-1 tumor growth. PANC-1 xenografts derived either from $10^6$ PANC-1 cells (i), or from freshly harvested seed PANC-1 tumors (ii) were transplanted into nude mice as described in Methods. A (i), established PANC tumors (approximately 100 mm$^3$) were treated with 10 mg/kg/day of Control- or AS-ODNs for 14 days. Mice bearing regressed AS-ODN-treated tumors were monitored up to 4 weeks. A(ii), freshly prepared PANC-1 seed tumor fragments were transplanted into nude mice as above. Infusion with ODNs was initiated two days prior to tumor implantation and continued for an additional 14 days. These results represent one of three similar experiments. There were 5 mice for each treatment group. B, AS-ODN treatment inhibited endogenous tumoral KSR1 expression. Tumoral KSR1 was immunoprecipitated from Saline-, Sense- or AS-ODN-treated PANC-1 tumors and its expression determined by WB as above. C, Inhibition of ksr1 had no effect of Ras activation in PANC-1 tumors. Ras activation status, measured by the amount of GTP-Ras in Saline-, Control-ODN-, Sense-ODN- or AS-ODN-treated PANC-1 tumors was determined using the Ras activation assay kit. D, KSR AS-ODN treatment prevented A549 tumor growth (i) and inhibited lung metastases via systemic dissemination (ii). A549 seed tumor fragments, freshly prepared as in Methods, were transplanted to nude mice. Treatment with control-or AS-ODNs were initiated when tumors reached 150 mm$^3$ and continued for additional 18 days (i). When animals were sacrificed at the end of the experiment, lungs were resected from control- or AS-ODN-treated mice and stained with Indian ink to visualize surface lung metastases derived via systemic dissemination (ii). These results represent one of three similar experiments. There were 5 mice for each treatment group.

We previously demonstrated that KSR1 activation is required for c-Raf-1 and subsequent MAPK activation in vitro in response to mitogenic doses of EGF stimulation (18,19). To molecularly order KSR1 and Raf-1 in oncogenic K-ras signaling, PANC-1 cells were treated with 5 μM AS-ODN, transfected with the dominant positive BXB-Raf-1 and assayed for cell invasion and transformation. If Raf-1 is downstream of KSR, gfRaf-1 (BXB-Raf-1) should reverse the inhibitory effect of KSR inactivation by AS-ODNs on PANC-1 cell invasion and transformation. Indeed, while BXB-Raf-1 had no effect on endogenous KSR1 expression (FIG. 9E), it completely reversed the inhibitory effect of AS-ODN on PANC-1 cell invasion (FIG. 9C) and transformation (FIG. 9D). These observations indicate that c-Raf-1 is epistatic to KSR1, consistent with our in vitro findings and with the current literature (19-22). Additional studies were performed to examine the mechanism by which KSR1 inactivation affected oncogenic Ras-mediated intracellular signaling. For these studies, AS-ODN-treated and BXB-Raf-1-transfected PANC-1 cells were serum-depleted for 48 h and stimulated with 1 ng/ml of EGF. MAPK and PI-3 kinase activation were assayed by Western blot analysis using phospho-MAPK and phospho-Akt specific antibodies. While AS-ODN treatment blocked EGF-induced MAPK activation (FIG. 9F, upper panel, lane 6 vs. lane 2), it had no apparent effect on Akt activation (FIG. 9F, lower panel, lane 6 vs. lane 2). Sense-ODN had no effect on either MAPK or Akt activation (FIG. 9F). Moreover, the inhibitory effect of AS-ODN on MAPK activation could be completely reversed by expression of BXB-Raf-1 (FIG. 9F, upper panel, lane 4 vs. lane 2). Total MAPK and Akt content were largely unaffected by treatment with ODNs or transfection with BXB-Raf-1 (FIG. 9F and not shown). These results suggest that abrogation of oncogenic K-Ras signaling in pancreatic cancer cells by KSR AS-ODN is likely achieved by specific inhibition of the Ras-Raf-MAPK cascade. To test the therapeutic potential of KSR AS-ODNs to treat human pancreatic cancer, PANC-1 xenografts either derived from $10^6$ cultured PANC-1 cells (FIG. 10A (i)), or from freshly harvested seed PANC-1 tumors (prepared as described above) (FIG. 10A (ii)), were transplanted into nude mice. The steady state plasma AS-ODN levels for the 5 and 10 mg/kg/day doses of infusion were determined by OliGreen and HPLC assays to be 63 and 123 ng/ml, respectively, consistent with that reported in the literature using similar doses (23). For PANC-1 tumors arising from the injected cells, tumors were allowed to reach 100 $mm^3$ prior to the initiation of AS-ODN treatment. Infusion of AS-ODNs at 10 mg/kg/day for 14 days resulted in 40% reduction in tumor volume with a 100% response rate (FIG. 10A (i), p<0.05 vs. Control-ODN). A group of AS-ODN treated tumors that had regressed were monitored for tumor re-growth after the treatment was discontinued. Only 1 of 5 tumors exhibited re-growth while the rest remained regressed and stable for up to 4 weeks (not shown). For PANC-1 xenografts propagated via serial passage in vivo, continuous infusion of KSR AS-ODNs, initiated 2 days prior to tumor transplantation, attenuated the growth of PANC-1 tumors in a dose-dependent fashion (FIG. 10A (ii)). No apparent toxicity (weight loss, behavioral alteration, organomegaly, inflammation, bleeding) was observed at any dose and was confirmed by histologic examination of numerous tissues at autopsy (not shown). At 75 mg/kg/day, PANC-1 tumor growth was completely abolished and all mice remain tumor-free up to 4 weeks after the treatment was discontinued (FIG. 10A (ii) and not shown). In contrast, treatment with vehicle alone (saline), Control-ODN, or Sense-ODN exhibited no antitumor effects at all doses examined (FIG. 10A and not shown). These observations support the conclusion that the antitumor effects observed for KSR AS-ODNs occur through an antisense mechanism of action. Similar anti-neoplastic effects of KSR AS-ODN were observed in PANC-1 tumors transplanted orthotopically under the pancreatic capsular tissue (not shown).

Figure 10B:
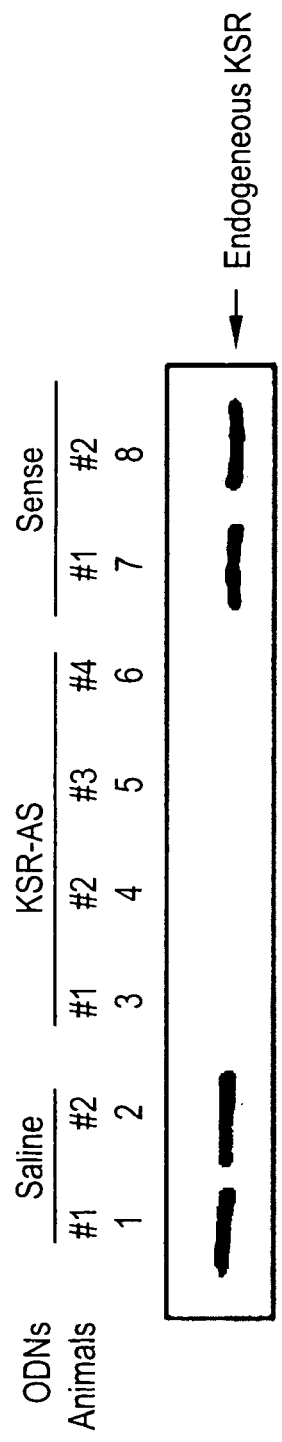
Figure 10C:
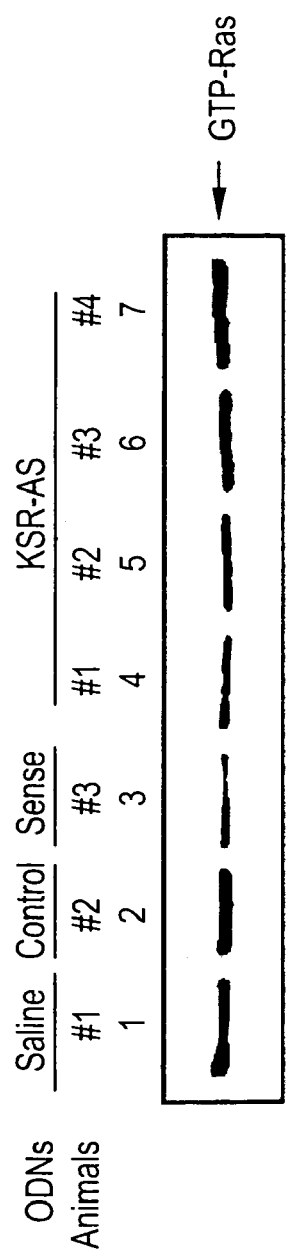

To confirm the specificity of KSR in mediating K-ras signaling of pancreatic tumorigenesis, we examined endogenous ksr1 gene expression in saline-, Sense-ODN and AS-ODN-infused PANC-1 tumors. KSR1 expression was inhibited by 90% in all AS-ODN-treated animals examined, while it was largely unchanged by saline or Sense-ODN infusion (FIG. 10B), confirming a sequence-specific target effect. As an additional control, the effect of AS-ODN treatment on Ras activation in vivo was measured by determining the amount of GTP-Ras in PANC-1 tumors using the GST-RBD-Raf-1 pull down assay as described in Methods. Consistent with the data of A431 and PANC-1 cells in culture (not shown), AS-ODN treatment had no apparent effect on Ras activation (FIG. 10C), indicating that signaling events upstream of Ras activation were intact and inactivation of oncogenic K-ras signaling in PANC-1 cells by KSR depletion occurs downstream of Ras.

Figure 10D:
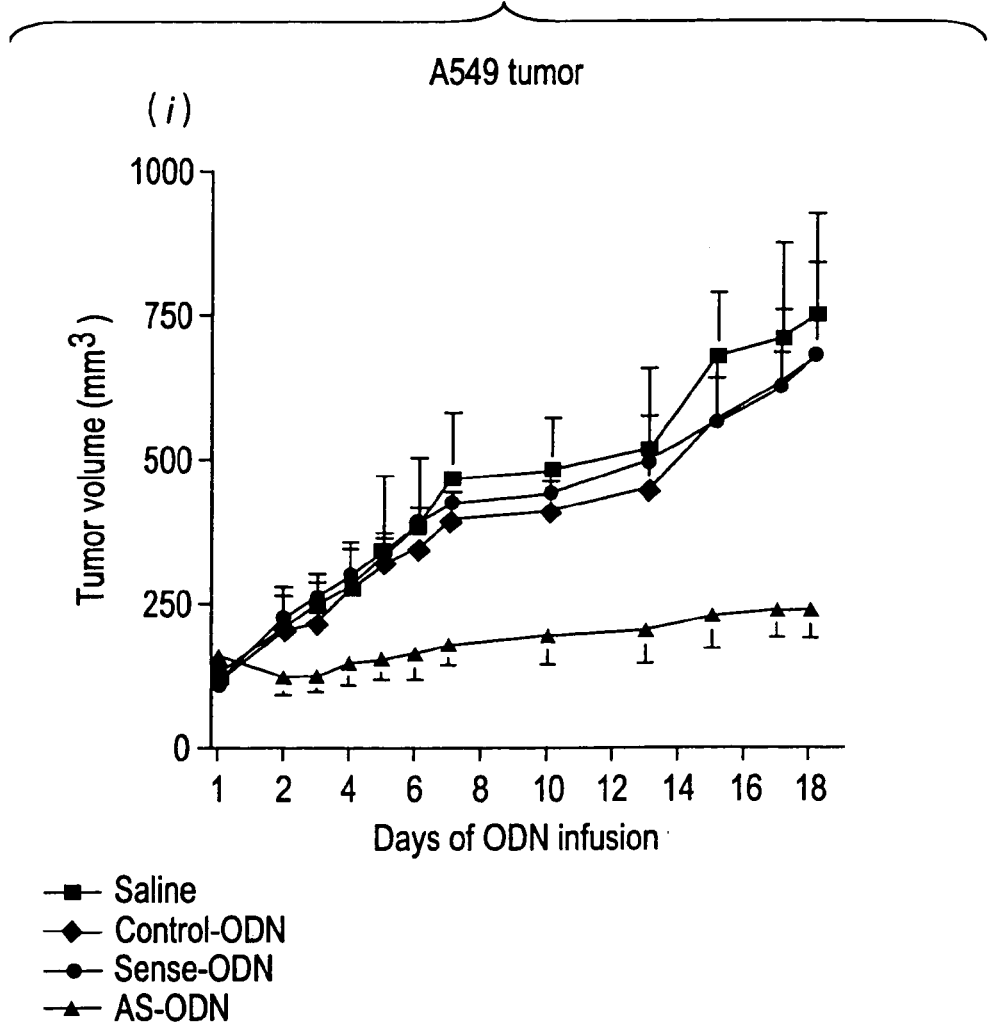

To confirm the effectiveness of KSR AS-ODNs in hindering other oncogenic K-ras-dependent human tumors, the codon 12 K-ras mutated A549 human non-small-cell lung carcinoma model (NSCLC) was selected. For these studies, 50 mg A549 seed tumor fragments, prepared similarly to A431 and PANC-1 seed tumors as above, were transplanted s. c. into nude mice. Treatment with KSR AS-ODN was initiated when A549 tumors reached 150 $mm^3$. At 10 mg/kg/day, KSR AS-ODN completely inhibited the growth of the established A549 tumors while Saline, Control-ODN or Sense-ODN had no apparent effect (FIG. 10D (i)). When animals were sacrificed at the end of the experiment, lungs were resected from Sense-ODN- or AS-ODN-treated mice and stained with Indian ink to visualize surface lung metastases derived via systemic dissemination. Control-ODN-treated lungs had an average of 8-11 metastatic foci. AS-ODN treatment elicited a dose-dependent inhibition of A549 lung metastasis (FIG. 10D (ii), p<0.05). These observations suggest that while KSR1 is obligate for K-ras-dependent primary tumor growth, it may also play an essential role in the metastatic progression of these tumors. Further, KSR AS-ODN could be an effective agent in the management of K-ras-dependent human malignancies.

Discussion

The present studies provide evidence that KSR1 is obligate for $gf$ Ras signaling at he tissue level, and that inhibition of ksr1 expression leads to selective regression of $gf$Ras-dependent tumors. Previous clinical studies designed to treat $gf$ Ras-dependent tumors by inhibition of elements of the Ras/Raf-1/MAPK signaling cascade have to date been largely unsuccessful (9). While toxicity for most agents has been acceptable, success of treatment has been limited by lack of specificity in inhibiting different Ras isoforms, which recent data suggest may have distinct biologic functions (24-26) and lack of selectivity towards $gf$ versus physiologic Ras signaling (8,9). Similar problems exists for experimental drugs designed to inhibit elements of the Raf-1/MEK1/MAPK cascade (9). The present studies on the effects of KSR AS-ODNs provide an approach to specifically attenuate $gf$ Ras signaling in the treatment of Ras-dependent human tumors.

While the targeting of DNA sequences with AS-ODN technology represents an attractive therapeutic approach to the treatment of cancer (27), a principle problem with this approach has been the designation of specificity of the AS-ODN effect for the gene of interest. We provide a number of different lines of evidence to support the notion that the inhibition of tumorigenesis observed with KSR AS-ODNs is due to selective inactivation of $gf$K-ras signaling via inhibition of ksr1. Our data show that genetic inhibition of ksr1 expression by the KSR-AS Tet-Off construct yielded comparable antisense-mediated effects in vitro and in vivo as KSR AS-ODNs. Further, various ODNs, designed to control for sequence-dependent and sequence-independent non-antisense artifacts, had no effects on ksr1 gene expression, or on tumor growth in cell culture or in vivo. In addition to ODN sequence specificity, the effects of KSR AS-ODN on ksr1 expression were specific for the intended target as expression of other genes of the EGFR-Ras-MAPK pathway was unaffected. Finally, conditional overexpression of KSR-S by A431 cells delivered a phenotype opposite to KSR inactivation by KSR-AS, and both KSR-S and KSR-AS effects were reversible in the Tet-Off system by turning off expression by Dox treatment. These results collectively attest that the antitumor effects of KSR AS-ODN are achieved by an antisense mechanism.

The lack of normal tissue toxicity in animals treated with KSR AS-ODNs is consistent with recent reports that ksr1 is dispensable for normal development in *C. elegans* and mice (10,11,13, and see Example 1 above). As recent investigations have uncovered a second ksr allele, ksr2 in *C. elegans* (28) and in mice (29), the lack of tissue toxicity after depletion of ksr1 by KSR AS-ODN might be due to compensation by ksr2 for normal cellular functions. Alternately, the lack of toxicity may reflect topological distribution of KSR. Recent evidence suggests that elements of the Ras/Raf-1/MAPK pathway are compartmentalized in more than one type of membrane microdomains (26,30), and that compartmentalization is associated with regulation of activity. In this regard, Ras and c-Raf-1 associate with sphingolipid enriched microdomains (also known as rafts) in the plasma membrane and with the bulk membrane fraction. Raft association, at least for c-Raf-1, appears to involve binding to the sphingolipid ceramide (31). Further, depending on activation status, Ras forms may traffic between compartments (32), with gf Ras preferentially targeting the bulk membrane.

Whether KSR, which some groups argue is ceramide-activated (20,33), plays a specific role in the gf Ras activation process, and hence its inactivation would marginally affect normal cellular function, will be the topic of future investigation. Lastly, the apparent lack of toxicity of our KSR ODN is not surprising as the phosphorothioate class of AS-ODNs, the most commonly used AS-ODNs, are generally well tolerated. Administration via continuous infusion in preclinical models and in human clinical trials have established that sequence-independent toxicities (activation of the complement system, prolongation of activated partial thromboplastin time and alterations of hematological parameters) are usually not encountered at doses at which pharmacologic antisense effects are achieved (34-36).

These studies also suggest that the therapeutic benefit of KSR AS-ODNs may not be limited to oncogenic K-ras-dependent human cancers, but might include a broader spectrum of tumor types, as our studies with KSR AS-ODNs were found effective against the tumor line A431, which is driven by hyperactivated wild type Ras. The therapeutic action of KSR AS-ODNs on established tumors in vivo likely involves both inhibition of tumor cell proliferation and induction of tumoral cell death. The anti-proliferative effect of KSR1 inactivation was evident by a decrease in cells in S phase and the induction of multinuclei phenotype in vitro and in vivo. Additionally, AS-ODN-treated A431 and PANC-1 tumors contained large necrotic areas (60-80% of the surface of the cut section). The mechanism of the latter effect, however, remains unknown. Previous studies demonstrated that significant microvascular endothelial apoptosis might also contribute to the anti-tumor effect as a result of ras inactivation (37). However, in our models, only sporadic endothelial cell apoptosis was detected by CD34 and TUNEL staining in PANC-1 tumors treated with KSR AS-ODNs (not shown). The role of KSR in angiogenesis must await further investigation in more relevant models of tumor angiogenesis.

Another important finding emerging from the present study is that KSR appears required for oncogenic Ras-mediated tumor metastatic progression. Inhibition of A549 lung metastases with KSR AS-ODN treatment is in agreement with our preliminary data that MMP-2 and 9 activities were increased in A431-KSR-S cells and inhibited in A431-KSR-AS cells (data not shown). Investigations are underway to elucidate the role of KSR in tumor progression.

The effective use of KSR AS-ODNs also provides the potential for improved understanding of the regulation of critical downstream events involved in gf Ras signaling, which at the present time, are only partially known. Raf-MAPK and PI-3 kinase modules are two established downstream pathways mediating gf Ras signaling of tumorigenesis (38-41). Here we provided evidence that KSR1 functions as a critical mediator of gf Ras likely via specific regulation of the Raf-1-MAPK signaling arm. Support for this notion is derived from recent studies demonstrating that MMTV-MT-dependent mammary tumor genesis, signaled primarily via src and PI-3 kinase via wild type Ras, was not affected in ksr −/− mice (13). In contrast, tumor genesis of oncogenic v-Ha-Ras-mediated epidermal skin tumors, signaled through the c-Raf-1/MAPK cascade, was abrogated in ksr1 −/− mice (Lozano and Kolesnick, unpublished). Further, the present studies with KSR antisense support the molecular ordering of c-Raf-1 as epistatic to mammalian KSR1, which is consistent with genetic results from *Drosophila* and *C. elegans* (10,11). We believe these observations may help to resolve some of the disputes regarding upstream elements of the Ras/Raf-1/MAPK module.

In summary, the current study provides original observations supporting KSR1 as a new molecular target for the treatment of human malignancies dependent on gf Ras signaling.

Methods

Cell culture and generation of Retro-Tet-Off A431 cell lines. Human epidermal carcinoma cell line A431, lung carcinoma cell line A549 and pancreatic cell lines PANC-1, Capan-2, PL-45, HPAF-II, AsPc-1 and MiapaPa-2 were obtained from ATCC (Manassas, Va.). The full-length wild type mouse ksr1 cDNA, which is over 90% identical to human ksr1 (12), was cloned in both sense (KSR-S) and antisense (KSR-AS) orientations into the pRetor-TRE under a doxycycline-inducible promoter in pRetro-Tet-Off (Clontech, Palo Alto, Calif.). DN-KSR (D683A/D700A/R589M) was sub-cloned similarly. A431 cells were infected with medium collected from PT67 packaging cells transfected with KSR-S, KSR-AS, DN-KSR or the empty vector, and maintained under double selection (0.1 mg/ml neomycin and 0.1 mg/ml Hygromycin).

Western blot, immunofluorescence and immunohistochemistry. Total cell lysates and tumor lysates were prepared in NP-40 buffer as described (18,42). Immunoprecipitation (IP) or Western blotting (WB) was performed according to the manufacturer's protocols with the following antibodies: monoclonal anti-Flag M2 antibody from Sigma (St Louis, Mo.), polyclonal anti-p44/42 MAPK, monoclonal anti-phospho-p44/42 MAPK (Thr202/Tyr204), polyclonal anti-phospho-MEK1/2 (Ser217/Ser221) and polyclonal anti-phospho-Akt (Ser 473) antibodies from Cell Signaling (Beverly, Calif.), and polyclonal anti-c-Raf-1 antibody from Upstate Biotechnology Inc. (Lake Placid, N.Y.). Endogenous KSR1 expression was determined by immunoprecipitation and WB analysis from 1 mg of total lysates or by immunofluorescence microscopy, using the monoclonal anti-KSR antibody (BD Biosciences, San Diego, Calif.)

(1:100 dilution) and HRP- or Texas-Red-conjugated goat anti-mouse secondary antibodies, respectively (Molecular Probes, Eugene, Oreg.). Histology and immunohistochemistry were performed on formalin-fixed, paraffin-embedded tumor or tissue specimens. 5 mm-cut sections were deparaffinized, rehydrated in graded alcohols, and H & E stained or immunostained using the avidin-biotin immunoperoxidase (Vector Laboratories, Burlingame, Calif.) method (43). The following primary antibodies were used: rat anti-mouse CD34 (1:50) antibody from PharMingen (San Diego, Calif.) and polyclonal anti-human Ki67 antibody (1:100) (Vector Laboratories). Diaminobenzidine was used as the chromogen and hematoxylin as the nuclear counterstain as described (43). Apoptosis were assessed by terminal deoxy transferase-mediated deoxyuridine triphosphate nick end labeling (TUNEL) (Roch, Mannheim, Germany) as described (43).

Proliferation, Matricel invasion and soft agar transformation assays. $2 \times 10^4$ A431 cells or $1-3 \times 10^4$ human pancreatic cells were plated in 6-well plates. The total number of cells/well was counted at the indicated time points to construct cell growth curves. For EGF treatment, 1.0 ng/ml of EGF was added to the culture and replaced every other day. The invasion assay was performed as described (42). Cells on the underside of the filters were counted in 10 randomly chosen fields (40× magnification) and reported as an average number of cells invaded per field. For EGF treatment, cells were replaced with serum-free medium for 2 h prior to the experiment. The Soft Agar assay was set up in 35 mm culture plates coated with 1.5 ml culture medium containing 0.5% agar and 5% FBS. $5 \times 10^3$ cells were suspended in 1.5 ml medium containing 0.1% agar and 5% FBS, and added to the agar pre-coated plates. Colonies consisting of more than 50 cells were scored after 14-21 days of incubation using a dissecting microscope. For EGF treatment, FBS was omitted from the culture medium.

Cell cycle analysis. Cell cycle distribution was determined by FACS analysis. For these studies, cell pellets collected from exponentially growing monolayers were washed twice with PBS containing 0.5% FBS and fixed with 100% ethanol for 15 min. Fixed cells were treated with RNase A (0.1 mg/ml) for 30 min at 37° C. and stained with propidium iodide (0.05 mg/ml). The proportion of cells in the different phases of the cell cycle was calculated from the experimental fluorescence histograms.

In vitro treatment with KSR AS-ODN. KSR1 AS-ODN (5'-CTTTGCCTCTAGGGTCCG-3') (SEQ ID NO: 8)(AS-ODN1(214-231)) and KSR sense-ODN (5'-CGGACCCTA-GAGGCAAAG-3') (SEQ ID NO: 15) were generated as phosphorothioate derivatives against nucleotides 214 to 231 (SEQ ID NO: 1) of the unique CA1 domain (amino acids (AAs) 42-82) of KSR1 by Genelink Inc. (Hawthorne, N.Y.). Control ODN (5'-CACGTCACGCGCGCACTATT-3') (SEQ ID NO: 16) was prepared similarly. For in vitro studies, ODNs were dissolved in sterile water and delivered to cells by Oligofectamine (Invitrogen, Carlsbad, Calif.) when cells were 30-40% confluent according to manufacturer's instructions. Cell proliferation was assayed at the indicated time points. 48 h after treatment, invasion and transformation assays were set up as above. For some studies, Control- and AS-ODN-treated PANC-1 cells were transfected with the dominant positive RSV-Raf-BXB (kindly provided by Dr. Joseph Bruder, NCI).

Tumor induction and in vivo treatment with KSR AS-ODN. For tumor induction, $10^6$ cultured tumor cells suspended in 0.1 ml of PBS, or 50 mg of tumor fragments freshly harvested from serial passaged seed tumors, were transplanted subcutaneously into the right lateral flank of 6-8 wk old male athymic NCRnu (Germantown, N.Y.). Tumor growth was measured every other day by calipers and tumor volume calculated as described (42). To determine the specificity of KSR-S on A431 tumorigenesis, a group of KSR-S tumor-bearing mice were fed with Dox-containing water (100 mg/ml). To determine the antitumor activity of KSR-AS ODN in vivo, infusion with Sense-, Control- or AS-ODNs via Alzet osmotic minipumps was initiated either 2 days prior to tumor transplantation or when tumor reached 100-150 mm³. A 5.0-75 mg/kg body weight/day dose range of ODN was chosen based on similar AS studies in vivo (34,44)

Ras activation assay. Ras activation status (GTP-Ras) in control ODNs or AS-ODN-treated PANC-1 cells or tumors was measured using the Ras activation assay kit (Upstate Biotechnology Inc., Lake Placid, N.Y.) according to manufacturer's instructions as described (45).

Statistical analysis. All data were evaluated by the Student's t test (two-tailed) with $p<0.05$ considered significant.

REFERENCES

1. Jemal, A., Thomas, A., Murray, T. & Thun, M. Cancer Statistics, 2002. *CA Cancer J Clin* 52, 23-47. (2002).
2. Burris, H. A., 3rd et al. Improvements in survival and clinical benefit with gemcitabine as first-line therapy for patients with advanced pancreas cancer: a randomized trial. *J Clin Oncol* 15, 2403-13. (1997).
3. Almoguera, C. et al. Most human carcinomas of the exocrine pancreas contain mutant c-K-ras genes. *Cell* 53, 549-54. (1988).
4. Smit, V. T. et al. KRAS codon 12 mutations occur very frequently in pancreatic adenocarcinomas. *Nucleic Acids Res* 16, 7773-82. (1988).
5. Bos, J. L. ras oncogenes in human cancer: a review. *Cancer Res* 49, 4682-9. (1989).
6. Hruban, R. H., Goggins, M., Parsons, J. & Kern, S. E. Progression model for pancreatic cancer. *Clin Cancer Res* 6, 2969-72. (2000).
7. Tada, M. et al. Analysis of K-ras gene mutation in hyperplastic duct cells of the pancreas without pancreatic disease. *Gastroenterology* 110, 227-31. (1996).
8. Adjei, A. A. Blocking oncogenic Ras signaling for cancer therapy. *J Natl Cancer Inst* 93, 1062-74. (2001).
9. Cox, A. D. & Der, C. J. Farnesyltransferase inhibitors: promises and realities. *Curr Opin Pharmacol* 2, 388-93 (2002).
10. Kornfeld, K., Hom, D. B. & Horvitz, H. R. The ksr-1 gene encodes a novel protein kinase involved in Ras-mediated signaling in *C. elegans*. *Cell* 83, 903-13 (1995).
11. Sundaram, M. & Han, M. The *C. elegans* ksr-1 gene encodes a novel Raf-related kinase involved in Ras-mediated signal transduction. *Cell* 83, 889-901 (1995).
12. Therrien, M. et al. KSR, a novel protein kinase required for RAS signal transduction. *Cell* 83, 879-88 (1995).
13. Nguyen, A. et al. Kinase suppressor of Ras (KSR) is a scaffold which facilitates mitogen-activated protein kinase activation in vivo. *Mol Cell Biol* 22, 3035-45 (2002).
14. Merlino, G. T. et al. Amplification and enhanced expression of the epidermal growth factor receptor gene in A431 human carcinoma cells. *Science* 224, 417-9 (1984).
15. Chang, W. P. & Little, J. B. Delayed reproductive death in X-irradiated Chinese hamster ovary cells. *Int J Radiat Biol* 60, 483-96 (1991).

16. Cotter, F. E. et al. Antisense oligonucleotides suppress B-cell lymphoma growth in a SCID-hu mouse model. *Oncogene* 9, 3049-55. (1994).
17. Agrawal, S., Temsamani, J. & Tang, J. Y. Pharmacokinetics, biodistribution, and stability of oligodeoxynucleotide phosphorothioates in mice. *Proc Natl Acad Sci USA* 88, 7595-9. (1991).
18. Xing, H. R., Lozano, J. & Kolesnick, R. Epidermal growth factor treatment enhances the kinase activity of kinase suppressor of Ras. *J Biol Chem* 275, 17276-80 (2000).
19. Xing, H. R. & Kolesnick, R. Kinase suppressor of Ras signals through Thr269 of c-Raf-1. *J Biol Chem* 276, 9733-41. (2001).
20. Yan, F., John, S. K. & Polk, D. B. Kinase suppressor of Ras determines survival of intestinal epithelial cells exposed to tumor necrosis factor. *Cancer Res* 61, 8668-75 (2001).
21. Anselmo, A. N., Bumeister, R., Thomas, J. M. & White, M. A. Critical contribution of linker proteins to Raf kinase activation. *J Biol Chem* 7, 7 (2001).
22. Wang, X. & Studzinski, G. P. Phosphorylation of raf-1 by kinase suppressor of ras is inhibited by MEK-specific inhibitors PD 098059 and U0126 in differentiating HL60 cells. *Exp Cell Res* 268, 294-300. (2001).
23. Gray, G. D. & Wickstrom, E. Rapid measurement of modified oligonucleotide levels in plasma samples with a fluorophore specific for single-stranded DNA. *Antisense Nucleic Acid Drug Dev* 7, 133-40. (1997).
24. Roy, S., Wyse, B. & Hancock, J. F. H-Ras signaling and K-Ras signaling are differentially dependent on endocytosis. *Mol Cell Biol* 22, 5128-40. (2002).
25. Koera, K. et al. K-ras is essential for the development of the mouse embryo. *Oncogene* 15, 1151-9. (1997).
26. Wolfman, A. Ras isoform-specific signaling: location, location, location. *Sci STKE* 2001, E2. (2001).
27. Kushner, D. M. & Silverman, R. H. Antisense cancer therapy: the state of the science. *Curr Oncol Rep* 2, 23-30. (2000).
28. Ohmachi, M. et al. *C. elegans* ksr-1 and ksr-2 have both unique and redundant functions and are required for MPK-1 ERK phosphorylation. *Curr Biol* 12, 427-33 (2002).
29. Roy, F., Laberge, G., Douziech, M., Ferland-McCollough, D. & Therrien, M. KSR is a scaffold required for activation of the ERK/MAPK module. *Genes Dev* 16, 427-38. (2002).
30. Prior, I. A. et al. GTP-dependent segregation of H-ras from lipid rafts is required for biological activity. *Nat Cell Biol* 3, 368-75. (2001).
31. Hekman, M. et al. Associations of B- and C-Raf with cholesterol, phosphatidylserine, and lipid second messengers: preferential binding of Raf to artificial lipid rafts. *J Biol Chem* 277, 24090-102. (2002).
32. Trahey, M. & McCormick, F. A cytoplasmic protein stimulates normal N-ras p21 GTPase, but does not affect oncogenic mutants. *Science* 238, 542-5. (1987).
33. Zhang, Y. et al. Kinase suppressor of Ras is ceramide-activated protein kinase. *Cell* 89, 63-72 (1997).
34. Geary, R. S., Leeds, J. M., Henry, S. P., Monteith, D. K. & Levin, A. A. Antisense oligonucleotide inhibitors for the treatment of cancer: 1. Pharmacokinetic properties of phosphorothioate oligodeoxynucleotides. *Anticancer Drug Des* 12, 383-93. (1997).
35. Henry, S. P., Monteith, D. & Levin, A. A. Antisense oligonucleotide inhibitors for the treatment of cancer: 2. Toxicological properties of phosphorothioate oligodeoxynucleotides. *Anticancer Drug Des* 12, 395-408. (1997).
36. Banerjee, D. Genasense (Genta Inc). *Curr Opin Investig Drugs* 2, 574-80. (2001).
37. Chin, L. et al. Essential role for oncogenic Ras in tumour maintenance. *Nature* 400, 468-72. (1999).
38. Stokoe, D., Macdonald, S. G., Cadwallader, K., Symons, M. & Hancock, J. F. Activation of Raf as a result of recruitment to the plasma membrane. *Science* 264, 1463-7. (1994).
39. Howe, L. R. et al. Activation of the MAP kinase pathway by the protein kinase raf. *Cell* 71, 335-42 (1992).
40. Rodriguez-Viciana, P. et al. Phosphatidylinositol-3-OH kinase as a direct target of Ras. *Nature* 370, 527-32 (1994).
41. Rodriguez-Viciana, P. et al. Role of phosphoinositide 3-OH kinase in cell transformation and control of the actin cytoskeleton by Ras. *Cell* 89, 457-67. (1997).
42. Xing, R. H., Mazar, A., Henkin, J. & Rabbani, S. A. Prevention of breast cancer growth, invasion, and metastasis by antiestrogen tamoxifen alone or in combination with urokinase inhibitor B-428. *Cancer Res* 57, 3585-93 (1997).
43. Paris, F. et al. Endothelial apoptosis as the primary lesion initiating intestinal radiation damage in mice. *Science* 293, 293-7. (2001).
44. Agrawal, S. & Zhao, Q. Antisense therapeutics. *Curr Opin Chem Biol* 2, 519-28 (1998).
45. Taylor, S. J. & Shalloway, D. Cell cycle-dependent activation of Ras. *Curr Biol* 6, 1621-7 (1996).

Example 3

Additional antisense oligonucleotides were synthesized and tested by proliferation assay in A431 cells as indicated in TABLE 1. Antisense nucleotides and their sequences were selected on the basis of ciiteria (based on hybridization conditions) to have no stable homodimer formation, no hairpin loop formation, no self-complementary sequences, and to have no stable duplex formation (<−6 kcal/mol. Sequences were selected using the Oligo 4 program (Molecular Biology Insights, Inc., Cascade, Colo.) and subsequently verified with the Oligo Tech program (Oligo Therapeutics Inc., Wilsonville, Oreg.). Antisense oligonucleotides were generated against nucleotides 151 to 168 (AS-ODN3 (151-168) (AS oligo sequence 5'-CAGCCCGCGCAGACT-GCC-3') (SEQ ID NO: 6) and nucleotides 181 to 198 (AS-ODN2(181-198)) (AS oligo sequence 5'-GAGGTCGT-TAGACACTGA-3') (SEQ ID NO: 7) of the KSR CA1 domain (both were P-S oligonucleotides). These oligonucleotides were tested along with the AS-ODN oligonucleotide against nucleotides 214 to 231 (AS-ODN1(214-231)) (AS oligo sequence SEQ ID NO: 8) described in Example 2. These antisense oligonucleotides represent reverse complements of nucleic acids encoding the amino acid sequences GSLRGL (SEQ ID NO: 17), AVSNDL (SEQ ID NO: 18) and RTLEAK (SEQ ID NO: 19) of the CA1 domain of KSR, respectively. A431 cells were transfected with the indicated amount of KSR AS-ODNs and cell proliferation was assessed 72 hr after the treatment. The effect of AS-ODN on A431 cell proliferation was presented as percent of inhibi tion of vehicle-treated (Oligofectamine alone) controls. This is a representation of one of four similar studies.

TABLE 1

Screening of KSR AS-ODNs by proliferation assay in A431 cells

| Concentration of ODN (nM) | AS151-168 (% inhibition) | AS181-198 (% inhibition) | AS214-231 (% inhibition) | Control ODN (% inhibition) |
|---|---|---|---|---|
| 10 | 0 | 0 | 8 | 2 |
| 50 | 0 | 5 | 20 | 3 |
| 100 | 3 | 15 | 25 | 2 |
| 200 | 16 | 23 | 42 | 0 |
| 400 | 24 | 42 | 67 | 4 |
| 800 | 38 | 58 | 87 | 3 |

Example 4

Figure 13A:
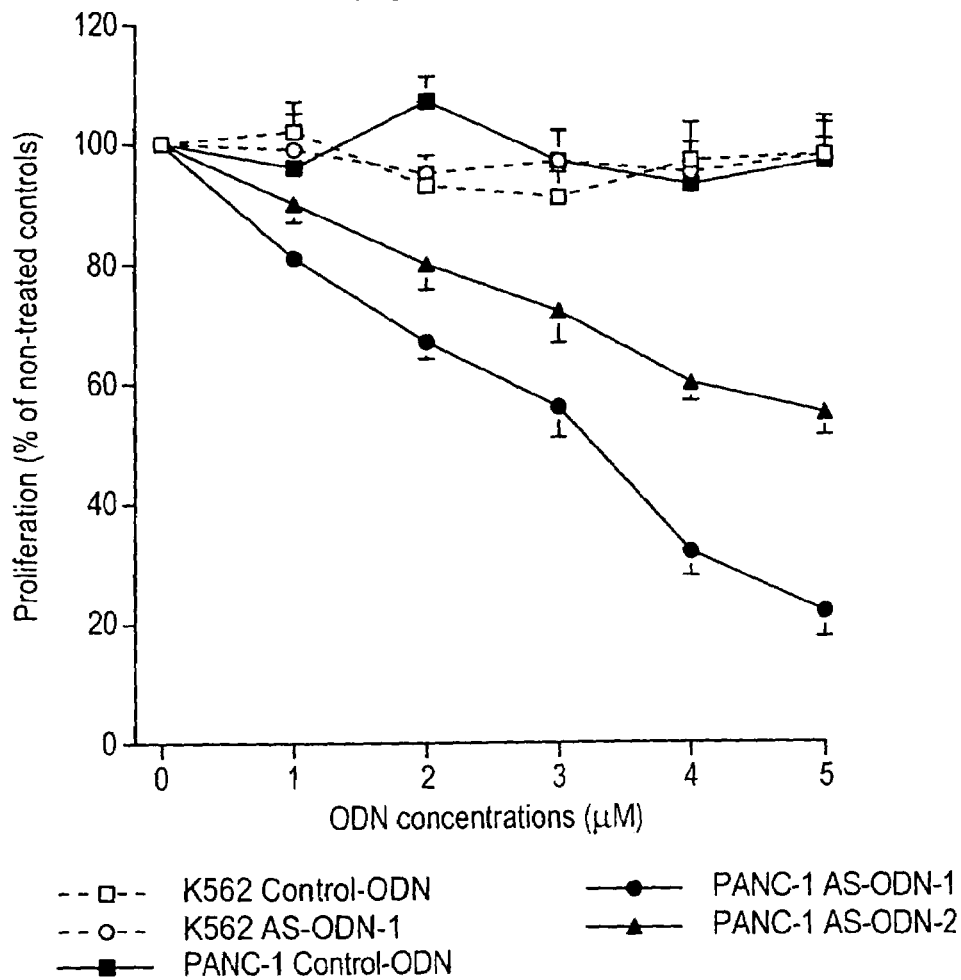
FIG. 13 depicts the specific and dose-dependent inhibition of PANC-1 cell proliferation by AS-ODN treatment. A, Dose-dependent inhibition of PANC-1 cell proliferation by AS-ODN treatment; proliferation of K562 cells is not inhibited by AS-ODN treatment. B, Western blot analysis of endogenous KSR1 gene expression in K562 and PANC-1 cells. Treatment of K562 cells with 5 μM KSR AS-ODN-1 elicited comparable reduction of endogenous KSR1 gene expression (over 80%) to that observed in PANC-1 cells.
Figure 13B:
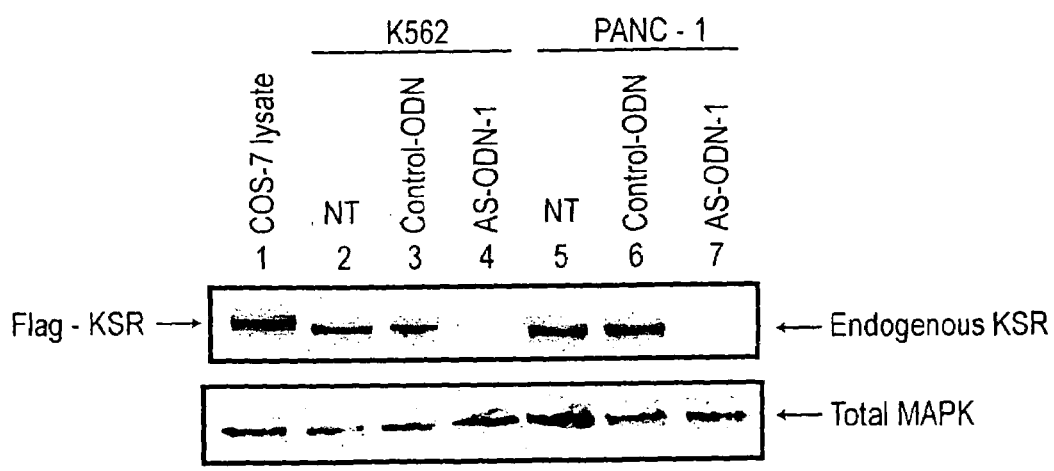

To stablish the specificity of KSR1 in mediating gf Ras signaling, the well-characterized human chronic myeloid leukemia cell line K562 was employed. K562 is Bcr-abl-driven and is therefore independent of gf Ras signaling. The specific and dose-dependent inhibition of PANC-1 cell proliferation by AS-ODN treatment is depicted in FIG. 13. PANC-1 and K562 cells were treated with the indicated doses of Control- or AS-ODNs and cell proliferation assays were performed (FIG. 13A). AS-ODN-1 and AS-ODN-2 correspond to nucleotides 214-231 and 181-198 of ksr1 cDNA, respectively. While PANC-1 cell proliferation was inhibited as expected, K562 cell proliferation was unaffected by ODN treatment. Treatment of K562 cells with 5 µM KSR AS-ODN-1 elicited comparable reduction of endogenous KSR1 gene expression (over 80%) to that observed in PANC-1 cells, as determined by Western blot analysis (FIG. 13B). Nonetheless, inhibition of proliferation was observed only in PANC-1 cells (FIG. 13A). Equal loading of the gels was confirmed using total P44/42 MAPK. Note that purified Flag-KSR, which served as a positive control for the Western blot, migrates slightly slower than endogenous KSR due to the Flag-tag (FIG. 13B). These results provide evidence that gf Ras signaling is specifically coupled to KSR1.

Example 5

Figure 18:
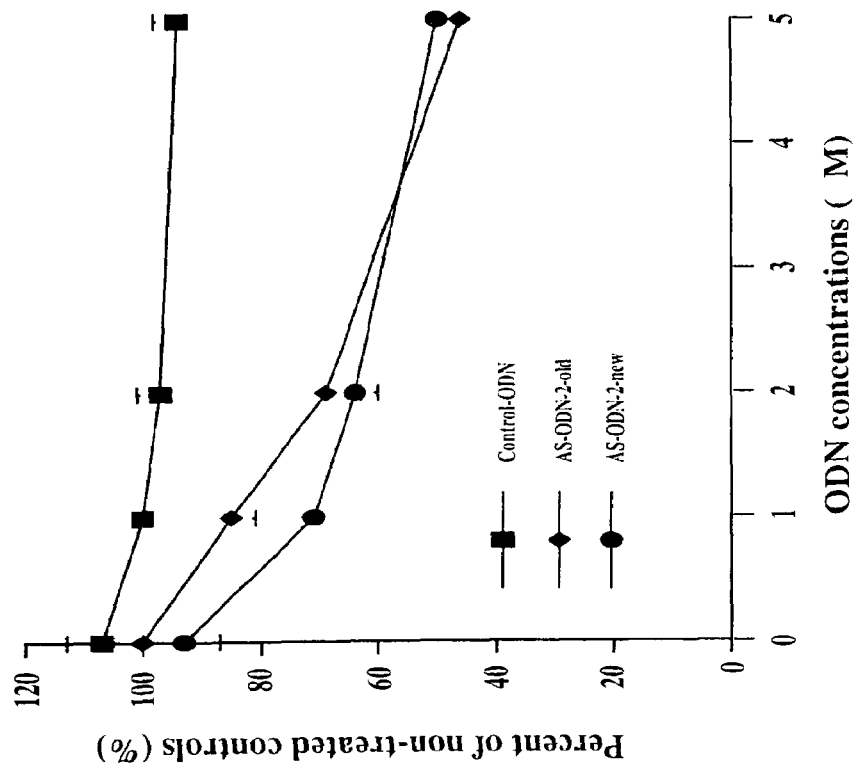
FIG. 18 depicts proliferation assay of PANC-1 cells treated with control ODN, AS-ODN2(181-198) (mouse) (AS-ODN2-old) and AS-ODN2(154-171) (human) (AS-ODN2-new).

The full length mRNA sequence of human KSR1 has been determined. The sequence is depicted in FIG. 14 (SEQ ID NO: 24). Antisense oligonucleotides, including those described above, were designed against the CA1 domain of human KSR nucleic acid. The human KSR antisense oligonucleotides are depicted on the annotated human KSR sequence in FIG. 15. Oligonucleotide AS-ODN1(187-204) (5'CTTTGCCTCTAGGGTCCG 3') (SEQ ID NO: 28) against nucleotides 187 to 204 of the human sequence corresponds in sequence to AS-ODN1(214-231) (SEQ ID NO:8) described above. Thus, AS-ODN1 is complementary to the nucleotides at positions 187-204 and 214-231 of the human and mouse cDNA, respectively. Oligonucleotide AS-ODN3(124-141) (5'CAGCCCGCGCAGACTGCC 3') (SEQ ID NO: 29) against nucleotides 124 to 141 of the human sequence corresponds in sequence to AS-ODN1 (151-168) (SEQ ID NO: 6) described above. Thus, AS-ODN3 is complementary to the nucleotides at positions 124-141 and 151-168 of the human and mouse cDNA sequences, respectively. Oligonucleotide AS-ODN2(154-171) is designed against nucleotides 154 to 171 of the human sequence. AS-ODN2 is complementary to nucleotides at positions 154-171 and 181-198 of the human and mouse cDNA, respectively. The human sequence differs by a single base pair in the most 5' bp of the antisense sequence from the mouse sequence in the corresponding position, with the human AS-ODN2(154-171) sequence being 5'GAG-GTCGTTAGACACTGC 3' (SEQ ID NO: 30) and the mouse sequence being 5'GAGGTCGTTAGACACTGA 3' (SEQ ID NO: 7) (the nucleotide difference is set out in bold). FIG. 16 depicts the annotated mouse KSR cDNA sequence with antisense oligonucleotides indicated. We have compared the original AS-ODN2(181-198) to the revised human AS-ODN2(154-171) and found they inhibited proliferation of PANG-1 cells, which are oncogenic K-ras-dependent human pancreatic cells, nearly identically (FIG. 18).

Example 6

We have designed additional potential AS-ODNs against other nucleotides of human KSR1. These ODNs (AS-ODN4 to AS-ODN12) are marked and annotated on human KSR1 nucleotide sequences in FIG. 17. TABLE 2 is a list of these newly designed ODNs (SEQ ID NOS: 31-39) with corresponding human nucleotide target sequence (SEQ ID NOS: 48-56).

TABLE 2

| AS-ODN ID # | Target Sequence (nt) (5'-3') | Sequence (5' to 3') |
|---|---|---|
| AS-ODN4 | ATGGGAGAGAAGGAGGGC (1-18) (SEQ ID NO:48) | GCCCTCCTTCTCTCCCAT (SEQ ID NO:31) |
| AS-ODN5 | CTGGTCCGTTACATTTGT (205-222) (SEQ ID NO:49) | ACAAATGTAACGGACCAG (SEQ ID NO:32) |
| AS-ODN6 | GTGGCTCCCGGTGAGAGG (247-264) (SEQ ID NO:50) | CCTCTCACCGGGAGCCAC (SEQ ID NO:33) |
| AS-ODN7 | GACTGGCTGTACACTTTC (298-315) (SEQ ID NO:51) | GAAAGTGTACAGCCAGTC (SEQ ID NO:34) |
| AS-ODN8 | GAGGCCGGAGGTGGTGCA (321-338) (SEQ ID NO:52) | TGCACCACCTCCGGCCTC (SEQ ID NO:35) |
| AS-ODN9 | AGATCCCCCGAGACCTCA (351-368) (SEQ ID NO:53) | TGAGGTCTCGGGGGATCT (SEQ ID NO:36) |

TABLE 2-continued

| AS-ODN ID # | Target Sequence (nt) (5'-3') | Sequence (5' to 3') |
|---|---|---|
| AS-ODN10 | ATGAATGAGGCCAAGGTG (379-396)<br>(SEQ ID NO:54) | CACCTTGGCCTCATTCAT<br>(SEQ ID NO:37) |
| AS-ODN11 | AGTTGGAGTTCATTGGAT (511-528)<br>(SEQ ID NO:55) | ATCCAATGAACTCCAACT<br>(SEQ ID NO:38) |
| AS-ODN12 | GCGGCGGGAAAGTGGCTC (531-548)<br>(SEQ ID NO:56) | GAGCCACTTTCCCGCCGC<br>(SEQ ID NO:39) |

Example 7

KSR Antisense Oligonucleotides as Radiosensitizers

Background

Although ionizing radiation (IR) remains a primary treatment for human cancers, the failure to respond to radiation therapy limits the efficacy of this modality. Accumulating evidence supports the contention that a signal transduction pathway, analogous to that for cell growth and differentiation leads to resistance to IR. More specifically, constitutive activation of the EGFR/Ras pathway via gf Ras or hyper-activation of EGFRs lead to radioresistance in human tumor cells (1-27). The precise mechanisms underlying this action of EGFR and Ras are not well understood. Hence, identification of downstream elements of EGFR and Ras effector signaling in response to IR is critical to the development of mechanism-based therapeutic strategies for IR treatment. Of the EGFR and Ras effector signaling pathways, the Ras-Raf-MAPK (10, 28-32) and Ras-PI3-Kinase (3,33,34) pathways have been implicated to mediate EGFR/Ras regulation of radiosensitivity to IR. The relative contribution of these two signaling pathways may be tumor-type specific.

Potential mechanisms underlying EGFR/Ras-mediated radioresistance include: increased capacity for DNA damage repair, accelerated repopulation of surviving tumor cells, resistance to IR-induced apoptosis and lack of IR-induced cell cycle check point delays. IR-induced EGFR/Ras activation results in a pronounced dose-dependent proliferative response via the MAPK signaling cascade, contributing at least in part, to the mechanism of accelerated proliferation, a cause contributing to the failure of radiotherapy (49,50). As an obligate mediator of the gfEGFR/Ras-Raf-1-MAPK signaling of tumor cell proliferation (51), inactivation of KSR may increase the efficacy of IR therapy by abrogating the accelerated repopulation of surviving tumor cells.

In addition to potentially mediating radiation resistance through EGFR and Ras, KSR may also transmit signals for the lipid second messenger ceramide. Emerging data suggest that IR acts directly on the plasma membrane of several cell types, activating acid sphingomyelinase, which generates ceramide by enzymatic hydrolysis of sphingomyelin. Ceramide then acts as a second messenger in initiating an apoptotic response that is cell-type and cell-context specific (13, 15, 35-38). In addition to the tyrosine kinase based mechanism that the EGFR utilizes for KSR activation, ceramide may also directly activate KSR. In this regard, KSR was originally identified by Kolesnick and co-workers as ceramide activate protein kinase (CAPK) (39). While ceramide can signal apoptosis in some cell types through the c-Jun kinase and transcriptional regulation of gene products, such as Fas ligand or TNFα that mediate the death response (13, 14,45), in other cells that contain the pro-apoptotic Bcl-2 family member BAD, ceramide induces apoptosis directly through a mechanism involving sequential Ras-dependent activation of KSR, c-Raf-1, and MEK1 (44, 46-48). In this case, the availability of a single target, such as BAD (44), converts the MAPK cascade, which is usually proliferative and/or anti-apoptotic, into a pro-apoptotic signaling pathway. Therefore, KSR may modulate radiosensitivity by regulation of ceramide-dependent and independent apoptotic responses in a cell-type specific manner. In support of the notion that KSR may prevent some forms of apoptosis from ensuing, Polk and co-workers showed that inactivation of KSR in YAMC colon cells antagonizes the anti-apoptotic signals emanating from TNF receptor, converting TNF into an inducer of apoptosis in these cells (41,42).

In the present example, we confine our studies to inactivation of the EGFR/Ras pathway as a proof-in-principle that this strategy can lead to radiosensitization. To explore this venue, we synthesized KSR specific AS-ODNs to pharmacologically inhibit KSR function (as described herein above) and employed A431 cells, which are driven through wild type Ras by an 100-fold overexpression of activated EGFR. When tested in vitro, AS-ODNs were specifically taken up into the nucleus, resulting in decreased endogenous KSR gene expression and inhibition of A431 proliferation, invasion, transformation and tumorigenesis (see Example 2). Moreover, here we demonstrate that inactivation of KSR via genetic (expression of KSR-AS) or pharmacological (AS-ODNs) approaches yields sensitization of A431 cells to IR-induced apoptosis in vitro.

Results

Figure 19:
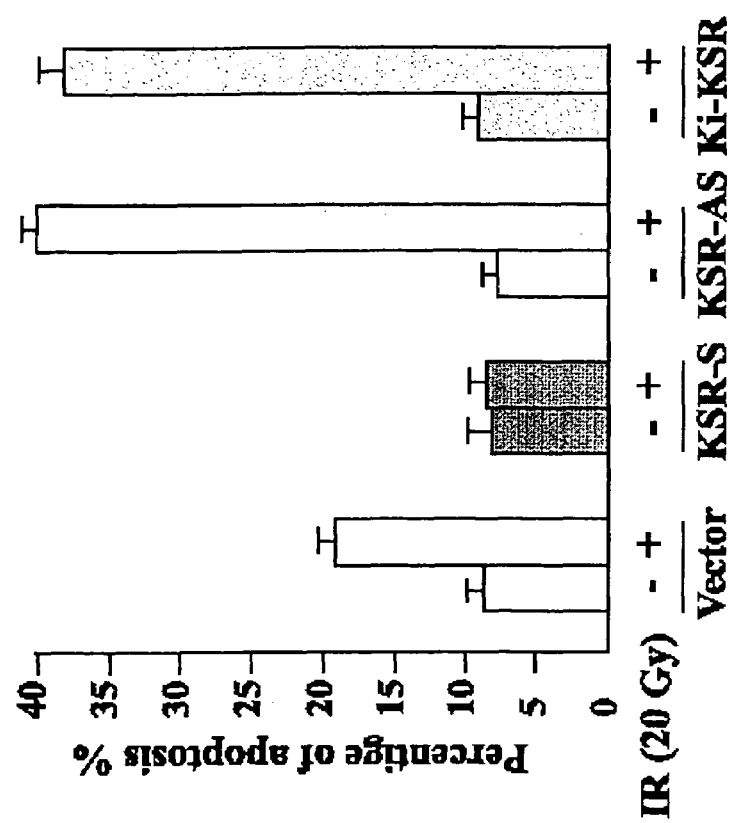
FIG. 19 presents percentage of ionizing-radiation induced apoptosis as scored with Annexin V staining in A431 cells expressing vector, wild-type Flag-KSR (KSR-S), Flag-AS-KSR (KSR-AS) or dominant-negative Flag-Ki-KSR (Ki-KSR).

AS-KSR and DN Ki-KSR sensitize A431 cells to IR-induced apoptosis: To test the hypothesis that inactivation of KSR might enhance the sensitivity to IR-induced cell killing, A431 cells stably-transfected with different KSR constructs were analyzed for their sensitivity to IR-induced apoptosis. A431 cells, due to the overexpression of activated EGFR, are known to be radioresistant (43). Serum-starved A431 cells were irradiated with a single dose of 20 Gy and apoptosis was deter-mined 24 hr post-IR by flow cytometry using Annexin V-FITC (Sigma). FIG. 19 shows that A431 cells overexpressing wild-type Flag-KSR (KSR-S) displayed minimal IR-induced apoptosis. Expression of Flag-AS-KSR (KSR-AS) or dominant-negative Flag-Ki-KSR (Ki-KSR) radiosensitized A431 cells, resulting in a substantial increase in IR-induced apoptosis (n=3). Nearly 40% of A431-KSR-AS and Ki-KSR cells underwent apoptosis 24 hr after IR. These results, although preliminary, strongly suggest that KSR may play a key role in cellular sensitivity to IR. Comparable results were obtained when apoptosis was scored with Bisbenzimide staining.

Figure 20:
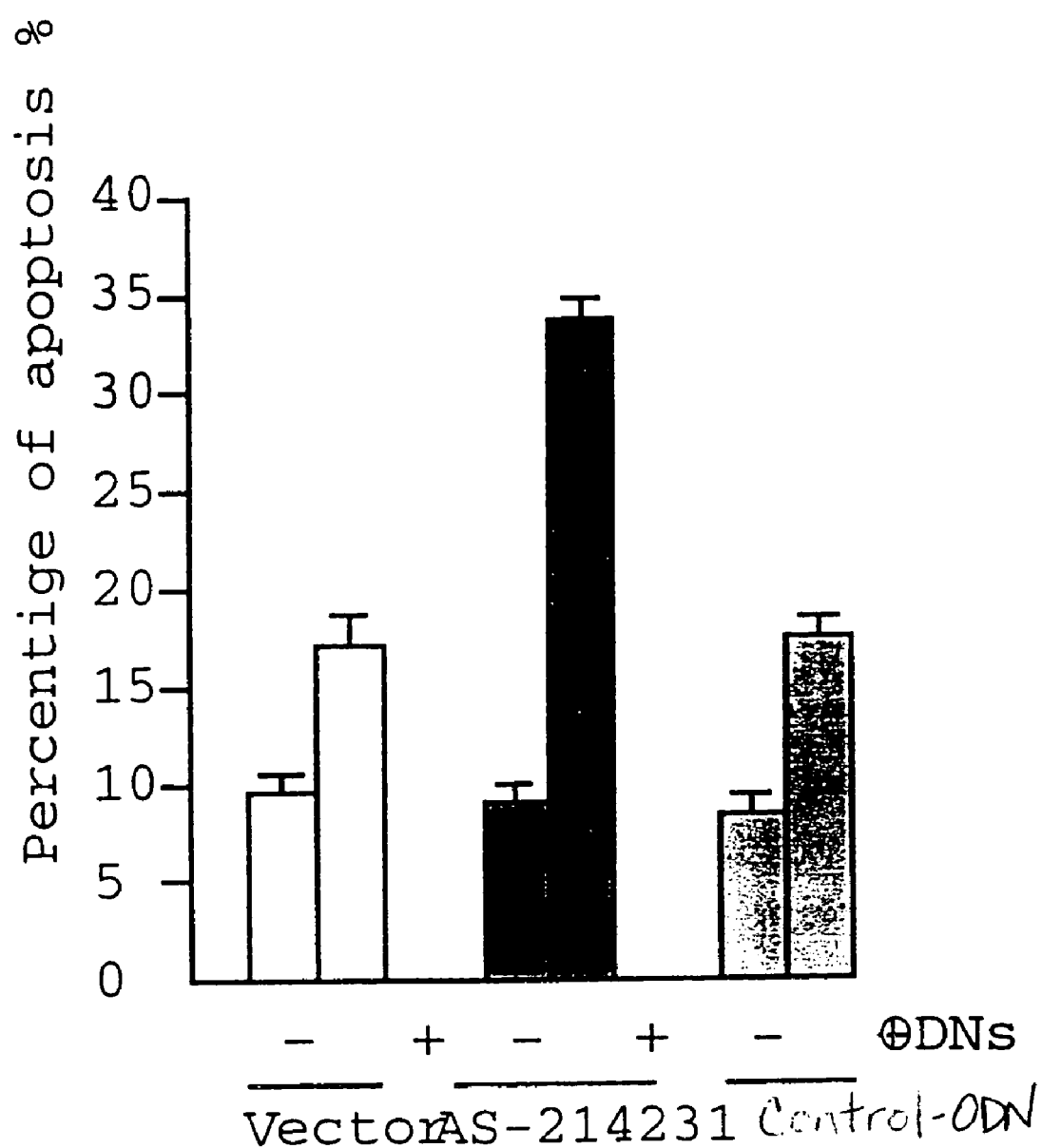
FIG. 20 presents percentage of ionizing-radiation induced apoptosis as scored with Annexin V staining in A431 cells treated with AS-ODN2(214-231), control ODN or expressing vector.

KSR AS-ODNs Sensitize A431 Cells to IR-induced Apoptosis:

As described above, abrogation of KSR function by a genetic approach (AS-KSR and DN-Ki-KSR) sensitized A431 cells to IR-induced apoptosis. To test the effectiveness of pharmacologic inhibition of KSR1 gene expression by AS-ODN on radiosensitivity, A431 cells were treated with 200 nM of AS-214231 for 36 hr prior to IR. Apoptosis was quantitated by flow-cytometry using Annexin V-FITC. As shown in FIG. 20, AS-214231 sensitized A431 cells, leading to a 2-fold increase in IR-induced apoptosis after 72 hours. The magnitude of this effect is comparable to that observed with overexpression of AS-KSR. In contrast, control ODN had no significant effect on radiation sensitivity to IR-induced apoptosis. It should be noted that at the concentration of Oligofectamine used, no significant elevation of basal level of apoptosis was detected (not shown). These results indicate that the radiosensitizing effect of AS-214231 is KSR sequence specific and that it might be feasible to use KSR AS-ODNs as radiosensitizers.

REFERENCES

1. Bernhard, E. J., Stanbridge, E. J., Gupta, S., Gupta, A. K., Soto, D., Bakanauskas, V. J., Cerniglia, G. J., Muschel, R. J., and McKenna, W. G. (2000). Direct evidence for the contribution of activated N-ras and K-ras oncogenes to increased intrinsic radiation resistance in human tumor cell lines. Cancer Res. 60: 6597-600.
2. Grant, M. L., Bruton, R. K., Byrd, P. J., Gallimore, P. H., Steele, J. C., Taylor, A. M., and Grand, R. J. (1990). Sensitivity to ionising radiation of transformed human cells containing mutant ras genes. Oncogene. 5: 1159-64.
3. Gupta, A. K., Bakanauskas, V. J., Cerniglia, G. J., Cheng, Y., Bernhard, E. J., Muschel, R. J., and McKenna, W. G. (2001). The Ras radiation resistance pathway. Cancer Res. 61: 4278-82.
4. Dent, P., Reardon, D. B., Park, J. S., Bowers, G., Logsdon, C., Valerie, K., and Schmidt-Ullrich, R. (1999). Radiation-induced release of transforming growth factor alpha activates the epidermal growth factor receptor and mitogen-activated protein kinase pathway in carcinoma cells, leading to increased proliferation and protection from radiation-induced cell death. Mol Biol Cell. 10: 2493-506.
5. Huang, S. M., and Harari, P. M. (2000). Modulation of radiation response after epidermal growth factor receptor blockade in squamous cell carcinomas: inhibition of damage repair, cell cycle kinetics, and tumor angiogenesis. Clin Cancer Res. 6: 2166-74.
6. Lammering, G., Valerie, K., Lin, P. S., Mikkelsen, R. B., Contessa, J. N., Feden, J. P., Farnsworth, J., Dent, P., and Schmidt-Ullrich, R. K. (2001). Radiosensitization of malignant glioma cells through overexpression of dominant-negative epidermal growth factor receptor. Clin Cancer Res. 7: 682-90.
7. Ling, C. C., and Endlich, B. (1989). Radioresistance induced by oncogenic transformation. Radiat Res. 120: 267-79.
8. McKenna, W. G., Weiss, M. C., Endlich, B., Ling, C. C., Bakanauskas, V. J., Kelsten, M. L., and Muschel, R. J. (1990). Synergistic effect of the v-myc oncogene with H-ras on radioresistance. Cancer Res. 50: 97-102.
9. Schmidt-Ullrich, R. K., Dent, P., Grant, S., Mikkelsen, R. B., and Valerie, K. (2000). Signal transduction and cellular radiation responses. Radiat Res. 153: 245-57.
10. Kasid, U., Suy, S., Dent, P., Ray, S., Whiteside, T. L., and Sturgill, T. W. (1996). Activation of Raf by ionizing radiation. Nature. 382: 813-6.
11. Wollman, R., Yahalom, J., Maxy, R., Pinto, J., and Fuks, Z. (1994). Effect of epidermal growth factor on the growth and radiation sensitivity of human breast cancer cells in vitro. Int J Radiat Oncol Biol Phys. 30: 91-8.
12. Carter, S., Auer, K. L., Reardon, D. B., Birrer, M., Fisher, P. B., Valerie, K., Schmidt-Ullrich, R., Mikkelsen, R., and Dent, P. (1998). Inhibition of the mitogen activated protein (MAP) kinase cascade potentiates cell killing by low dose ionizing radiation in A431 human squamous carcinoma cells. Oncogene. 16: 2787-96.
13. Santana, P., Pena, L. A., Haimovitz-Friedman, A., Martin, S., Green, D., McLoughlin, M., Cordon-Cardo, C., Schuchman, E. H., Fuks, Z., and Kolesnick, R. (1996). Acid sphingomyelinase-deficient human lymphoblasts and mice are defective in radiation-induced apoptosis. Cell. 86: 189-99
14. Xia, F., Wang, X., Wang, Y. H., Tsang, N. M., Yandell, D. W., Kelsey, K. T., and Liber, H. L. (1995). Altered p53 status correlates with differences in sensitivity to radiation-induced mutation and apoptosis in two closely related human lymphoblast lines. Cancer Res. 55: 12-5.
15. Chmura, S. J., Mauceri, H. J., Advani, S., Heimann, R., Beckett, M. A., Nodzenski, E., Quintans, J., Kufe, D. W., and Weichselbaum, R. R. (1997). Decreasing the apoptotic threshold of tumor cells through protein kinase C inhibition and sphingomyelinase activation increases tumor killing by ionizing radiation. Cancer Res. 57: 4340-7.
16. Pirollo, K. F., Tong, Y. A., Villegas, Z., Chen, Y., and Chang, E. H. (1993). Oncogene-transformed NIH 3T3 cells display radiation resistance levels indicative of a signal transduction pathway leading to the radiation-resistant phenotype. Radiat Res. 135: 234-43.
17. Fuks, Z., Persaud, R. S., Alfieri, A., McLoughlin, M., Ehleiter, D., Schwartz, J. L., Seddon, A. P., Cordon-Cardo, C., and Haimovitz-Ftiedman, A. (1994). Basic fibroblast growth factor protects endothelial cells against radiation-induced programmed cell death in vitro and in vivo. Cancer Res. 54: 2582-90.
18. Pirollo, K. F., Hao, Z., Rait, A., Ho, C. W., and Chang, E. H. (1997). Evidence supporting a signal transduction pathway leading to the radiation-resistant phenotype in human tumor cells. Biochem Biophys Res Commun. 230: 196-201.
19. Miller, A. C., Kariko, K., Myers, C. E., Clark, E. P., and Samid, D. (1993). Increased radioresistance of EJras-transformed human osteosarcoma cells and its modulation by lovastatin, an inhibitor of p21ras isoprenylation. Int J Cancer. 53: 302-7.
20. McKenna, W. G., Weiss, M. C., Bakanauskas, V. J., Sandier, H., Kelsten, M. L., Biaglow, J., Tuttle, S. W., Endlich, B., Ling, C. C., and Muschel, R. J. (1990). The role of the H-ras oncogene in radiation resistance and metastasis. Int J Radiat Oncol Biol Phys. 18: 849-59.
21. Bernhard, E. J., McKenna, W. G., Hamilton, A. D., Sebti, S. M., Qian, Y., Wu, J. M., and Muschel, R. J. (1998). Inhibiting Ras prenylation increases the radiosensitivity of human tumor cell lines with activating mutations of ras oncogenes. Cancer Res. 58: 1754-61.
22. Bernhard, E. J., Kao, G., Cox, A. D., Sebti, S. M., Hamilton, A. D., Muschel, R. J., and McKenna, W. G. (1996). The farnesyltransferase inhibitor FTI-277 radiosensitizes H-ras-transformed rat embryo fibroblasts. Cancer Res. 56: 1727-30.
23. Kavanagh, B. D., Dent, P., Schmidt-Ullrich, R. K., Chen, P., and Mikkelsen, R. B. (1998). Calcium-dependent stimulation of mitogen-activated protein kinase activity in A431 cells by low doses of ionizing radiation. Radiat Res. 149: 579-87.
24. Schmidt-Ullrich, R. K., Mikkelsen, R. B., Dent, P., Todd, D. G., Valerie, K., Kavanagh, B. D., Contessa, J. N., Rorrer, W. K., and Chen, P. B. (1997). Radiation-induced proliferation of the human A431 squamous carcinoma cells is dependent on EGFR tyrosine phosphorylation. Oncogene. 15: 1191-7.
25. Balaban, N., Moni, J., Shannon, M., Dang, L., Murphy, E., and Goldkorn, T. (1996). The effect of ionizing radiation on signal transduction: antibodies to EGF receptor sensitize A431 cells to radiation. Biochim Biophys Acta. 1314: 147-56.
26. Todd, D. G., Mikkelsen, R. B., Rorrer, W. K., Valerie, K., and Schmidt-Ullrich, R. K. (1999). Ionizing radiation stimulates existing signal transduction pathways involving the activation of epidermal growth factor receptor and ERBB-3, and changes of intracellular calcium in A431 human squamous carcinoma cells. J Recept Signal Transduct Res. 19: 885-908.
27. Reardon, D. B., Contessa, J. N., Mikkelsen, R. B., Valerie, K., Amir, C., Dent, P., and Schmidt-Ullrich, R. K. (1999). Dominant negative EGFR-CD533 and inhibition of MAPK modify JNK1 activation and enhance radiation toxicity of human mammary carcinoma cells. Oncogene. 18: 4756-66.
28. Kasid, U., Pfeifer, A., Brennan, T., Beckett, M., Weichselbaum, R. R., Dritschilo, A., and Mark, G. E. (1989). Effect of antisense c-raf-1 on tumorigenicity and radiation sensitivity of a human squamous carcinoma. Science. 243: 1354-6.
29. Hagan, M., Wang, L., Hanley, J. R., Park, J. S., and Dent, P. (2000). Ionizing radiation-induced mitogen-activated protein (MAP) kinase activation in DU145 prostate carcinoma cells: MAP kinase inhibition enhances radiation-induced cell killing and G2/M-phase arrest. Radiat Res. 153: 371-83.
30. Kasid, U. (2001). Raf-1 protein kinase, signal transduction, and targeted intervention of radiation response. Exp Biol Med (Maywood). 226: 624-5.
31. Gokhale, P. C., McRae, D., Monia, B. P., Bagg, A., Rahman, A., Dritschilo, A., and Kasid, U. (1999). Antisense raf oligodeoxyribonucleotide is a radiosensitizer in vivo. Antisense Nucleic Acid Drug Dev. 9: 191-201.
32. Park, J. S., Carter, S., Reardon, D. B., Schmidt-Ullrich, R., Dent, P., and Fisher, P. B. (1999). Roles for basal and stimulated p21(Cip-1/WAF1/MDA6) expression and mitogen-activated protein kinase signaling in radiation-induced cell cycle checkpoint control in carcinoma cells. Mol Biol Cell. 10: 4231-46.
33. Gupta, A. K., Bernhard, E. J., Bakanauskas, V. J., Wu, J., Muschel, R. J., and McKenna, W. G. (2000). RAS-Mediated radiation resistance is not linked to MAP kinase activation in two bladder carcinoma cell lines. Radiat Res. 154: 64-72.
34. Jones, H. A., Hahn, S. M., Bernhard, E., and McKenna, W. G. (2001). Ras inhibitors and radiation therapy. Semin Radiat Oncol. 11: 328-37.
35. Chmura, S. J., Nodzenski, E., Kharbanda, S., Pandey, P., Quintans, J., Kufe, D. W., and Weichselbaum, R. R. (2000). Down-regulation of ceramide production abrogates ionizing radiation-induced cytochrome c release and apoptosis. Mol Pharmacol. 57: 792-6.
36. Chmura, S. J., Nodzenski, E., Beckett, M. A., Kufe, D. W., Quintans, J., and Weichselbaum, R. R. (1997). Loss of ceramide production confers resistance to radiation-induced apoptosis. Cancer Res. 57: 1270-5.
37. Verheij, M., Ruiter, G. A., Zeip, S. F., van Blitterswijk, W. J., Fuks, Z., Haimovitz-Friedman, A., and Bartelink, H. (1998). The role of the stress-activated protein kinase (SAPK/JNK) signaling pathway in radiation-induced apoptosis. Radiother Oncol. 47: 225-32.
38. Rosette, C., and Karin, M. (1996). Ultraviolet light and osmotic stress: activation of the JNK cascade through multiple growth factor and cytokine receptors. Science. 274: 1194-7.
39. Zhang, Y., Yao, B., Delikat, S., Bayoumy, S., Lin, X. H., Basu, S., McGinley, M., Chan-Hui, P. Y., Lichenstein, H., and Kolesnick, R. (1997). Kinase suppressor of Ras is ceramide-activated protein kinase. Cell. 89: 63-72
40. Yao, B., Zhang, Y., Delikat, S., Mathias, S., Basu, S., and Kolesnick, R. (1995). Phosphorylation of Raf by ceramide-activated protein kinase. Nature. 378: 307-10.
41. Yan, F., and Polk, D. B. (2001). Kinase suppressor of ras is necessary for tumor necrosis factor alpha activation of extracellular signal-regulated kinase/mitogen-activated protein kinase in intestinal epithelial cells. Cancer Res. 61: 963-9.
42. Yan, F., John, S. K., and Polk, D. B. (2001). Kinase suppressor of Ras determines survival of intestinal epithelial cells exposed to tumor necrosis factor. Cancer Res. 61: 8668-75.
43. Kwok, T. T., and Sutherland, R. M. (1992). Cell cycle dependence of epidermal growth factor induced radiosensitization. Int J Radiat Oncol Biol Phys. 22: 525-7.
44. Basu S, Bayoumy S, Zhang Y, Lozano J, and Kolesnick R. (1998). BAD enables ceramide to signal apoptosis via Ras and Raf-1. J. Biol. Chem. 273: 30419-26.
45. Herr I., Wilhelm, D., Böhler T, Angel P. and Debatin K. (1997). Activation of CD95 (APO-1/Fas) signaling by ceramide mediates cancer therapy-induced apoptosis. EMBO J. 16:6200-08.
46. Susin, S. A., Zamzami, N., Castedo, M., Daugas, E., Wang, H. G., Geley, S., Fassy, F., Reed, J. C., and Kroemer, G. (1997) J. Exp. Med. 186, 25-37.
47. Smyth, M. J., Peny, D. K., Zhang, J., Poirier, G. G., Hannun, Y. A., and Obeid, L. M. (1996) Biochem. J. 316, 25-28.
48. Farschon, D. M., Couture, C., Mustelin, T., and Newmeyer, D. D. (1997) J. Cell Biol. 137, 1117-1125.
49. Tubiana, M. (1988). Repopulation in human tumors. A biological background for fractionation in radiotherapy. Acta Oncol. 27: 83-8.
50. Begg, A. C. (1994). Prediction of repopulation rates and radiosensitivity in human tumours. Int J Radiat Biol. 65: 103-8.
51. Xing, H. R., Cordon-Cardo, C., Deng, X., Tong, W., Campodonico, L., Fuks, Z., and Kolesnick, R. (2003). Pharmacologic inactivation of kinase suppressor of ras-1 abrogates Ras-mediated pancreatic cancer. Nat. Med. 9: 1267-8.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated antisense oligonucleotide that is 100% complementary to SEQ ID NO: 5, wherein the oligonucleotide is 18 to about 50 nucleotides in length.

2. The oligonucleotide of claim 1 labeled with a detectable label.

3. The oligonucleotide of claim 2 wherein the label is selected from enzymes, ligands, chemicals which fluoresce and radioactive elements.

4. The oligonucleotide of claim 1 wherein said oligonucleotide comprises at least one phosphorothioate linkage.

5. The oligonucleotide of claim 1, wherein the oligonucleotide is up to 30 nucleotides in length.

6. The oligonucleotide of claim 5, wherein the oligonucleotide is up to 25 nucleotides in length.

7. The oligonucleotide of claim 1, which is 18 nucleotides in length.

8. The oligonucleotide of claim 7, which is a phosphorothioate oligodeoxynucleotide.

9. The oligonucleotide of claim 1, which comprises a modified backbone.

10. The oligonucleotide of claim 9, wherein the modified backbone is selected from a phosphorothioate, phosphotriester, methyl phosphonate, polyamide, and a morpholino backbone.

11. The oligonucleotide of claim 1, which is an oligodeoxynucleotide.

12. A recombinant DNA molecule comprising a nucleic acid sequence which encodes on transcription an antisense RNA of 18 to about 50 nucleotides in length that is 100% complementary to SEQ ID NO: 5.

13. The recombinant DNA molecule of claim 12, wherein said nucleic acid sequence is operatively linked to a transcription control sequence.

14. The recombinant DNA molecule of claim 12, wherein the antisense RNA is up to 30 nucleotides in length.

15. The recombinant DNA molecule of claim 14, wherein the oligonucleotide is up to 25 nucleotides in length.

16. A cell line transfected with the recombinant DNA molecule of claim 13.

17. An expression vector that expresses a nucleic acid that is 100% complementary to SEQ ID NO: 5, wherein said nucleic acid inhibits expression of KSR and is 18 to about 50 nucleotides in length.

18. The expression vector of claim 17, wherein the oligonucleotide is up to 30 nucleotides in length.

19. The expression vector of claim 18, wherein the oligonucleotide is up to 25 nucleotides in length.

20. A pharmaceutical composition comprising a therapeutically effective amount of the antisense oligonucleotide of claim 1 and a pharmaceutically acceptable carrier or diluent.

21. A composition comprising the oligonucleotide of claim 1 and a pharmaceutically acceptable carrier or diluent.

22. A composition comprising one or more chemotherapeutic or radiotherapeutic agent and the oligonucleotide of claim 1, wherein the oligonucleotide inhibits KSR expression.

23. A composition comprising an expression vector and a pharmaceutically acceptable carrier or diluent, wherein said expression vector expresses a nucleic acid that is 100% complementary to SEQ ID NO: 5, wherein said nucleic acid inhibits expression of KSR and is 18 nucleotides to about 50 nucleotides in length.

24. The composition of claim 23, wherein the oligonucleotide is up to 30 nucleotides in length.

25. The composition of claim 24, wherein the oligonucleotide is up to 25 nucleotides in length.

26. A pharmaceutical composition comprising a therapeutically effective amount of the antisense oligonucleotide of claim 4 and a pharmaceutically acceptable carrier or diluent.

27. A composition comprising the oligonucleotide of claim 11 and a pharmaceutically acceptable carrier or diluent.

28. A composition comprising one or more chemotherapeutic or radiotherapeutic agent and the oligonucleotide of claim 4, wherein the oligonucleotide inhibits KSR expression.

* * * * *